United States Patent
Jorgensen et al.

(10) Patent No.: US 9,018,209 B2
(45) Date of Patent: Apr. 28, 2015

(54) COMPOUNDS AND METHODS FOR THE TREATMENT OF VIRUSES AND CANCER

(75) Inventors: William L. Jorgensen, Deep River, CT (US); Juliana Ruiz-Caro, Rainbach (AT); Andrew D. Hamilton, Guilford, CT (US)

(73) Assignee: Yale University, New Haven, CT (US)

( * ) Notice: Subject to any disclaimer, the term of this patent is extended or adjusted under 35 U.S.C. 154(b) by 1559 days.

(21) Appl. No.: 11/991,583

(22) PCT Filed: Sep. 25, 2006

(86) PCT No.: PCT/US2006/037173
§ 371 (c)(1),
(2), (4) Date: Jul. 7, 2008

(87) PCT Pub. No.: WO2007/038387
PCT Pub. Date: Apr. 5, 2007

(65) Prior Publication Data
US 2010/0222352 A1    Sep. 2, 2010

Related U.S. Application Data

(60) Provisional application No. 60/720,307, filed on Sep. 23, 2005, provisional application No. 60/730,934, filed on Oct. 27, 2005, provisional application No. 60/781,486, filed on Mar. 9, 2006, provisional application No. 60/836,723, filed on Aug. 10, 2006, provisional application No. 60/842,901, filed on Sep. 7, 2006.

(51) Int. Cl.
| | |
|---|---|
| *A61K 31/513* | (2006.01) |
| *A61K 31/495* | (2006.01) |
| *A61K 31/519* | (2006.01) |
| *A61K 31/44* | (2006.01) |
| *A61K 31/425* | (2006.01) |
| *C07D 251/42* | (2006.01) |
| *C07D 491/00* | (2006.01) |
| *C07D 495/00* | (2006.01) |
| *C07D 471/04* | (2006.01) |
| *C07D 277/42* | (2006.01) |

(Continued)

(52) U.S. Cl.
CPC ............ *C07D 277/42* (2013.01); *C07D 213/74* (2013.01); *C07D 217/22* (2013.01); *C07D 239/42* (2013.01); *C07D 239/47* (2013.01); *C07D 239/48* (2013.01); *C07D 239/94* (2013.01); *C07D 251/42* (2013.01); *C07D 277/56* (2013.01); *C07D 471/04* (2013.01); *C07D 487/04* (2013.01); *C07D 493/04* (2013.01)

(58) Field of Classification Search
None
See application file for complete search history.

(56) References Cited

U.S. PATENT DOCUMENTS

| 5,041,442 A | 8/1991 | Romero et al. |
|---|---|---|
| 6,040,311 A * | 3/2000 | Duggan et al. ................ 514/275 |

(Continued)

FOREIGN PATENT DOCUMENTS

| EP | 0205983 | 10/1991 |
|---|---|---|
| WO | WO9515954 | 6/1995 |

(Continued)

OTHER PUBLICATIONS

Tomita et al., Synthesis of Thiazole Derivatives Containing Diphenyl Ether Nucleus II., Yakugaku Zasshi, Vo. 75 (1955), No. 9, pp. 1077-1081.*
Aggarwal, V. K.; Vasse, J.-L. *Org. Lett.* 2003, 5, 3987.
Bracher, F.; Daab, J. Eur. J. Org. Chem. 2002, 2288.
Cain, M. E. *J. Chem. Soc.* 1964, 3532.
Dondoni, A.; Fantin, G.; Fogagnolo, M.; Medici, A.; Pedrini, P. *Tetrahedron* 1988, 44, 2021.
Doyle, M. P.; Siegfried, B.; Dellaria, J. F. J. Org. Chem. 1977, 42, 2426.

(Continued)

*Primary Examiner* — Sreeni Padmanabhan
*Assistant Examiner* — Jody Karol
(74) *Attorney, Agent, or Firm* — Henry D. Coleman; R. Neil Sudol

(57) ABSTRACT

The present invention relates to compounds according to the formula I: Where $R^a$ is H or an optionally OH-substituted $C_1$-$C_3$ alkyl; $R_1$ is $OR^1$, an optionally substituted $C_{4-12}$ carbocyclic group which may be saturated or unsaturated (including aromatic) or an optionally substituted heterocyclic group; $R^1$ is an optionally substituted $C_1$-$C_{14}$ hydrocarbyl group or an optionally substituted heterocyclic group; $R_2$, $R_3$ and $R_4$ are each independently H, an optionally substituted $C_1$-$C_4$ alkyl group (preferably $CH_3$, $CH_2CH_3$ or $CF_3$), halogen (preferably F, Cl, Br), OR, CN, $NO_2$, a $C_1$-$C_6$ thioether, a $C_1$-$C_6$ thioester group, an optionally substituted $CO_2R$ group, an optionally substituted COR group or an optionally substituted OCOR group (preferably $R_4$ is H); R is H or an optionally substituted $C_1$-$C_6$ alkyl group; RHET is an optionally substituted heterocyclic group; and pharmaceutically acceptable salts, solvates or polymorphs thereof.

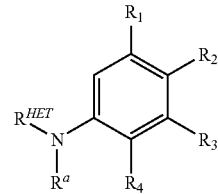

(I)

29 Claims, No Drawings

(51) Int. Cl.

| | | |
|---|---|---|
| *C07D 213/74* | (2006.01) | |
| *C07D 217/22* | (2006.01) | |
| *C07D 239/42* | (2006.01) | |
| *C07D 239/47* | (2006.01) | |
| *C07D 239/48* | (2006.01) | |
| *C07D 239/94* | (2006.01) | |
| *C07D 277/56* | (2006.01) | |
| *C07D 487/04* | (2006.01) | |
| *C07D 493/04* | (2006.01) | |

(56) References Cited

U.S. PATENT DOCUMENTS

2002/0151566 A1* 10/2002 Schumacher et al. ........ 514/317
2004/0102630 A1    5/2004 Brumby et al.

FOREIGN PATENT DOCUMENTS

WO     WO 03049542 A1 *  6/2003
WO     WO2005061516        7/2005

OTHER PUBLICATIONS

Elzbieta, D.; Zygmunt, E. *Przemysl Chemiczny* 1963, 42, 433.
Gong, Y.; Pauls, H. W. *Synlett*. 2000, 829.
Hager, D. C.; Bentrude, W. G. *J. Org. Chem.* 2000, 65, 2786.
Harden, D. B.; Mokrosk, M. J.; Strekowski, L. *J. Org. Chem.* 1988, 53, 4137.
Harding, K. E.; Clement, K. S. *J. Org. Chem.* 1984, 49, 2049.
Imakura, Y.; Okimoto, K.; Tonishi, T.; Hisazumi, M.; Yamazaki, *J. Chem. Pharm. Bull.* 1992, 40, 1691.
Katritzky, A. R.; Baykut, G.; Rachwal, S.; Szafran, M.; Caster, K. C.; Eyler, J. *J. Chem. Soc., Perkin Trans. II* 1989, 1499.
Kel'in, A. V.; Sromek, A. W.; Gevorgyan, V. *J. Am. Chem. Soc.* 2001, 123, 2074-2075.
Kim, J. T.; Gevorgyan, V. *Org. Lett.* 2002, 4, 4697-4699.
Kim, J. T.; Butt, J.; Gevorgyan, V. I *Org. Chem.* 2004, 69, 5638-5645.
Lemieux, R. M.; Meyers, A. I. *J. Am. Chem. Soc.* 1998, 120, 5453.
Lepore, S. D.; He, Y. *J. Org. Chem.* 2003, 68, 8261.
Mandal, S. S.; Chakraborty, J.; De, A. *J. Chem. Soc., Perkin Trans. 1* 1999, 2639.
Mangalagiu, I.; Benneche, T.; Undheim, K. *Acta Chem. Scand.* 1996, 50, 914.
Minakawa, N.; Kojima, N.; Hikishima, S.; Sasaki, T.; Kiyosue, A.; Atsumi, N.; Ueno, Y.; Matsuna, A. *J. Am. Chem. Soc.* 2003, 125, 9970.
Rossi, R.; Carpita, A.; Lippolis, V.; Benetti, M. *Gazz. Chim. Ital.* 1990, 120, 783.
Shiotani, S.; Morita, H. *J. Heterocycl. Chem.* 1982, 19, 1207-9.
Simkovsky, N. M.; Ermann, M.; Roberts, S. M.; Parry, D. M.; Baxter, A. D. *J. Chem. Soc., Perkin Trans.* 1 2002, 1847.
Tixier, C.; Sancelme, M.; Bonnemey, F.; Cuer, A.; Veschambre, H. *Environ. Toxicol. Chem.* 2001, 20, 1381.
Tullis, J. S.; VanRens, J. C.; Natchus, M. G.; Clark, M. P.; De, B.; Hsieh, L. C.; Janusz, M. *J. Bioorg. Med. Chem. Lett.* 2003, 13, 1665.
Young, C. G.; James, B. R.; Rettig, S. J. *Can. J. Chem.* 1985, 63, 1035.
Zanetti, J. E. *J. Am. Chem. Soc.* 1927, 49, 1065.
Zhang, Z.; Yang, Z.; Meanwell, N. A.; Kadow, J. F.; Wang, T. *J. Org. Chem.* 2002, 34, 2345-2347.

\* cited by examiner

COMPOUNDS AND METHODS FOR THE TREATMENT OF VIRUSES AND CANCER

RELATED APPLICATIONS

This application claims the benefit of priority of U.S. provisional application Ser. No. 60/720,307, filed Sep. 23, 2005, provisional application No. U.S. 60/730,934 filed Oct. 27, 2005, provisional application no. U.S. 60/781,486, filed Mar. 9, 2006, provisional application No. 60/836,723, filed Aug. 10, 2006, and provisional application No. 60/842,901, filed Sep. 7, 2006, all of which applications are incorporated by reference in their entirety herein.

The invention of the present application was made through support of National Institutes of Health grans (AI44616, GM32136, GM35208, GM49551). Consequently, the United States government retains certain rights in the invention.

FIELD OF THE INVENTION

The present invention relates to novel compounds which may be used to treat viral infections and/or cancer. The present invention also relates to pharmaceutical compositions which comprise these compounds as well as methods for treating viral infections or cancer.

BACKGROUND OF THE INVENTION

The AIDS crisis continues with ca. 40 million people infected by HIV-1, and 3 million deaths in 2004. *AIDS Epidemic Update: December* 2004: UNAIDS: Geneva, 2005. The therapeutic situation is challenged by rapid mutation of the virus to yield resistant strains. Anti-HIV drugs are normally given in combination, typically two nucleoside inhibitors of HIV-1 reverse transcriptase (NRTIs) and either a HIV protease inhibitor (PI) or a non-nucleoside RT inhibitor (NNRTI). *HIV Medicine* 2005; Hoffmann, C, Kamps, B. S., Eds.; Flying Publisher Paris, 2005. Long-term solutions include a vaccine, however, for those already infected, the current drugs do not systemically eliminate the virus, so they must be taken chronically. Many of the drugs require high dosages, which leads to compliance difficulties and costs that are only manageable in affluent nations. Patients often migrate among combinations, and long-term use of NRTIs and PIs can yield morphologic and metabolic complications including wasting and lipodystrophy. Pauwels, R. *Curr. Opin. Pharmacol.* 2004, 4, 437-446. The needs for new drugs and points of attack on HIV are profound. New drugs are expected to show enhanced activity against at least parts of the current spectrum of mutants.

Efforts have been aimed at the design of new NNRTIs. Three compounds in this class, nevirapine, delavirdine, and efavirenz, were approved by the FDA during 1996-1998. The first two succumb to many single point mutations in RT, and delavirdine is further debilitated by a high pill burden (400 mg bid). Efavirenz has an improved resistance profile and dosing (600 mg qd), though resistance still arises from common mutations including K103N and Y188L, and neurological side effects including dizziness and nightmares are frequent. Several NNRTIs with further improved resistance profiles such as DPC083, HBY097, and S-1153 (capravirine) stalled in clinical trials, while TMC125 (etravirine) continues on in spite of high dosage (900 mg bid).[3]

Thus, there is much room for improvement, and we have pursued computer-aided design of new NNRTIs with simultaneous goals of enhanced performance against common RT mutants, high bioavailability, and facile synthesis. The approach features lead generation with the growing program BOMB, property prediction with QikProp, and assistance in lead optimization with Monte Carlo simulations using free-energy perturbation theory (MC/FEP). The present invention emanates from the results of that work.

BRIEF DESCRIPTION OF THE INVENTION

The present invention relates to compounds according to the formula I:

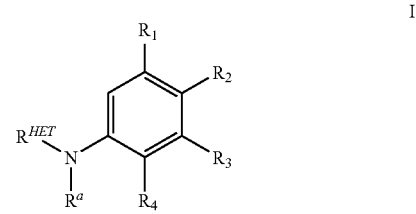

Where $R^a$ is H or an optionally OH-substituted $C_1$-$C_3$ alkyl; $R_1$ is $OR^1$, an optionally substituted $C_4$-$C_{12}$ carbocyclic group which may be saturated or unsaturated (including aromatic) or an optionally substituted heterocyclic group, preferably an optionally substituted 5-14 membered heterocyclic group, which may be monocyclic or a fused ring system having two or three rings (preferably, an optionally substituted heteroaromatic group, preferably an optionally substituted furanyl, pyrrolyl, thienyl, thiazoyl, pyridinyl, triazinyl, pyridazinyl, pyrimidinyl, pyrazinyl, triazolyl, oxazolyl, more preferably, an optionally substituted 2-furanyl, 3-furanyl, 3-pyrrolyl, 2-thienyl, 3-thienyl, 2-thiazolyl, 3-pyridinyl, 4-pyridinyl, 4-1,2,3(1H)-triazolyl, 2-pyrazinyl, indole, benzofuran, pyrrolopyrimidine, quinoline), which, where substituted, are preferably substituted by at one or two groups which are each independently selected from the group consisting of halogen, CN, $C_1$-$C_3$ alkyl, $CF_3$, OH, O—($C_1$-$C_3$ alkyl), $NH_2$, NH($C_1$-$C_2$ alkyl), N-di($C_1$-$C_2$ alkyl), S($C_1$-$C_3$ alkyl) and $NO_2$);

$R^1$ is an optionally substituted $C_1$-$C_{14}$ hydrocarbyl group, preferably a $C_1$-$C_6$ hydrocarbyl group, the hydrocarbyl group preferably containing at least one double bond, more preferably one double bond, or an optionally substituted heterocyclic group, preferably an optionally substituted 5 to 14 membered heterocyclic group which may be monocyclic or a fused ring system having two or three rings (preferably, an optionally substituted heteroaromatic group, preferably an optionally substituted furanyl pyrrolyl, thienyl, thiazoyl, pyridinyl, triazinyl, pyridazinyl, pyrimidinyl, pyrazinyl, triazolyl, oxazolyl, more preferably, an optionally substituted 2-furanyl, 3-furanyl, 3-pyrrolyl, 2-thienyl, 3-thienyl, 2-thiazolyl, 3-pyridinyl, 4-pyridinyl, 4-1,2,3(1H)-triazolyl, 2-pyrazinyl which, where substituted, are preferably substituted by one or two groups which are each independently selected from the group consisting of halogen, CN, an optionally substituted $C_1$-$C_3$ alkyl, $CF_3$, OH, O($C_1$-$C_3$ alkyl), $NH_2$, NH($C_1$-$C_2$ alkyl), N-di($C_1$-$C_2$ alkyl), S($C_1$-$C_3$ alkyl) and $NO_2$);

$R_2$, $R_3$ and $R_4$ are each independently H, an optionally substituted $C_1$-$C_4$ alkyl group (preferably $CH_3$, $CH_2CH_3$ or $CF_3$), halogen (preferably F, Cl, Br), OR, CN, $NO_2$, a $C_1$-$C_6$ thioether, a $C_1$-$C_6$ thioester group, an optionally substituted $CO_2R$ group, an optionally substituted COR group or an optionally substituted OCOR group (preferably $R_4$ is H);

R is H or an optionally substituted $C_1$-$C_6$ alkyl group;

$R^{HET}$ is an optionally substituted heterocyclic group, preferably an optionally substituted 5-14 membered heterocyclic group, which may be monocyclic or a fused ring system having two or three rings, preferably an optionally substituted heteroaromatic group selected from the group consisting of an optionally substituted furanyl, pyrrolyl, thienyl, thiazoyl, pyridinyl, triazinyl, pyridazinyl, pyrimidinyl, pyrazinyl, triazolyl, oxazolyl, more preferably, an optionally substituted 2-furanyl, 3-furanyl, 3-pyrrolyl, 2-thienyl, 3-thienyl, 2-thiazolyl, 2-pyridinayl, 4-pyridinyl, 4-1,2,3(1H)-triazolyl and 2-pyrazinyl, (preferably an optionally substituted 2-pyrimidinyl group, an optionally substituted 2-(1,3,5)-triazinyl group, an optionally substituted 2-thiazolyl group, or an optionally substituted 2-oxazolyl group, an optionally substituted indole, benzofuran, pyrrolopyrimidine, pyrrolopyrazine, furopyrimidine or quinoline group (all optionally substituted), which, where substituted, are preferably substituted by one, two or three groups which are each independently selected from the group consisting of halogen, CN, optionally substituted $C_1$-$C_3$ alkyl, $CF_3$, OH, O($C_1$-$C_3$ alkyl), $NH_2$, NH($C_1$-$C_2$ alkyl), N-di($C_1$-$C_2$ alkyl), S($C_1$-$C_3$ alkyl) and $NO_2$;

and pharmaceutically acceptable salts, solvates or polymorphs thereof.

Preferred compounds according to the present invention are depicted by the formula II:

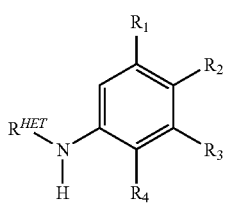

where $R_1$ is 3,3-dimethylallyloxy, 2-furanylmethoxy, 3-furanylmethoxy, 2-thienylmethoxy, 2-thiazolylmethoxy, 3-pyrollylmethyl, 3-pyrollylmethoxy, N-methyl-3-pyrrolylmethyl, N-methyl-3-pyrrolylmethoxy, cyclopent-1-enylmethoxy, 2-methyl-cyclopent-1-enylmethoxy, phenoxy, benzyloxy, cyclpentyloxy and cyclohexyloxy, each of which is optionally substituted with one or two groups selected from the group consisting of F, Cl, Br, I; CN, Me, Et, $CF_3$, OMe, Me, OEt, OH, $CH_2OH$, $NH_2$, NHMe, SMe and $NO_2$;

$R_2$ is H, F, Cl, Br, I, CN, Me, Et, $CF_3$, OMe, OEt, SMe, COOH, $CH_2OMe$ or COOMe, preferably Cl or CN;

$R_3$ is H, F, Cl, Br, I, CN, Me, Et, $CF_3$, OMe or SMe;

$R_4$ is H; and $R^{HET}$ is

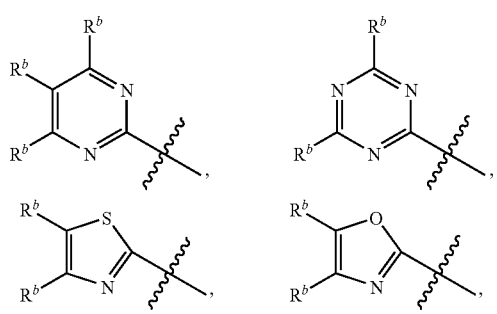

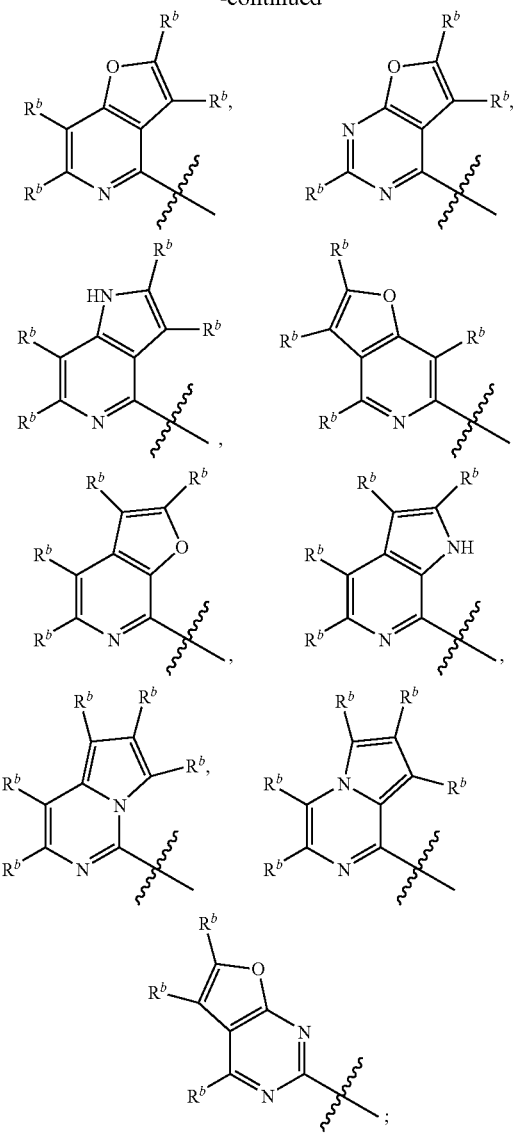

Where each $R^b$ is independently H, F, Cl, Br, I, CN, Me, Et, $CF_3$, OMe, OEt, OH, $CH_2OH$, $CH_2OMe$, $NH_2$, NHMe, SMe or $NO_2$; and pharmaceutically acceptable salts, solvates and polymorphs thereof.

In another embodiment according to the present invention, pharmaceutical compositions comprise an effective amount of one or more compounds as described above, optionally in combination with a pharmaceutically acceptable carrier, excipient or additive.

Thus, the present application is directed to the treatment of disease states or conditions including various mammalian or avian viral infections, especially human viruses, including human immunodeficiency virus (HIV) infections (HIV I and/or II) or conditions associated with such infections (AIDS), Hepatitis A Virus (HAV), Hepatitis B virus (HBV) and Hepatitis C virus (HCV) infections, Human T-cell Leukemia virus (HTLV I and II), Herpes Simplex virus infections (HSV I and II), especially including drug resistant forms of each of these viruses, other viral infections or diseases including drug resistant forms of these viruses, for example, respiratory syncytial virus (RSV), human papilloma virus (HPV), adenovirus, Epstein-Barr virus (EBV), varicella zoster virus (VZV), cytomegalovirus (CMV), human herpes virus 8 (HHV-8, also known as Kaposi's sarcoma-associated virus) and viruses of the family, Flaviviridae, including flaviriruses and pestivixuses including Yellow Fever virus, Dengue virus, Japanese Encephalitis and West Nile viruses, among others, tumors and/or cancer, proliferative diseases including psoriasis, genital warts and hyperproliferative keratinocyte diseases including hyperkeratosis, ichthyosis, keratoderma, and lichen planus, said method comprising administering to a patient in need thereof an effective amount of a pharmaceutical composition comprising any one or more of the compounds previously described above.

DETAILED DESCRIPTION OF THE INVENTION

The following definitions shall be used to describe the present invention. Unless otherwise indicated, terms used to describe the present invention are given their ordinary meaning within the context of their use as understood by those of ordinary skill in the art.

"Patient" refers to an animal, preferably a mammal, even more preferably a human, in need of treatment or therapy to which compounds according to the present invention are administered in order to treat a condition or disease state treatable using compounds according to the present invention.

The term "compound" is used herein to refer to any specific chemical compound disclosed herein. Within its use in context, the term generally refers to a single compound, but in certain instances may also refer to stereoisomers and other positional isomers and/or optical isomers (including racemic mixtures) of disclosed compounds. The compounds of this invention include all stereoisomers where relevant (e.g., cis and trans isomers) and all optical isomers of the present compounds (eg., R and S enantiomers), as well as racemic, diastereomeric and other mixtures of such isomers, as well as all polymorphs and solvates, including hydrates of the present compounds, where applicable.

"Hydrocarbon" or "hydrocarbyl" refers to any monovalent radical containing carbon and hydrogen, which may be straight, branch-chained or cyclic in nature. Hydrocarbons include linear, branched and cyclic hydrocarbons, including alkyl groups, alkylene groups, saturated and unsaturated hydrocarbon groups, including aromatic groups both substituted and unsubstituted.

"Alkyl" refers to a fully saturated monovalent radical containing carbon and hydrogen, and which may be cyclic, branched or a straight chain. Examples of alkyl groups are methyl, ethyl, n-butyl, n-hexyl, n-heptyl, n-octyl, isopropyl, 2-methylpropyl, cyclopropyl, cyclopropylmethyl, cyclobutyl, cyclopentyl, cyclopentylethyl, cyclohexylethyl and cyclohexyl. Preferred alkyl groups are $C_1$-$C_6$ alkyl groups. "Alkylene" refers to a fully saturated hydrocarbon which is divalent (may be linear, branched or cyclic) and which is optionally substituted. Other terms used to indicate substitutent groups in compounds according to the present invention are as conventionally used in the art.

The term "5- to 14-membered heterocyclic group" as used throughout the present specification refers to an aromatic or non-aromatic cyclic group having 5 to 14 atoms forming the cyclic ring(s) and including at least one hetero atom such as nitrogen, sulfur or oxygen among the atoms forming the cyclic ring, which is a "5- to 14-membered aromatic heterocyclic group" (also, "heteroaryl" or "heteroaromatic") in the former case and a "5- to 14-membered non-aromatic heterocyclic group" in the latter case. Specific examples of the "5- to 14-membered heterocyclic group" therefore include specific examples of the "5- to 14-membered aromatic heterocyclic group" and specific examples of the "5- to 14-membered non-aromatic heterocyclic group", as otherwise described herein. Among the heterocyclic groups which may be mentioned include nitrogen-containing aromatic heterocycles such as pyrrole, pyridine, pyridone, pyridazine, pyrimidine, pyrazine, pyrazole, imidazole, triazole, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole. As examples of the "5- to 14-membered aromatic heterocyclic group" there may be mentioned preferably, pyridine, triazine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzthiazole, phenothiazine, pyrrolopyrimidine, furopyridine and thienopyrimidine, more preferably pyridine, thiophene, benzothiophene, thiazole, benzothiazole, quinoline, quinazoline, cinnoline, pyrrolopyrimidine, pyrimidine, furopyridine and thienopyrimidine. The term "heterocyclic group" shall generally refer to 3 to 14-membered heterocyclic groups and all subsets of heterocyclic groups (including non-heteroaromatic or heteroaromatic) subsumed under the definition of heterocyclic group are 3 to 14-membered heterocyclic groups.

The term "8 to 14-membered heterocyclic group" refers to an aromatic or non-aromatic fused bicyclic or tricyclic group having 8 to 14 atoms forming the cyclic rings (two or three rings) and include at least one hetero atom such as nitrogen, sulfur or oxygen among the atoms forming the cyclic rings, which is a "8- to 14-membered aromatic heterocyclic group" (also, "heteroaryl" or "heteroaromatic") in the former case and a "8- to 14-membered non-aromatic heterocyclic group" in the latter case. "8 to 14 membered heterocyclic groups" are represented by fused bicyclic and tricyclic ring structures containing nitrogen atoms such as indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, benzimidazole, pyrrolopyridine, pyrrolopyrimidine and pyridopyrimidine; sulfur-containing aromatic heterocycles such as thiophene and benzothiophene; oxygen-containing aromatic heterocycles such as cyclopentapyran, benzofuran and isobenzofuran; and aromatic heterocycles comprising 2 or more hetero atoms selected from among nitrogen, sulfur and oxygen, such as benzoxazole, benzothiazole, benzothiadiazole, phenothiazine, benzofurazan, phenoxazine, pyrazoloxazole, imidazothiazole, thienofuran, furopyrrole, pyridoxazine, furopyridine, furopyrimidine and thienopyrimidine, among others.

The term "5- to 14-membered non-aromatic heterocyclic group" as used throughout the present specification refers to a non-aromatic cyclic group having 5 to 14 atoms forming the cyclic ring and including at least one hetero atom such as nitrogen, sulfur or oxygen among the atoms forming the cyclic ring. As specific examples there may be mentioned non-aromatic heterocycles such as pyrrolidinyl, pyrrolinyl, piperidinyl, piperazinyl, N-methylpiperazinyl, imidazolinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3-dioxolane, 1,3-dioxane, 1,4-dioxane, phthalimide and succinimide. As examples of the "5- to 14-membered non-aromatic heterocyclic group" there may be mentioned preferably, pyrrolidinyl, piperidinyl and morpholinyl, and more preferably pyrrolidinyl, piperidinyl, morpholinyl and pyrrole.

The term "8- to 14-membered non-aromatic heterocyclic group" as used throughout the present specification refers to a non-aromatic fused cyclic ring system (generally with two or three rings) having 8 to 14 atoms forming the cyclic rings (bicyclic or tricyclic) and including at least one hetero atom such as nitrogen, sulfur or oxygen among the atoms forming the cyclic rings.

The term "5- to 14-membered heterocyclic group" as used throughout the present specification refers to an aromatic or non-aromatic cyclic group having 5 to 14 atoms forming the cyclic ring and including at least one hetero atom such as nitrogen, sulfur or oxygen among the atoms forming the cyclic ring, which is a "5- to 14-membered aromatic heterocyclic group" in the former case and a "5- to 14-membered non-aromatic heterocyclic group" in the latter case. Specific examples of the "5- to 14-membered heterocyclic group" therefore include specific examples of the "5- to 14-membered aromatic heterocyclic group" and specific examples of the "5- to 14-membered non-aromatic heterocyclic group".

As the "5- to 14-membered heterocyclic group" there may be mentioned preferably pyrrolidinyl, piperidinyl, morpholinyl, pyrrole, pyridine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzothiazole, phenothiazine and carbostyryl, more preferably pyrrolidinyl, piperidinyl, morpholinyl, pyrrole, pyridine, thiophene, benzothiophene, thiazole, benzothiazole, quinoline, quinazoline, cinnoline and carbostyryl, and even more preferably thiazole, quinoline, quinazoline, cinnoline and carbostyryl, among others.

The term "6- to 14-membered aromatic heterocyclic group" as used throughout the present specification refers to those substituents defined by "5- to 14-membered aromatic heterocyclic group" which have 6 to 14 atoms forming the cyclic ring. As specific examples there may be mentioned pyridine, pyridone, pyrimidine, indole, quinoline, isoquinoline, quinolizine, phthalazine, naphthyridine, quinazoline, cinnoline, acridine, benzothiophene, benzofuran, thiazole, benzothiazole and phenothiazine*. "8 to 14-membered aromatic heterocyclic groups" refer to those substituents or radicals having 8 to 14 atoms forming fused two or three cyclic ring systems. Specific examples include indole, quinoline, isoquinoline, quinolizine, phthalazine, naphthyridine, quinazoline, cinnoline, acridine, benzothiophene, benzofuran, benzothiazole, pyrrolopyrimidine, pyrrolopyrazine, furopyrimidine and phenothiazine, among numerous others.

The term "6- to 14-membered heterocyclic group" as used throughout the present specification refers to those substituents defined by "5- to 14-membered heterocyclic group" which have 6 to 14 atoms forming the cyclic ring(s). As specific examples there may be mentioned piperidinyl, piperazinyl, N-methylpiperazinyl, morpholinyl, tetrahydropyranyl, 1,4-dioxane and phthalimide.

The term "3 to 7-membered heterocyclic group" as used throughout the present specification refers to those heterocyclic substituents which have 3 to 7 atoms forming the cyclic ring, preferably 5 to 6 atoms forming the cyclic ring.

The term "8 to 14-membered heterocyclic group" as used throughout the present specification refers to those substituents defined "8- to 14-membered heterocyclic groups which have 8 to 14 atoms forming the fused cyclic ring system.

"Aryl" or "aromatic", in context, refers to a substituted or unsubstituted monovalent aromatic radical having a single ring (e.g., benzene) or multiple condensed rings (e.g., naphthyl, anthracenyl, phenanthryl) and can be can be bound to the compound according to the present invention at any position on the ring(s). Other examples of aryl groups, in context, may include heterocyclic aromatic ring systems "heteroaryl" groups having one or more nitrogen, oxygen, or sulfur atoms in the ring (moncyclic) such as imidazole, furyl, pyrrole, pyridyl, furanyl, thiene, thiazole, pyridine, pyrimidine, pyrazine, triazole, oxazole, indole or fused ring systems (bicyclic, tricyclic), among others, which may be substituted or unsubstituted as otherwise described herein.

The term "cyclic" shall refer to an optionally substituted carbocyclic or heterocyclic group, preferably a 5- or 6-membered ring or fused rings (two or three rings) preferably containing from 8 to 14 atoms. A heterocyclic ring or group shall contain at least one monocyclic ring containing between 3 and 7 atoms of which up to four of those atoms are other than carbon and are selected from nitrogen, sulfur and oxygen. Carbocyclic and heterocyclic rings according to the present invention may be unsaturated or saturated. Preferred heterocyclic groups are heteroaryl or heteroaromatic.

The term "effective amount" refers to the amount of a selected compound which is effective within the context of its use or administration. In the case of therapeutic methods according to the present invention, the precise amount required will vary depending upon the particular compound selected, the age and weight of the subject, route of administration, and so forth, but may be easily determined by routine experimentation. Compounds according to the present invention may be used to treat or prevent viral infections (by for example, inhibition the growth, replication or elaboration of the virus). In addition, compounds according to the present invention may be used to treat tumors and/or cancer, proliferative diseases including psoriasis, genital warts and hyperproliferative keratinocyte diseases including hyperkeratosis, ichthyosis, keratoderma and lichen planus, all at effective amounts.

The term "substituted" shall mean substituted at a carbon (or nitrogen) position within context, hydroxyl, carboxyl, cyano (C═N), nitro ($NO_2$), halogen (preferably, 1, 2 or 3 halogens, especially on an alkyl, especially a methyl group such as a trifluoromethyl), thiol, alkyl group (preferably, $C_1$-$C_6$, more preferably, $C_1$-$C_3$), alkoxy group (preferably, $C_1$-$C_6$ alkyl or aryl, including phenyl), ester (preferably, $C_1$-$C_6$ alkyl or aryl) including alkylene ester (such that attachment is on the alkylene group, rather than at the ester function which is preferably substituted with a $C_1$-$C_6$ alkyl or aryl group), thioether (preferably, $C_1$-$C_6$ alkyl or aryl), thioester (preferably, $C_1$-$C_6$ alkyl or aryl), (preferably, $C_1$-$C_6$ alkyl or aryl), halogen (F, Cl, Br, I), nitro or amine (including a five- or six-membered cyclic alkylene amine, including a $C_1$-$C_6$ alkyl amine or $C_1$-$C_6$ dialkyl amine), alkanol (preferably, $C_1$-$C_6$ alkyl or aryl), or alkanoic acid (preferably, $C_1$-$C_6$ alkyl or aryl). Preferably, the term "substituted" shall mean within its context of use alkyl, alkoxy, halogen, hydroxyl, carboxylic acid, nitro and amine (including mono- or di-alkyl substituted amines). Any substitutable position in a compound according to the present invention may be substituted in the present invention, but preferably no more than 5, more preferably no more than 3 substituents are present on a single ring or ring system. Preferably, the term "unsubstituted" shall mean substituted with one or more H atoms.

The term "virus" shall be used to describe all types of viruses, the growth or replication of which may be inhibited or disease states of which may be treated using one or more methods according to the present invention. Viruses which may be treated according to the present invention include, for example, human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and viruses of the family Flaviviridae, which includes flaviriruses and pestiviruses including Yellow Fever virus, Dengue virus, Japanese Encephalitis and West Nile viruses, among numerous others.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Representative cancers include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention.

The term "tumor" is used to describe a malignant or benign growth or tumefacent.

The term "hyperproliferative disease state" refers to a disease state in which cells are growing in an uncontrolled manner, whether that growth is cancerous or not. Such a disease state may be reflected in psoriasis, genital warts or other hyperproliferative cell growth diseases, including hyperproliferative keratinocyte diseases including hyperkeratosis, ichthyosis, keratoderma or lichen planus, all of which disease states may be treated using compounds according to the present invention.

The term "pharmaceutically acceptable" refers to a carrier, additive or excipient which is not unacceptably toxic to the subject to which it is administered. Pharmaceutically acceptable excipients are described at length by E. W. Martin, in "Remington's Pharmaceutical Sciences", among others well-known in the art.

A "pharmaceutically acceptable salt" of the present compound generally refers to pharmaceutically acceptable salts form of a compound which can form a salt, because of the existence of for example, amine groups, carboxylic acid groups or other groups which can be ionized in a sample acid-base reaction. A pharmaceutically acceptable salt of an amine compound, such as those contemplated in the current invention, include, for example, ammonium salts having as counterion an inorganic anion such as chloride, bromide, iodide, sulfate, sulfite, nitrate, nitrite, phosphate, and the like, or an organic anion such as acetate, malonate, pyruvate, propionate, fumarate, cinnamate, tosylate, and the like. Certain compounds according to the present invention which have carboxylic acid groups or other acidic groups which may form pharmaceutically acceptable salts, for example, as carboxylate salts, are also contemplated by the present invention.

Aspects of the present invention include compounds which have been described in detail hereinabove or to pharmaceutical compositions which comprise an effective amount of one or more compounds according to the present invention, optionally in combination with a pharmaceutically acceptable carrier, additive or excipient.

The term "pharmaceutically acceptable derivative" is used throughout the specification to describe any pharmaceutically acceptable prodrug form (such as an ester or ether or other prodrug group) which, upon administration to a patient, provides directly or indirectly the present compound or an active metabolite of the present compound.

The term "inhibitory effective concentration" or "inhibitory effective amount" is used throughout the specification to describe concentrations or amounts of compounds according to the present invention which substantially or significantly inhibit the growth or replication of susceptible viruses, especially including human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and viruses of the family Flaviviridae, including flaviviruses, such as Yellow Fever virus, Dengue virus, Japanese Encephalitis and West Nile viruses, among numerous others.

The term "preventing effective amount" is used throughout the specification to describe concentrations or amounts of compounds according to the present invention which are prophylactically effective in preventing, reducing the likelihood of infection or delaying the onset of infections in patients caused by human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and viruses of the family Flaviviridae, including flaviviruses, such as Yellow Fever virus, Dengue virus, Japanese Encephalitis and West Nile viruses, among numerous others. The terms inhibitory effective amount or preventive effective amount also generally fall under the rubric "effective amount".

The term "coadministration" or "combination therapy" is used to describe a therapy in which at least two active compounds in effective amounts are used to treat a viral infection at the same time. Although the term coadministration preferably includes the administration of two active compounds to the patient at the same time, it is not necessary that the compounds be administered to the patient at the same time, although effective amounts of the individual compounds will be present in the patient at the same time. Compounds according to the present invention may be administered with one or more anti-viral agent, including other anti-HIV agents including nucleoside reverse transcriptase inhibitors (NRTI), other non-nucloeoside reverse transcriptase inhibitors, protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development. Coadministration also embraces the administration of dual analogs (i.e., compounds wherein at least two biologically active compounds are chemically linked via a chemical linker such as, for example, without limitation, phosphate groups or carboxylate groups, among others) or other dual antagonists, where at least one of the active compounds of the dual antagonist compound is a compound as otherwise described herein.

In the case of treating tumors and/or cancer or one or more hyperprolifeative diseases as otherwise discussed herein, coadministration may be with one or more anti-cancer agent such antimetabolites, Ara C, etoposide, doxorubicin, taxol, hydroxyurea, vincristine, cytoxan (cyclophosphamide), methotrexate, or mitomycin C, among numerous others, including topoisomerase I and topoisomerase II inhibitors, such as adriamycin, topotecan, campothecin and irinotecan, other agent such as gemcitabine and agents based upon campothecin and cis-platin may be included. These compounds may also be included in pharmaceutical formulations or coadministered with compounds according to the present invention to produce additive or synergistic anti-cancer activity. Exemplary anti-cancer compounds which may be used for co-administration with compounds according to the present invention in the treatment of cancer include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valnibicin; valtorcitabine (monoval LDC); vinblastine; vinorelbine; zoledronate; and mixtures thereof, among others.

Compounds according to the present invention may be used in pharmaceutical compositions having biological/pharmacological activity for the treatment of, for example, viral infections, as well as a number of other conditions and/or disease states which may appear or occur secondary to the viral infection. These compositions comprise an effective amount of any one or more of the compounds disclosed hereinabove, optionally in combination with a pharmaceutically acceptable additive, carrier or excipient. Compounds according to the present invention may also be used as intermediates in the synthesis of compounds exhibiting biological activity as well as standards for determining the biological activity of the present compounds as well as other biologically active compounds.

The compositions of the present invention may be formulated in a conventional manner using one or more pharmaceutically acceptable carriers. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound of the instant invention that may be combined with the carrier materials to produce a single dosage form will vary depending upon the host treated, the particular mode of administration. Preferably, the compositions should be formulated so that a dosage of between about 0.01 and 150, preferably about 0.5 to about 25 mg/kg of patient/day of the novel compound can be administered to a patient receiving these compositions.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.25 milligram to about 1 gram, more preferably about 1 milligram to about 750 milligrams, and even more preferably about 10 milligrams to about 500-600 milligrams of active ingredient.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

In particularly preferred embodiments according to the present invention, the compounds and compositions are used to treat, prevent or delay the onset of viral infections of mammals and in particular HIV, HBV, HSV1 and/or II, EBV, HHV-8 and flavivirus infections, among others. In its preferred embodiments, the compounds are used to treat HIV, HSV I and/or II, HBV, EBV or HHV-8 infections, especially HIV infections in humans. Preferably, to treat, prevent or delay the onset of a viral infection, the compositions will be administered in oral dosage form in amounts ranging from about 250 micrograms up to about 500 mg or more at least once a day, preferably, up to four times a day, within the dosage range used for therapeutic treatment. The present compounds are preferably administered orally, but may be administered parenterally, topically, in suppository or other form.

In the case of treating cancer or hyperproliferative disease, the compositions should be formulated to contain between about 0.5 milligram to about 1 gram, more preferably about 1 milligram to about 750 milligrams, and even more preferably about 10 milligrams to about 500-600 milligrams of active ingredient.

The compounds according to the present invention, because of their low toxicity to host cells, may advantageously be employed prophylactically to prevent a viral infection or to prevent the occurrence of clinical symptoms associated with the viral infection, for example AIDS secondary to HIV, lymphoma secondary to EBV or Kaposi's sarcoma secondary to HHV-8. Thus, the present invention also encompasses methods for the prophylactic treatment (preventing, reducing the likelihood or delaying the onset) of viral infections, and in particular HIV and EBV and in particular, conditions which occur secondary to those viruses. In this aspect according to the present invention, the present compositions are used to prevent reduce the likelihood of or delay the onset of a viral infection, in particular, HIV, HSV, EBV or another virus infection or a virus related disease or condition such as AIDS or EBV-related lymphoma or Kaposi's sarcoma (HHV-8). This prophylactic method comprises administering to a patient in need of such treatment or who is at risk for the development of an HIV, EBV, HHV-8 or other viral infection, an amount of a compound according to the present invention effective for alleviating, preventing or delaying the onset of the viral infection. In the prophylactic treatment according to the present invention, it is preferred that the antiviral compound utilized should be as low in toxicity and preferably non-toxic to the patient. It is particularly preferred in this aspect of the present invention that the compound which is used should be maximally effective against the virus and should exhibit a minimum of toxicity to the patient. In the case of compounds of the present invention for the prophylactic treatment of viral infections, these compounds may be administered within the same dosage range for therapeutic treatment (as described hereinabove, as a prophylactic agent to prevent the proliferation of the viral infection or alternatively, to prolong the onset of or reduce the likelihood of a patient contracting a virus infection which manifests itself in clinical symptoms.

In addition, compounds according to the present invention may be administered alone or in combination with other agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

As indicated, compounds according to the present invention may be administered alone or in combination with other anti-viral agents for the treatment of a virus infection as otherwise described herein, especially including other compounds of the present invention or compounds which are otherwise disclosed as being useful for the treatment of HIV or flaviviruses, including those presently used to treat HIV such as nucleoside reverse transcriptase inhibitors (NRTI), other non-nucleoeoside reverse transcriptase inhibitors, protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-D4FC, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development, among others as well as compounds which are disclosed in inter alia, U.S. Pat. Nos. 6,240,690; 6,316,505; 6,316,492; 6,232,120; 6,180,604; 6,114,327; 5,891,874; 5,821,242; 5,532,215; 5,491,135; 5,179,084; and 4,880,784, among others, relevant portions of which are incorporated by reference herein.

The compounds disclosed in the above-referenced patents may be used in combination with the present compounds for their additive activity or treatment profile against HIV and/or other viruses and in certain instances, for their synergistic effects in combination with compounds of the present invention. Preferred secondary or additional compounds for use with the present compounds are those which do not inhibit HIV or another virus. Certain compounds according to the present invention may be effective for enhancing the biological activity of certain agents according to the present invention by reducing the metabolism or inactivation of other compounds and as such, are co-administered for this intended effect.

Compounds according to the present invention may be used as active agents in pharmaceutical compositions as inhibitors of reverse transcriptase and as anti-viral agents, said compositions comprising an effective amount of one or more of the compounds disclosed above, formulated as a pharmaceutical dosage form, optionally in combination with a pharmaceutically acceptable carrier, additive or excipient. Pharmaceutical compositions according to the present invention may be used in the treatment of cancer, proliferative diseases including, for example, psoriasis, genital warts and hyperproliferative keratinocyte diseases including hyperkeratosis, ichthyosis, keratoderma or lichen planus, HIV infections (all forms, including human immunodeficiency virus I and II), Herpes simplex virus infections (HSV, including HSV I and HSV II), hepatitis infections, including hepatitis B virus infections (HBV infections) and hepatitis C infections (HCV infections), and numerous additional viral infections other than HIV, HSV or HBV, as described herein, including drug resistant forms of these viruses.

In other aspects of the present invention, certain compounds according to the present invention may be used as antagonists in binding assays, as analytical agents, as agents to be used to isolate or purify proteins (especially viral reverse transcriptase), and/or as intermediates in the synthesis of further agents, among other uses.

General Chemistry for Producing Compositions According to the Present Invention

Exemplary Chemistry Thiazoles

The preparation of the analogues 4a-h involved the reaction between 2-bromothiazole 1 with the corresponding 5-amino-2-R-phenol 2, followed by reaction with 4-bromo-2-methyl-2-butene in presence of $Cs_2CO_3$ as a base (Scheme 1; see Table 1 for antiviral activities (EC50) and cytotoxicities (IC50) of these compounds, as determined using human MT-2 cells infected with IIIB strain of HIV-1).

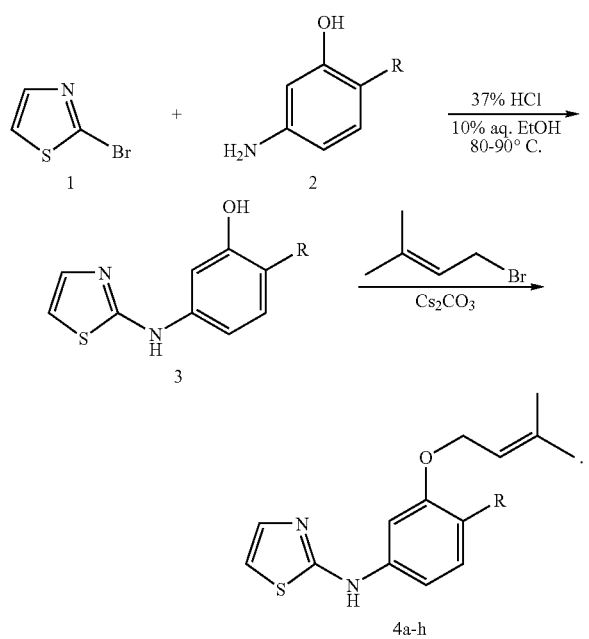

Scheme 1. General synthesis for analogues 4a-h

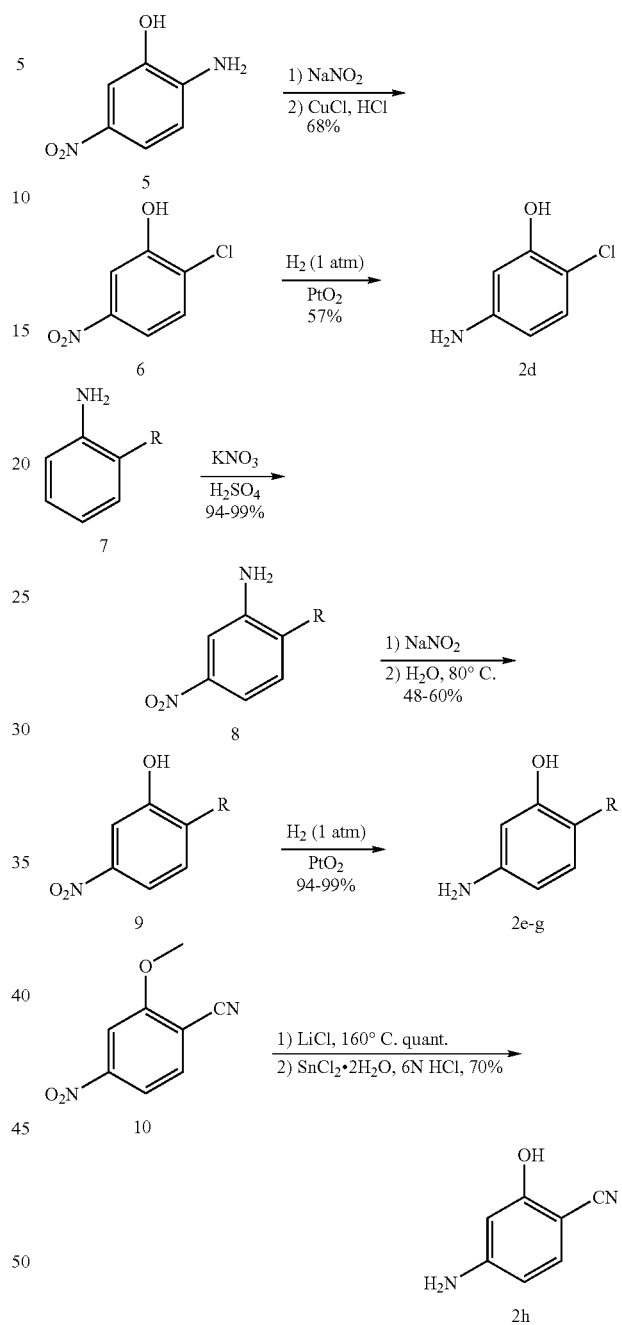

Scheme 2. Synthesis of anilines 2d-2h.

5-Amino-2-chlorophenol[1] 2d was synthesized from 2-amino-5-nitrophenol 5 in two steps: 1) formation of the diazonium salt with $NaNO_2$ and reaction with CuCl to give the corresponding 2-chloro-5-nitrophenol 6 in 68% yield and 2) careful reduction of the nitro group with $H_2$ (1 atm) in presence of Adam's catalyst to give the final amine derivative in 57% yield (Scheme 2).

[1] a) Sato, K.; Tsukase, M.; Shibata, T. Eur. Pat. Appl. (1986), 97 pp. CODEN: EPXXIDW EP 205983 86-107355 19860530. b) Tixier, C.; Sancelme, M.; Bonnemey, F.; Cuer, A.; Veschambre, H. *Environ. Toxicol. Chem.* 2001, 20, 1381.

5-Amino-2-ethyl/n-propyl/i-propylphenol 2e-g was synthesized in four steps from the corresponding 2-ethyl/n-propyl/i-propylaniline 7e-g. The first step was nitration with potassium nitrate in presence of sulfuric acid to give exclusively the corresponding 5-nitro-2-alkylaniline[2] 8e-g; reaction with $NaNO_2$, followed by reaction with $H_2O$ at 80° C. for 2 h gave the corresponding 5-nitro-2-alkylphenol derivatives[3] 9e-g and finally, hydrogenation of the nitro group gave the corresponding amine derivatives 2e-g (Scheme 2).

[2] Elzbieta, D.; Zygmunt, E. *Przemysl Chemiczny* 1963, 42, 433.
[3] Gaster, L. M.; King, F. D.; Wyanan, P. A. PCT Int. Appl. 1995, 63 pp. CODEN: PIXXD2 WO 9515954 A1 19950615.

2-Amine-4-hydroxybenzonitrile[4] 2h was obtained from 2-methoxy-4-nitrobenzonitrile 10 by hydrolisis of the methyl ether with LiCl and posterior, reduction of the nitro group with $SnCl_2.2H_2O$ in presence of 6N HCl (Scheme 2).

[4] Imakura, Y.; Okimoto, K.; Tonishi, T.; Hisazumi, M.; Yamazaki, *J. Chem. Pharm. Bull.* 1992, 40, 1691.

TABLE 1

Biological activity for compounds 4a-h.

| compd | R | $EC_{50}(\mu M)$ | $IC_{50}(\mu M)$ |
|---|---|---|---|
| 4a | H | 10 | 23 |
| 4b | $CH_3$ | 3 | 17 |
| 4c | $OCH_3$ | 3.8 | 42 |
| 4d | Cl | 0.3 | 26 |
| 4e | $CH_2CH_3$ | 5 | 31 |
| 4f | $CH_2CH_2CH_3$ | N/A | 31 |
| 4g | $CH(CH_3)_2$ | 23 | 23 |
| 4h | CN | 0.21 | 0.75 |

Synthesis of 2-amino-4-R-thiazole derivatives 8-10

Thiourea derivative 5, which was formed by reaction of the corresponding amine analogue 2 with ammonium thiocyanate, was treated with α-bromoacetone or ethyl bromopiruvate to give the intermediates 6 or 7, respectively. O-Alkylation under standard conditions gave the final compounds 8 and 9. The reduction of the ethyl ester with LiAlH$_4$ gave the alcohol 10 (Scheme 3; see Table 2 for antiviral activities of these compounds).

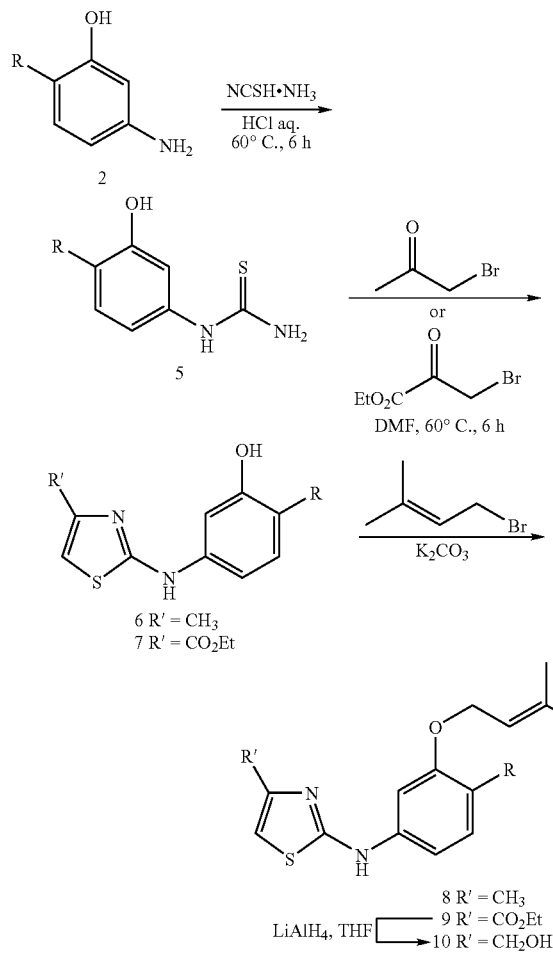

In general, the substitution in the C-4 position of thiazole showed a lack or reduced activity with respect to unsubstituted compounds (Table 2).

TABLE 2

Anti-HIV activity for compounds 8-10.

| comp | R' | R | EC$_{50}$(μM) | IC$_{50}$(μM) |
|---|---|---|---|---|
| 8a | CH$_3$ | H | N/A | 26 |
| 8b | CH$_3$ | CH$_3$ | N/A | 15 |
| 8c | CH$_3$ | OCH$_3$ | N/A | 18 |
| 9a | CO$_2$Et | H | N/A | 21 |
| 9b | CO$_2$Et | CH$_3$ | N/A | 11 |
| 9c | CO$_2$Et | OCH$_3$ | N/A | 15 |
| 10a | CH$_2$OH | H | N/A | 38 |

TABLE 2-continued

Anti-HIV activity for compounds 8-10.

| comp | R' | R | EC$_{50}$(μM) | IC$_{50}$(μM) |
|---|---|---|---|---|
| 10b | CH$_2$OH | CH$_3$ | 13 | 23 |
| 10c | CH$_2$OH | OCH$_3$ | 9 | 80 |

For the synthesis of compounds 11-23, two different methods were used.

Analogues 11-18 were synthesized by O-alkylation of 2-R-5-(thiazol-2-ylamino)phenol 3 with 2-furfuryl bromide[5] (generated in situ from furfuryl alcohol and PBr$_3$), furan-3-ylmethanol[6], 2-(bromomethyl)thiophene[7], 3-bromomethylthiophene[8], 2-(bromomethyl)-1,3-thiazole[9], benzyl bromide and 2-methylbenzyl bromide, respectively, in the presence of Cs$_2$CO$_3$ as a base. Analogues 19-23 were made by reaction of 2-R-5-(thiazol-2-ylamino)phenol 3 with (E/Z)-3-methylpent-2-en-1-ol[10], 4-methylpent-3-en-2-ol[11], 1-cyclopentene-1-methanol[12], (2-methylcyclopent-1-yl)methanol[13], cyclohexanol and n-hexanol using Mitsunobu conditions[14]. (Scheme 4; see Table 3 and Table 4 for antiviral activities of these compounds).

[5] Zanetti, J. E. *J. Am. Chem. Soc.* 1927, 49, 1065.
[6] Aggarwal, V. K.; Vasse, J.-L. *Org. Lett.* 2003, 5, 3987.
[7] Rossi, R.; Carpita, A.; Lippolis, V.; Benetti, M. *Gazz. Chim. Ital.* 1990, 120, 783.
[8] Mandal, S. S.; Chakraborty, J.; De, A. *J. Chem. Soc., Perkin Trans.* 1 1999, 2939.
[9] Dondoni, A.; Fantin, G.; Fogagnolo, M.; Medici, A.; Pedrini, P. *Tetrahedron* 1988, 44, 2021.
[10] Young, C. G.; James, B. R.; Rettig, S. J. *Can. J. Chem.* 1985, 63, 1035.
[11] Cain, M. E. *J. Chem. Soc.* 1964, 3532.
[12] Hager, D. C.; Bentrude, W. G. *J. Org. Chem.* 2000, 65, 2786.
[13] a) Harding, K. E.; Clement, K. S. *J. Org. Chem.* 1984, 49, 2049. b) Lemieux, R. M.; Meyers, A. I. *J. Am. Chem. Soc.* 1998, 120, 5453.
[14] Lepore, S. D.; He, Y. *J. Org. Chem.* 2003, 68, 8261.

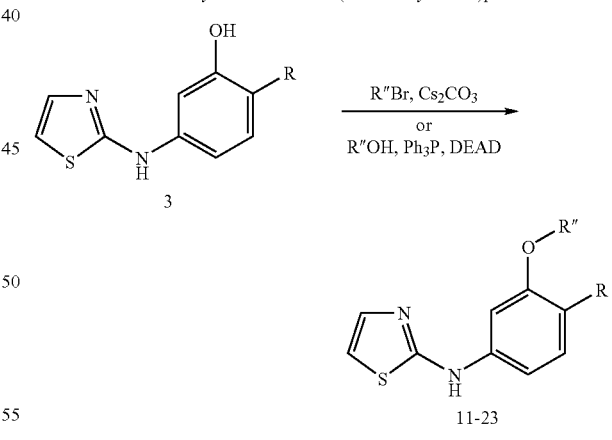

TABLE 3

| comp | R'' | R | EC$_{50}$ (μM) | IC$_{50}$ (μM) |
|---|---|---|---|---|
| 18b | ⟨structure⟩ | CH$_3$ | 8 | 32 |
| 18d | ⟨structure⟩ | Cl | 1 | 18 |
| 18e | ⟨structure⟩ | CH$_2$CH$_3$ | 10 | 29 |

TABLE 3-continued

| comp | R'' | R | EC$_{50}$ (μM) | IC$_{50}$ (μM) |
|------|-----|---|----------------|----------------|
| 19d  | (3-methyl-2-buten-yl) | Cl | N/A | 22 |
| 20d  | (cyclopentenylmethyl) | Cl | 5   | 15 |
| 20h  | (cyclopentenylmethyl) | CN | N/A | 1.7 |
| 21d  | (2-methylcyclopentenylmethyl) | Cl | N/A | 2.5 |
| 22d  | (cyclohexylmethyl) | Cl | N/A | 12 |
| 23d  | (n-heptyl) | Cl | N/A | 15 |

Table 4.

Example

Heteroaryl Derivatives

Typical syntheses of these derivatives was performed by reaction of 2-bromopyridine, 2-chloropyrimidine, 4-amino-2-chloropyrimidine[15], 2-chloro-4-methylpyrimidine[16], 2-chloro-4-methoxypyrimidine[17] and 2-amino-4-chloropyrimidine[1] with the corresponding 5-amino-2-substitutedphenols in the presence of HCl, followed by reaction with 4-bromo-2-methyl-2-butene in presence of $Cs_2CO_3$ as a base. Compounds 46 and 47 were synthesized by reaction of 2-chloro-5-(pyrimidin-2-ylamino)phenol 35d with 4-methyl-pent-3-en-2-ol[18] and (2-methylcyclopent-1-yl)methanol[19], respectively, using Mitsunobu conditions[20].

[15] Minakawa, N.; Kojima, N.; Hikishima, S.; Sasaki, T.; Kiyosue, A.; Atsumi, N.; Ueno, Y.; Matsuna, A. *J. Am. Chem. Soc.* 2003, 125, 9970.
[16] Harden, D. B.; Mokrosk, M. J.; Strekowski, L. *J. Org. Chem.* 1988, 53, 4137.
[17] Katritzky, A. R.; Baykut, G.; Rachwal, S.; Szafran, M.; Caster, K. C.; Eyler, J. *J. Chem. Soc., Perkin Trans. II* 1989, 1499.
[18] Cain, M. E. *J. Chem. Soc.* 1964, 3532.
[19] a) Harding, K. E.; Clement, K. S. J. Org. Chem. 1984, 49, 2049. b) Lemieux, R. M.; Meyers, A. I. *J. Am. Chem. Soc.* 1998, 120, 5453.
[20] Lepore, S. D.; He, Y. *J. Org. Chem.* 2003, 68, 8261.

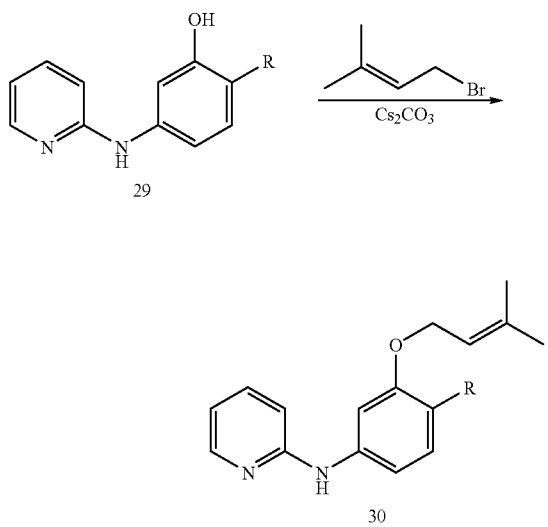

Scheme 1a Synthesis of pyridine derivatives 30.

31 R'''' = H
32 R'''' = NH$_2$
33 R'''' = CH$_3$
34 R'''' = OCH$_3$

35 R'''' = H
36 R'''' = NH$_2$
37 R'''' = CH$_3$
38 R'''' = OCH$_3$

39 R'''' = H
40 R'''' = NH$_2$
41 R'''' = CH$_3$
42 R'''' = OCH$_3$

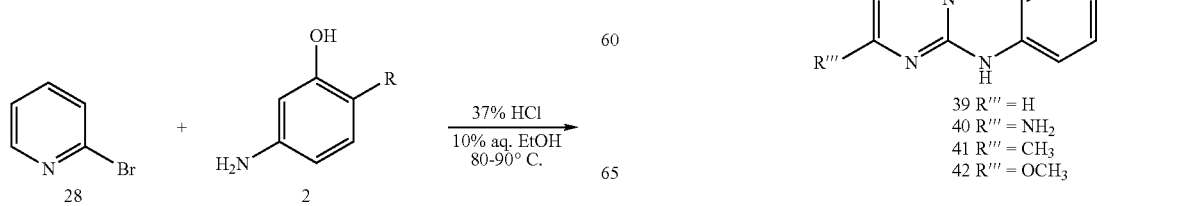

Scheme 2a. Synthesis of pyrimidine derivatives 39-42 and 45.

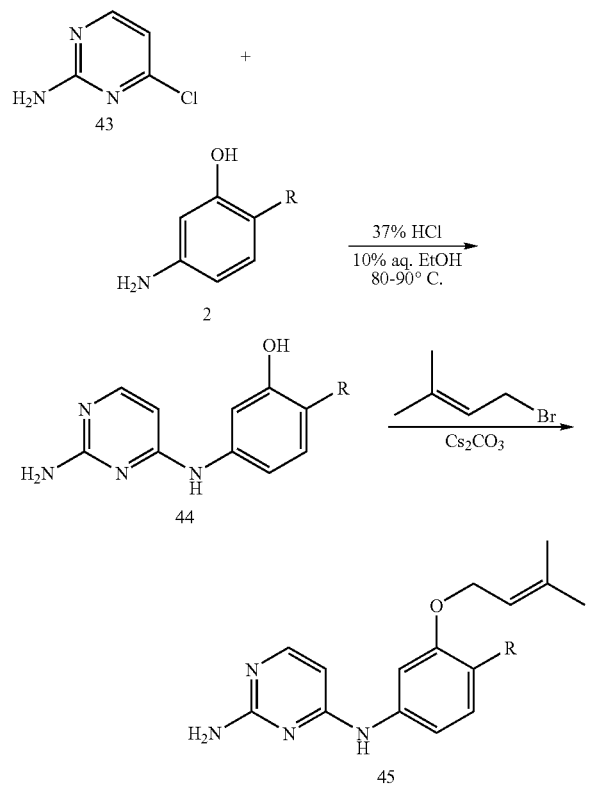

Scheme 3a. Synthesis of analogues 46-47.

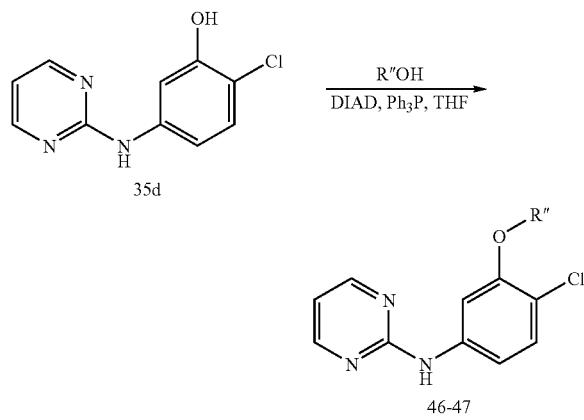

Biological activity.

TABLE 1a
Anti-HIV activity for heteroaryl derivatives.

| Comp | Het | R | EC$_{50}$(μM) | IC$_{50}$(μM) |
|---|---|---|---|---|
| 30b |  | CH$_3$ | N/A | 35 |
| 30d |  | Cl | 3.2 | 15 |
| 30h |  | CN | N/A | 0.29 |

TABLE 1a-continued
Anti-HIV activity for heteroaryl derivatives.

| Comp | Het | R | EC$_{50}$(μM) | IC$_{50}$(μM) |
|---|---|---|---|---|
| 39b |  | CH$_3$ | 2.8 | 78 |
| 39d |  | Cl | 0.2 | 2.5 |
| 39h |  | CN | N/A | <0.2 |
| 40b |  | CH$_3$ | 0.35 | 6.5 |
| 40d |  | Cl | 0.075 | >1 |
| 41d |  | Cl | N/A | <0.2 |
| 42b |  | CH$_3$ | 0.32 | 41 |
| 42d |  | Cl | 0.010 | 9.0 |
| 45b |  | CH$_3$ | N/A | 0.6 |
| 45d |  | Cl | N/A | 2.0 |
| 4b |  | CH$_3$ | 3 | 17 |
| 4d |  | Cl | 0.3 | 26 |
| 4h |  | CN | 0.21 | 0.75 |
| 48 |  | Cl | 0.18 | 2.8 |
| 49 |  | Cl | 0.065 | 2.5 |
| Nevirapine |  |  | 0.12 | >10 |

Several of these compounds were very potent anti-HIV agents with activities in the 10 nM to 100 nM rang; activities of nevirpaine and d4T in our assay are 120 nM and 3000 nM, respectively.

TABLE 2a
Anti-HIV activity for N-(4-chloro-3-(substituted)phenyl)pyrimidin-2-amine derivatives.

| comp | R'' | EC$_{50}$(μM) | IC$_{50}$(μM) |
|---|---|---|---|
| 39d |  | 0.2 | <0.2 |
| 46 |  | N/A | 22 |

TABLE 2a-continued

Anti-HIV activity for N-(4-chloro-3-(substituted)phenyl)pyrimidin-2-amine derivatives.

| comp | R'' | EC$_{50}$(μM) | IC$_{50}$(μM) |
|---|---|---|---|
| 47 | 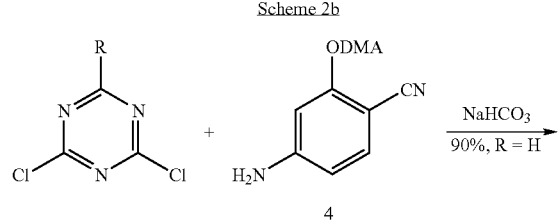 | N/A | 2.5 |

Chemistry and Biology of Pyrimidinyl and Triazinyl Amines

Syntheses of the 2-thiazoyl and 2-pyrimidine derivatives were described previously and followed the general route in Scheme 1. See, Ruiz-Caro, et al., *Bioorg. Med. Chem. Lett.* 2006, 16, 668-671.

For the triazene analogs, dichloro and trichlorotriazine were used as starting materials. They were typically added to the preformed dimethylallyl (DMA)-derivatized aminophenol, which was prepared by SnCl$_2$ reduction of the corresponding nitrophenol with subsequent substitution of chlorines on the triazine. The routes for a di- and a tri-substituted triazine are shown in Scheme 2. The parent triazine 3 (R═H) was not easily available owing to instability of chlorotriazine. Monochloro triazines such as 5 (R═Cl) could also be converted to the amino derivatives in near quantitative yield by treatment with the amine in methanol. The thiomethoxy analog of 5 (R═H) was prepared in 77% yield using NaSMe in THF rather than NaOMe.

Scheme 1b.

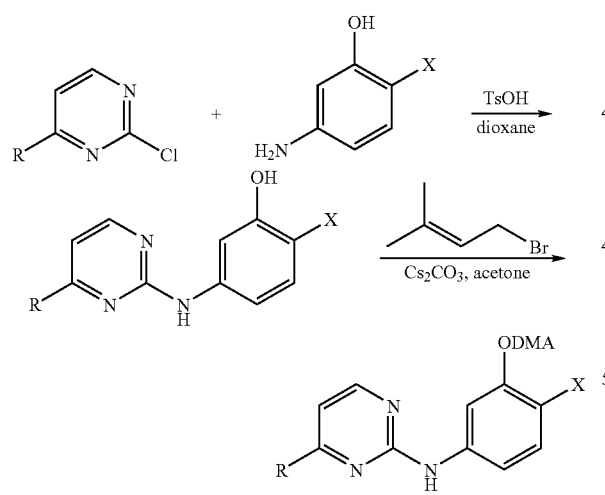

A variety of alternatives for the U group was also tested in the 2-thiazoyl series, and ODMA emerged as preferred for potency. Further investigations were made for the 2-pyrimidines. Attachment was normally effected by base-catalyzed substitution (Scheme 1c) or by alcohol coupling under Mitsunobu conditions (Ph$_3$P, DEAD). See, Ruiz-Caro, et al., *Bioorg. Med. Chem. Lett.* 2006, 16, 668-671 However, phenyl and tolyl ether analogs, Het-NH-PhX-OPhR', were prepared by coupling (R'Ph)$_2$I$^+$ salts and the phenol derivative, while preparation of a thioether analog utilized PhSCu to yield selectively the desired meta relationship with the amino group in 6 (Scheme 3). See, Gong, et al. *Biochem. Pharmacol.* 1994, 47, 171-174.

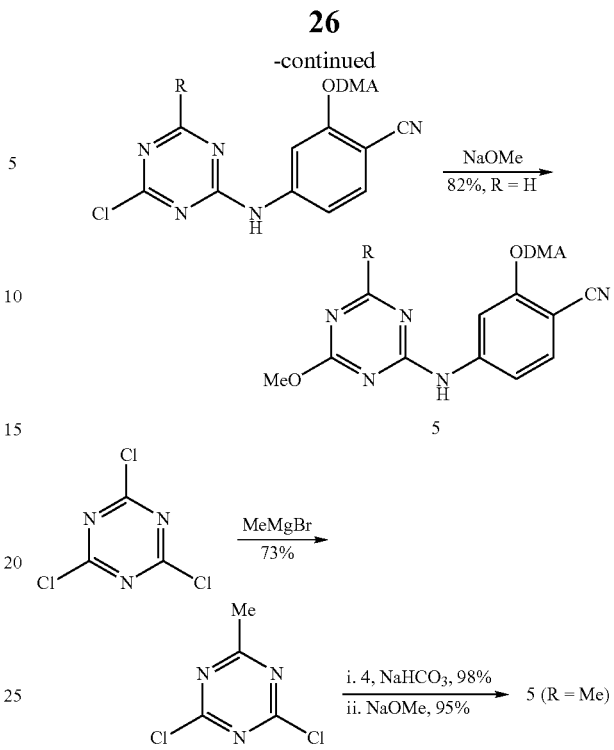

Scheme 3b.

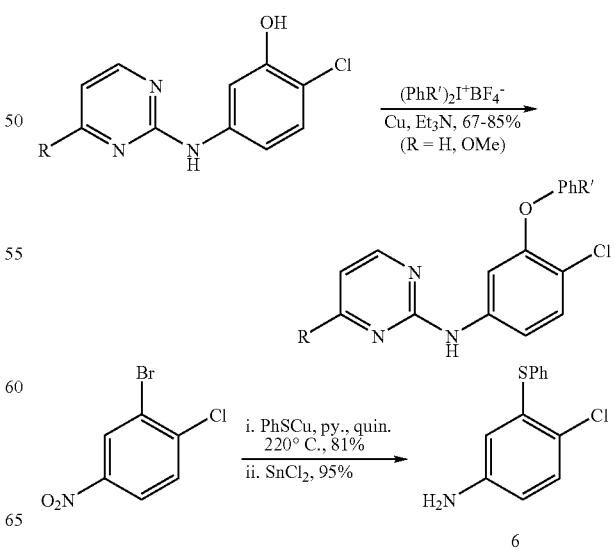

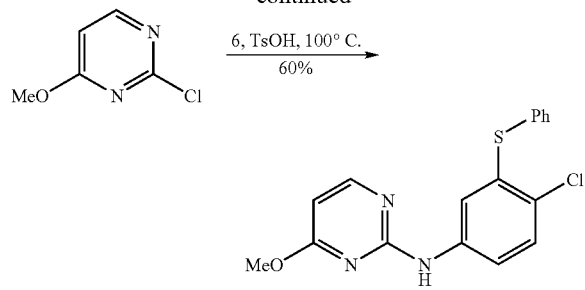

Activities against the IIIB strain of HIV-1 were determined using MT-2 human T-cells; the $EC_{50}$ values are the dose required to achieve 50% protection of the infected cells using the MTT colorimetric method. The $CC_{50}$ for inhibition of MT-2 cell growth by 50% was obtained simultaneously. See, Ruiz-Caro, supra. and Lin, et al., *Biochem. Pharmacol.* 1994, 47, 171-174.

Activities and Cytotoxicities

Results are listed in Table 1b for the triazene and pyrimidine derivatives 7-10.

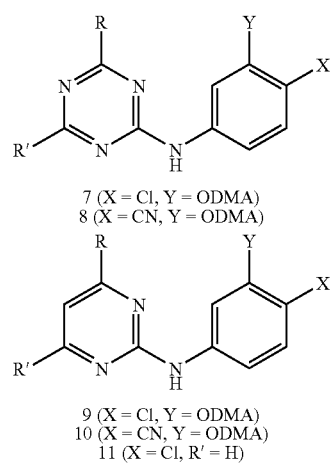

7 (X = Cl, Y = ODMA)
8 (X = CN, Y = ODMA)

9 (X = Cl, Y = ODMA)
10 (X = CN, Y = ODMA)
11 (X = Cl, R' = H)

TABLE 1B

Anti-HIV-1 activity ($EC_{50}$) and cytotoxicity ($CC_{50}$), μM, for triazene and pyrimidine derivatives

| Compound | X | R | R' | $EC_{50}^a$ | $CC_{50}^b$ |
|---|---|---|---|---|---|
| 7a | Cl | Cl | H | NA | 45.0 |
| 7b | Cl | OMe | H | 0.031 | 18.0 |
| 7c | Cl | NH₂ | H | 0.390 | 48.0 |
| 7d | Cl | NHMe | H | 0.031 | 3.1 |
| 7e | Cl | Me | Cl | 12.0 | 40.0 |
| 7f | Cl | OMe | Cl | NA | 26.0 |
| 7g | Cl | OMe | Me | 0.100 | 12.0 |
| 7h | Cl | OMe | OMe | 0.290 | 20.0 |
| 8a | CN | Cl | H | 0.310 | >100 |
| 8b | CN | OMe | H | 0.011 | 42.0 |
| 8c | CN | NH₂ | H | 0.015 | 0.20 |
| 8h | CN | OMe | OMe | 0.022 | >100 |
| 8i | CN | SMe | H | 0.005 | 8.4 |
| 8j | CN | OMe | NH₂ | 0.009 | 0.11 |
| 9b | Cl | OMe | H | 0.010 | 9.0 |
| 9c | Cl | NH₂ | H | 0.075 | 0.50 |
| 9d | Cl | NHMe | H | 0.006 | 0.69 |
| 9h | Cl | OMe | OMe | 0.250 | 28.0 |
| 9i | Cl | SMe | H | 0.018 | 2.8 |

TABLE 1B-continued

Anti-HIV-1 activity ($EC_{50}$) and cytotoxicity ($CC_{50}$), μM, for triazene and pyrimidine derivatives

| Compound | X | R | R' | $EC_{50}^a$ | $CC_{50}^b$ |
|---|---|---|---|---|---|
| 9j | Cl | OMe | NH₂ | 3.0 | 19.0 |
| 9k | Cl | OEt | H | 0.041 | 19.0 |
| 9l | Cl | CH₂OMe | H | NA | >25 |
| 9m | Cl | CH₂OH | H | NA | 0.22 |
| 9n | Cl | H | H | 0.200 | 2.5 |
| 9o | Cl | Me | H | 0.039 | 0.15 |
| 9p | Cl | Et | H | 0.016 | 0.33 |
| 10b | CN | OMe | H | 0.002 | 0.23 |
| 10c | CN | NH₂ | H | NA | 0.041 |
| 10d | CN | NHMe | H | 0.005 | 0.022 |
| 10h | CN | OMe | OMe | 0.160 | 0.810 |
| 10n | CN | H | H | 0.017 | 0.036 |
| Nevirapine | | | | 0.110 | >10 |
| Efavirenz | | | | 0.002 | >0.10 |
| TMC125 | | | | 0.002 | >1 |

$^a$For 50% protection in MT-2 cells; antiviral curves used triplicate samples at each concentration. NA for $EC_{50}$ > $CC_{50}$.
$^b$For 50% inhibition of MT-2 cell growth; toxicity curves also used triplicate samples.

Some general patterns for equivalently substituted systems are: (1) the triazenes are less active than the pyrimidines by a factor of 3-5; (2) the cyano analogs (X=CN) are more active than the chloro analogs (X=Cl) by a factor of 3-10; (3) compounds with a single OMe, SMe, or NHMe substituent on the heterocycle are particularly potent, i.e., 7-10b,d,i (4) the triazenes show little cytotoxicity with the exception of the amino, cyano compounds 8c and 8j; (5) the cyano pyrimidines are both potent and cytotoxic, though 10b has a safety margin ($CC_{50}/EC_{50}$)>100, and (6) many of the compounds are highly potent with $EC_{50}$ values below 20 nM, and three of the potent triazenes (8b, 8h, 8i) also have safety margins >1000. Understanding of the origins and variations of the cytotoxicity is lacking. Since it was more pronounced for the 2-pyrimidines than the 2-thiazoles, a recognition element associated with the heterocycle in the present NNRTI series appeared to be operative. Indeed, this notion is further supported by the favorable results for the triazenes.

Results are also included in Table 1b for three reference NNRTIs, nevirapine (Viramune®), efavirenz (Sustiva®), and TMC125 (etravirine). The present compounds are considerably more effective against WT HIV-1 than nevirapine, and the most active ones are in the low nM-range like efavirenz and TMC125. Of course, pharmacologically important properties of the NNRTIs are also relevant, as discussed further below.

The results for the alternative choices for the U group in the pyrimidine series are listed in Table 2b, below. As with the 2-thiazoles for which various heteroarylmethoxy options for U were tried, no choice has emerged superior to ODMA. Removal of the Z-methyl group of ODMA to yield the E-buten-2-yl ethers, 11a and 11c, reduces potency ca. 10-fold. However, this change could be advantageous for increased resilience to the Y181C variant of HIV-RT. The phenyl ethers 11b and 11d are ca. 100-fold less potent than the DMA ethers, and only the m-tolyl analog 11f showed somewhat improved performance. Among the aryl ethers, the thioether 11h was the most potent, though its $EC_{50}$ is still 32-fold higher than that for the DMA ether 9b.

TABLE 2b

Anti-HIV-1 activity (EC$_{50}$) and cytotoxicity (CC$_{50}$), μM, for derivatives of pyrimidine 11[a]

| Compd | R | Y | EC$_{50}$ | CC$_{50}$ |
|---|---|---|---|---|
| 9n | H | ODMA | 0.200 | 2.5 |
| 11a | H | (E)—OCH$_2$CH=CHCH$_3$ | 2.3 | 31.0 |
| 11b | H | OPh | 13.0 | 30.0 |
| 9b | OMe | ODMA | 0.010 | 9.0 |
| 11c | OMe | (E)—OCH$_2$CH=CHCH$_3$ | 0.089 | 17.0 |
| 11d | OMe | OPh | 2.5 | 38.0 |
| 11e | OMe | O-o-MePh | NA | 13.0 |
| 11f | OMe | O-m-MePh | 0.540 | 18.0 |
| 11g | OMe | O-p-MePh | 10.0 | >100 |
| 11h | OMe | SPh | 0.320 | 21.0 |

[a]NA for EC$_{50}$ > CC$_{50}$.

Further Exemplary Chemistry Compound According to the Invention

The following further compounds 50-61 and related analogs as presented were synthesized.

50

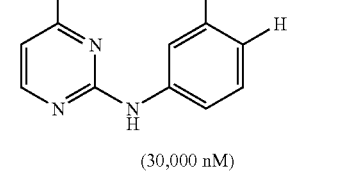

(30,000 nM)

51

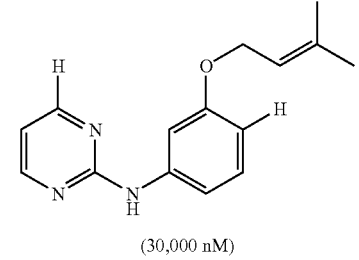

(200 nM)

52

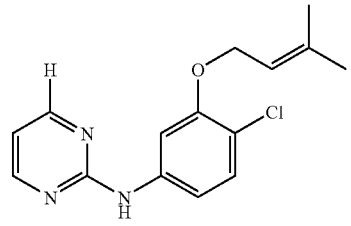

(10 nM)

53

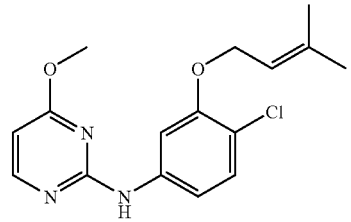

(31 nM)

54

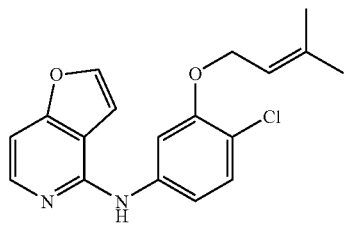

55

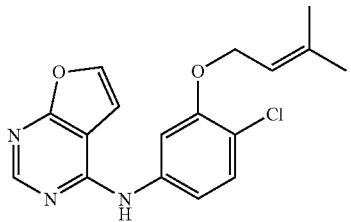

56

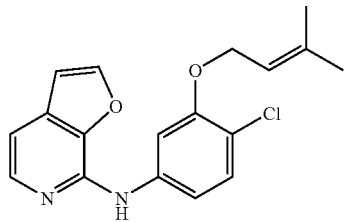

57

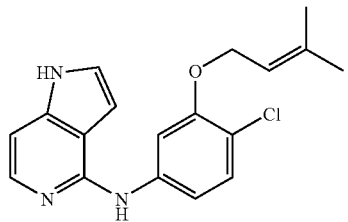

58

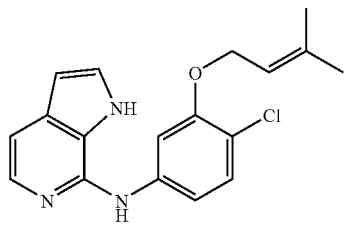

59

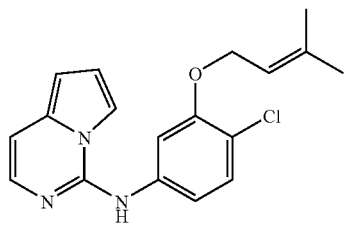

60

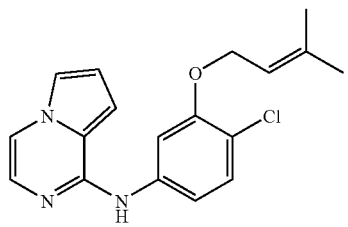

-continued

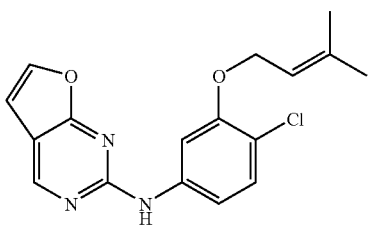
61

Synthesis for Furopyridine Derivatives 56 and 55

7-Chloro-furo[2,3-c]pyridine 1[21], 5-amino-2-R-phenol 2 (1.0 equiv) and 37% HCl solution (1.0 equiv) in 10% aqueous EtOH solution were stirred at 90° C. for 12 h. The reaction mixture was diluted with ethyl acetate and washed with aqueous NaHCO$_3$ solution and brine. The organic phase was dried over anhydrous Na$_2$SO$_4$, concentrated. The crude product was purified by flash chromatography on silica gel to give 3.
[21] Shiotani, S.; Morita, H. *J. Heterocycl. Chem.* 1982, 19, 1207-9.

A mixture of 3 and Cs$_2$CO$_3$ (1.1 equiv) in acetone (0.1 M) was treated with 3,3-dimethylallyl bromide (1.0 equiv) at room temperature. After 2-4-h, the reaction mixture was diluted with EtOAc and washed with aqueous NH$_4$Cl solution and brine. The organic phase was dried over anhydrous Na$_2$SO$_4$, concentrated and the crude product was purified by flash chromatography on silica gel to give 4.

Scheme 4c. Synthesis for Furopyridines 56.

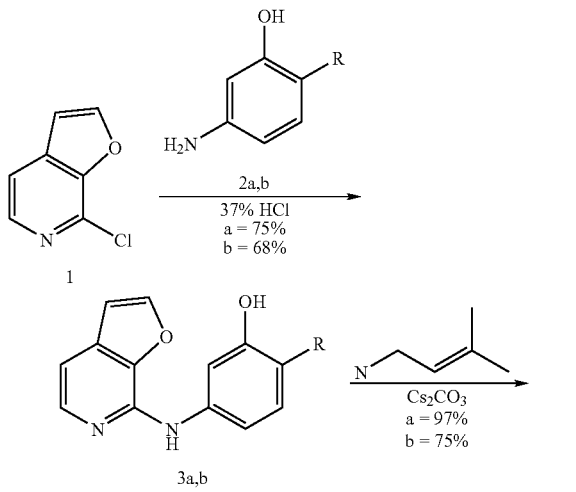

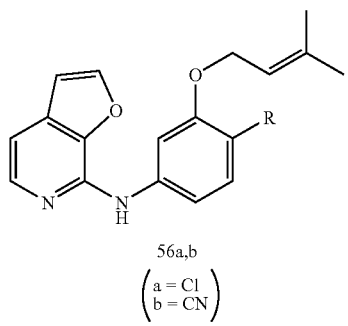

4-Chloro-furo[3,2-c]pyridine, 5-amino-2-R-phenol 2 (1.0 equiv) and 37% HCl solution (1.0 equiv) in 10% aqueous EtOH solution were stirred at 90° C. for 12 h. The reaction mixture was diluted with ethyl acetate and washed with aqueous NaHCO$_3$ solution and brine. The organic phase was dried over anhydrous Na$_2$SO$_4$, concentrated. The crude product was purified by flash chromatography on silica gel to give 56.

A mixture of 6 and Cs$_2$CO$_3$ (1.1 equiv) in acetone (0.1 M) was treated with 3,3-dimethylallyl bromide (1.0 equiv) at room temperature. After 2-4-h, the reaction mixture was diluted with EtOAc and washed with aqueous NH$_4$Cl solution and brine. The organic phase was dried over anhydrous Na$_2$SO$_4$, concentrated and the crude product was purified by flash chromatography on silica gel to give 7.

Scheme 5c. Synthesis for Furopyridines 55.

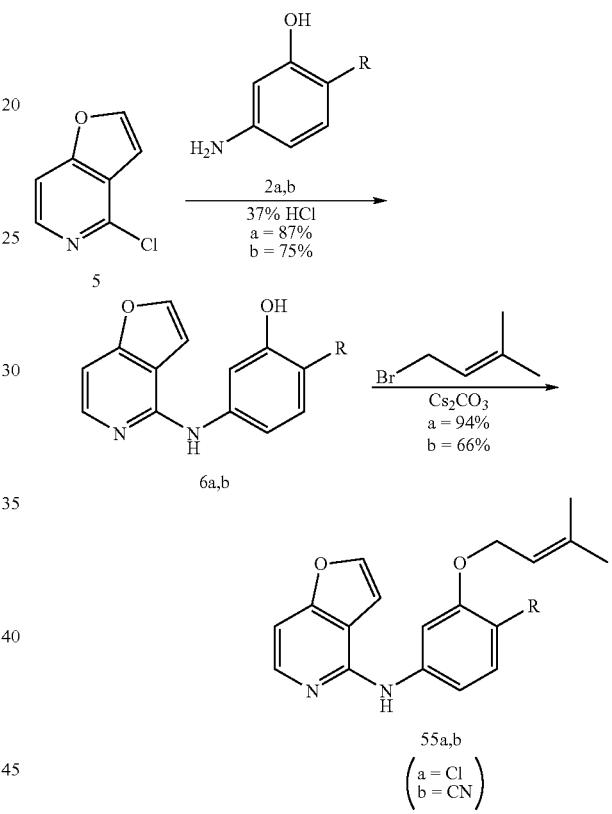

Synthesis for Pyrrolopyrimidine Derivative 59

Scheme 6

Using a high pressure tube, propyne (excess) was condensed in a mixture of 2,4-dichloro-pyrimidine, CuI (10 mol %), Pd(PPh$_3$)$_2$Cl$_2$ (5 mol %), and Et$_3$N (solvent) at −78° C. The mixture was slowly warmed up and stirred at room temperature for 12 h. After this period, the mixture was quenched with aqueous NH$_4$Cl. The aqueous phase was thoroughly extracted with hexanes. The combined organic extracts were washed with brine, dried over anhydrous Na$_2$SO$_4$, and concentrated under reduced pressure. The residue was purified by silica gel chromatography to give 9.

The compound 9 and CuBr (1.0 equiv) in DMA-Et$_3$N (7:1 mixture, 0.02M) was heated at 130° C. for 12 h. The reaction was protected from the light by covering the flash with aluminum foil. After this period, the mixture was quenched with aqueous NH₄Cl. The aqueous phase was thoroughly extracted with hexanes. The combined organic extracts were washed with brine, dried over anhydrous Na₂SO₄, and concentrated under reduced pressure. The residue was purified by silica gel chromatography to give 10.

Compound 10, 5-amino-2-chlorophenol 2a (1.0 equiv) and 37% HCl solution (1.0 equiv) in 10% aqueous EtOH solution was stirred at 90° C. for 12 h. The reaction mixture was diluted with ethyl acetate and washed with aqueous NaHCO₃ solution and brine. The organic phase was dried over anhydrous Na₂SO₄, concentrated. The crude product was purified by flash chromatography on silica gel to give 11.

A mixture of 11 and Cs₂CO₃ (1.1 equiv) in acetone (0.1 M) was treated with 3,3-dimethylallyl bromide (1.0 equiv) at room temperature. After 2-4-h, the reaction mixture was diluted with EtOAc and washed with aqueous NH₄Cl solution and brine. The organic phase was dried over anhydrous Na₂SO₄, concentrated and the crude product was purified by flash chromatography on silica gel to give 59.

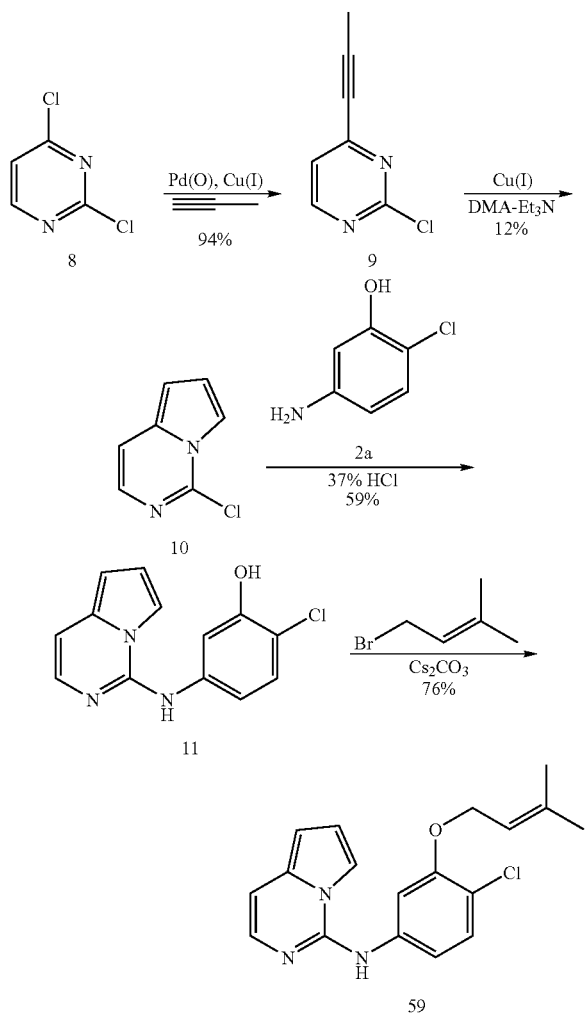

Synthesis of Isoquinoline Derivatives 62

To a solution of 5-amino-2-R-phenol 14, 1-Chloroisoquinoline 13 (1.3 equiv) in 10% aqueous EtOH 37% HCl (1.0 equiv) was added, the solution was stirred at 90° C. for 6 h. The reaction mixture was diluted with ethyl acetate and washed with saturated NaHCO₃ solution and brine. The organic phase was dried over anhydrous Na₂SO₄, concentrated. The crude product was purified by flash chromatography on silica gel to give 15.

Solution of 15 and Cs₂CO₃ (1.2 equiv) in acetone (0.1 M) was treated with 3,3-dimethylallyl bromide (1.2 equiv) at room temperature. After 2-4 h, the reaction mixture was diluted with EtOAc and washed with aqueous NH₄Cl solution and brine. The organic phase was dried over anhydrous Na₂SO₄, concentrated and the crude product was purified by flash chromatography on silica gel to give 16.

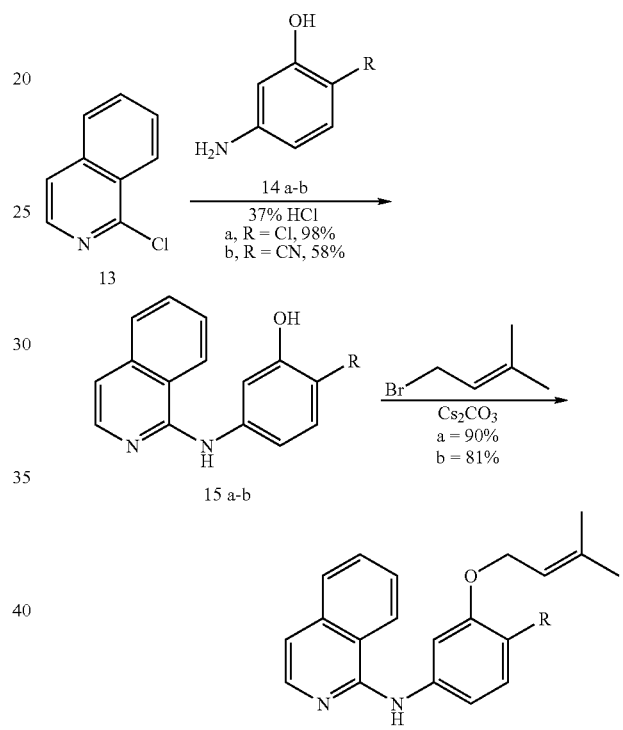

Synthesis of Quinazoline Derivatives 63

4-Hydroxyquinazoline 21 (0.8 g, 5.5 mmol), and N,N-diisopropylethylamine (0.5 ml) were refluxed in phosphorus oxychloride (11.0 ml) for 15 h. Phosphorus oxychloride was distilled under reduced pressure, the resulting oil was diluted with ethyl acetate washed with K₂CO₃ solution, dried over anhydrous Na₂SO₄, concentrated and the crude product was purified by flash chromatography on silica gel to give 6 (0.48 g, 58%)

A solution of 5-amino-2-Chloro-phenol 18a and 4-chloroquinazoline 22 (1.1 equiv), triethylamine (2.0 equiv) in isopropanol was refluxed with stirring for 1 h. The reaction mixture was concentrated under vacuum. The crude product was purified by flash chromatography on silica gel to give 23a.

A solution of 23a (0.115 g, 0.42 mmol) and Cs₂CO₃ (0.163 g, 0.5 mmol) in acetone (5.0 ml) was treated with 3,3-dimethylallyl bromide (0.059 ml, 0.5 mmol) at room temperature.

After 9 h, the reaction mixture was diluted with EtOAc and washed with aqueous NH$_4$Cl solution and brine. The organic phase was dried over anhydrous Na$_2$SO$_4$, concentrated and the crude product was purified by flash chromatography on silica gel to give 63a (0.09 g, 63%).

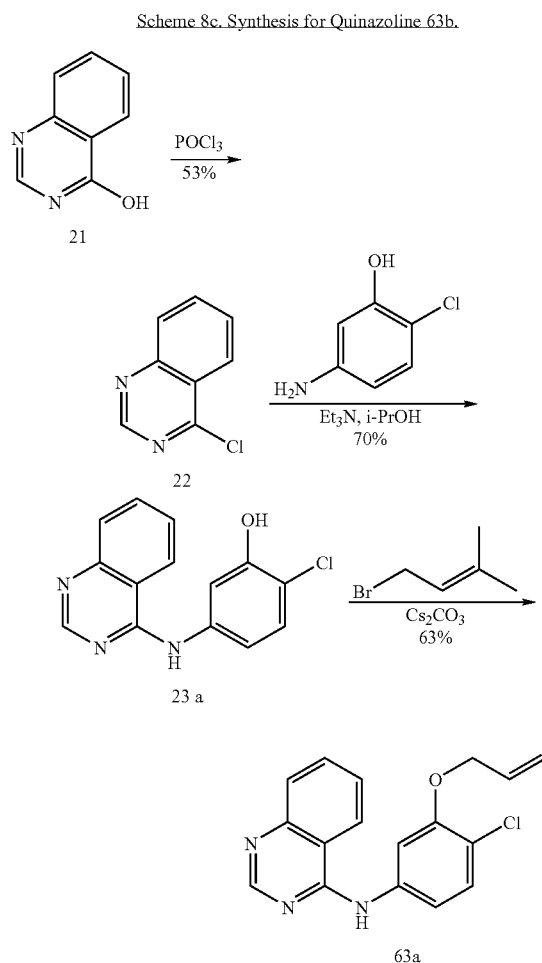

To a solution of 5-amino-2-cyano-phenol 18b, 4-chloro-quinazoline 22 (1.1 equiv) in 10% aqueous EtOH 37% HCl (1.0 equiv) was added; the solution was stirred at 90° C. for 6 h. The reaction mixture was diluted with ethyl acetate and washed with saturated NaHCO$_3$ solution and brine. The organic phase was dried over anhydrous Na$_2$SO$_4$, concentrated. The crude product was purified by flash chromatography on silica gel to give 23b.

A solution of 23b (0.1 g, 0.38 mmol) and Cs$_2$CO$_3$ (0.149 g, 0.46 mmol) in acetone (5.0 ml) was treated with 3,3-dimethylallyl bromide (0.054 ml, 0.46 mmol) at room temperature. After 9 h, the reaction mixture was diluted with EtOAc and washed with aqueous NH$_4$Cl solution and brine. The organic phase was dried over anhydrous Na$_2$SO$_4$, concentrated and the crude product was purified by flash chromatography on silica gel to give 63b (0.077 g, 61%).

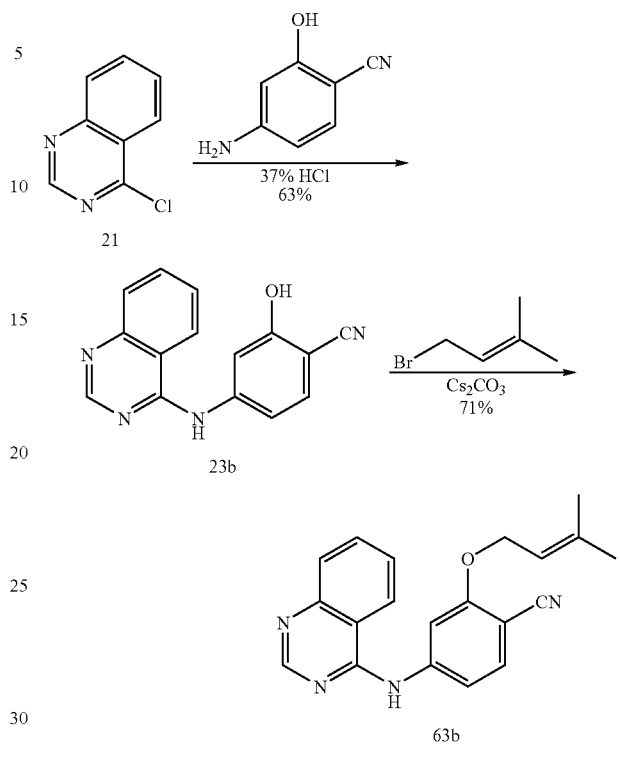

Representative Anti-HIV Activity Data for Bicyclic-Heteroaryl Phenyl Amines

TABLE

| Compound | EC$_{50}$ (μM) | IC$_{50}$ (μM) |
|---|---|---|
| furopyridine 56a | 0.080 | 21.0 |
| furopyridine 56b | 0.011 | 0.091 |
| furopyridine 55a | 0.003 | 25.0 |
| furopyridine 55b | <0.002 | 0.320 |
| isoquinoline 62a | 0.034 | 19.0 |
| isoquinoline 62b | 0.003 | 4.4 |
| compound 54 | 0.006 | 25.0 |
| compound 54-CN* | 0.003 | 0.320 |
| compound 58 | 0.900 | 9.2 |
| compound 59 | 0.130 | 17.0 |
| compound 60 | 0.019 | 20.0 |
| compound 60-CN* | 0.018 | 0.150 |
| compound 61 | 0.130 | 20.0 |
| nevirapine | 0.110 | >10 |
| efavirenz | 0.002 | >0.1 |
| RMC125 | 0.002 | >1 |

Anti-HIV Activity (EC$_{50}$) and Cytotoxicity (IC$_{50}$) in MT-2 Cell Assays

*Cyano replaces chloro

The present invention is now described, purely by way of illustration, in the following examples. It will be understood by one of ordinary skill in the art that these examples are in no way limiting and that variations of detail can be made without departing from the spirit and scope of the present invention.

EXAMPLES

General Procedure for the synthesis of 2-R-5-(thiazol-2-ylamino)phenol (3)

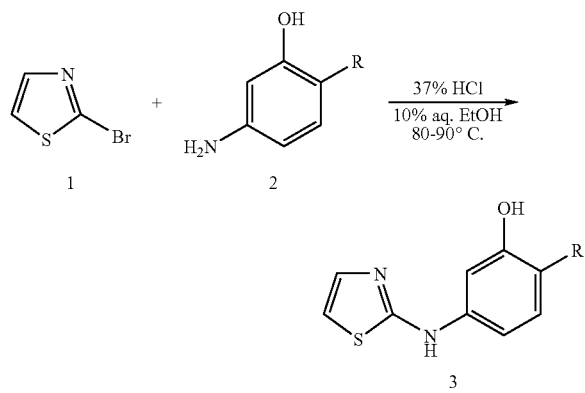

2-Bromothiazole 1 (2 equiv), 5-amino-2-R-phenol 2 (1 equiv) and 37% HCl solution (2 equiv) in 10% aqueous EtOH solution was stirred at 90° C. for 24 h. The reaction mixture was diluted with ethyl acetate and washed with 5% aqueous $K_2CO_3$ solution and brine. The organic phase was dried over $Na_2SO_4$, concentrated and the crude product was purified by flash chromatography on silica gel.

*N-(3-phenoxyphenyl)thiazol-2-amine; JLJ000001 (jr-11a)

Following the general procedure for the synthesis of 2-R-5-(thiazol-2-ylamino)phenol, 2-bromothiazole (0.09 mL, 1.02 mmol), 3-phenoxyaniline (94 mg, 0.51 mmol) and 37% HCl solution (0.09 mL, 1.02 mmol) in 10% aqueous EtOH solution (1 mL) was stirred at 90° C. for 24 h. The title compound was obtained after purification by flash chromatography on silica gel (hexane:EtOAc 9/1) in 75% yield (102 mg).

$^1$H NMR (400 MHz, CDCl$_3$) δ 10.22 (br s, 1H), 7.39 (t, J=8.0 Hz, 2H), 7.31 (t, J=8.0 Hz, 1H), 7.16 (t, J=7.6 Hz, 1H), 7.13 (d, J=3.9 Hz, 1H), 7.11-7.08 (m, 3H), 6.98 (t, J=2.3 Hz, 1H), 6.71 (dd, J=8.1, 1.9 Hz, 1H), 6.58 (d, J=3.9 Hz, 1H); $^{13}$C NMR (100 MHz, CDCl$_3$) δ 165.9, 158.7, 156.6, 142.2, 138.0, 130.5, 129.8, 123.7, 119.6, 112.5, 111.9, 107.7, 107.1; MS (FAB) m/z (rel intensity) 270 (19), 269 ([M$^+$], 100), 268 (27); HRMS (FAB) calcd. for C$_{15}$H$_{12}$N$_2$OS [M$^+$] 268.3348, found 269.0754.

*N-(3-ethoxyphenyl)thiazol-2-amine; JLJ000002 (jr-12a)

Following the general procedure for the synthesis of 2-R-5-(thiazol-2-ylamino)phenol, 2-bromothiazole (0.15 mL, 1.66 mmol), 3-ethoxyaniline (0.11 mL, 0.83 mmol) and 37% HCl solution (0.14 mL, 1.66 mmol) in 10% aqueous EtOH solution (1 mL) was stirred at 90° C. for 24 h. The title compound was obtained after purification by flash chromatography on silica gel (hexane:EtOAc 8/2) in 53% yield (97 mg).

$^1$H NMR (400 MHz, CDCl$_3$) δ 9.97 (br s, 1H), 7.33 (d, J=3.7 Hz, 1H), 7.24 (t, J=8.0 Hz, 1H), 6.94 (t, J=2.2 Hz, 1H), 6.90 (dd, J=8.0, 1.5 Hz, 1H), 6.62 (d, J=3.7 Hz, 1H), 6.60 (dd, J=8.1, 1.5 Hz, 1H), 4.04 (q, J=7.0 Hz, 2H), 1.42 (t, J=7.0 Hz, 3H); $^{13}$C NMR (100 MHz, CDCl$_3$) δ 166.3, 160.0, 142.0, 138.1, 130.2, 110.3, 108.8, 107.0, 104.3, 63.5, 14.8; MS (FAB) m/z (rel intensity) 222 (16), 221 ([M$^+$], 100), 220 (29), 193 (12), 57 (8); HRMS (FAB) calcd. for C$_{11}$H$_{12}$N$_2$OS [M$^+$] 220.2908, found 221.0754.

*3-(Thiazol-2-ylamino)phenol (Procedure jrII-180; data in jr-15a)

Following the general procedure for the synthesis of 2-R-5-(thiazol-2-ylamino)phenol, 2-bromothiazole (3.3 mL, 36.6 mmol), 3-aminophenol (3.1 mL, 18.3 mmol) and 37% HCl solution (3.1 mL, 36.6 mmol) in 10% aqueous EtOH solution (30 mL) was stirred at 90° C. for 24 h. The title compound was obtained after purification by flash chromatography on silica gel (hexane:EtOAc 6/4) in 80% yield (2.98 g).

$^1$H NMR (400 MHz, CD$_3$OD) δ 7.20 (d J=3.7 Hz, 1H), 7.13 (d, J=8.1 Hz, 1H), 7.09-7.08 (m, 1H), 6.93-6.88 (m, 1H), 6.75 (d, J=3.7 Hz, 1H), 6.46 (dd, J=8.1, 2.2 Hz, 1H); $^{13}$C NMR (100 MHz, CD$_3$OD) δ 167.6, 159.7, 144.1, 139.7, 131.3, 110.6, 109.3, 106.3.

*2-Methyl-5-(thiazol-2-ylamino)phenol (jr-171a)

Following the general procedure for the synthesis of 2-R-5-(thiazol-2-ylamino)phenol, 2-bromothiazole (0.27 mL, 3.05 mmol), 5-amino-3-methylphenol (188 mg, 1.5 mmol) and 37% HCl solution (0.26 mL, 3.05 mmol) in 10% aqueous EtOH solution (5 mL) was stirred at 90° C. for 24 h. The title compound was obtained after purification by flash chromatography on silica gel (hexane:EtOAc 1/1) in 74% yield (233 mg).

$^1$H NMR (500 MHz, CD$_3$OD) g 7.16 (d, J=3.7 Hz, 1H), 7.04 (d J=2.1 Hz, 1H), 6.99 (d, J=8.1 Hz, 1H), 6.78 (dd, J=8.1, 2.1 Hz, 1H), 6.67 (d, J=3.7 Hz, 4H), 2.15 (s, 3H); $^{13}$C NMR (125 MHz, CD$_3$OD) δ 168.4, 157.4, 141.6, 139.6, 132.5, 120.4, 111.2, 108.8, 106.7, 16.2.

*2-Methoxy-5-(thiazol-2-ylamino)phenol (jr-194a)

Following the general procedure for the synthesis of 2-R-5-(thiazol-2-ylamino)phenol; 2-bromothiazole (0.27 mL, 3.05 mmol), 5-amino-2-methoxyphenol (212 mg, 1.52 mmol) and 37% HCl solution (0.26 mL, 3.05 mmol) in 10% aqueous EtOH solution (5 mL) was stirred at 90° C. for 24 h. The title compound was obtained after purification by flash chromatography on silica gel (hexane:EtOAc 1/1) in 62% yield (210 mg).

$^1$H NMR (500 MHz, CD$_3$OD) δ 7.14 (d, Y 3.7 Hz, 1H), 7.02 (d, J=2.2 Hz, 1H), 6.87 (d, J=2.2 Hz, 1H), 6.86 (m, 1H), 6.65 (d, J=3.7 Hz, 1H), 3.81 (s, 3H); $^{13}$C NMR (125 MHz, CD$_3$OD) δ 169.1, 148.6, 145.5, 139.6, 136.9, 114.1, 111.8, 108.9, 108.6, 57.3.

*2-Chloro-5-(thiazol-2-ylamino)phenol (jrII-127a)

Following the general procedure for the synthesis of 2-R-5-(thiazol-2-ylamino)phenol, 2-bromothiazole (0.25 mL, 2.78 mmol), 5-amino-2-chlorophenol (200 mg, 1.39 mmol) and 37% HCl solution (0.24 mL, 2.78 mmol) in 10% aqueous EtOH solution (5 mL) was stirred at 90° C. for 24 h. The title compound was obtained after purification by flash chromatography on silica gel (hexane:EtOAc 7/3) in 69% yield (217 mg).

$^1$H NMR (400 MHz, CD$_3$OD) δ 7.34 (d, J=2.5 Hz, 1H), 7.21 (d, J=3.7 Hz, 1H), 7.18 (d, J=8.6 Hz, 1H), 6.88 (dd, J=8.6, 2.5 Hz, 1H), 6.76 (d, J=3.7 Hz, 1H); $^{13}$C NMR (125 MHz, CD$_3$OD) δ 167.1, 155.0, 142.8, 139.8, 131.4, 114.7, 111.4, 109.7, 107.3.

*2-Hydroxy-4-(thiazol-2-ylamino)benzonitrile (Procedure jrII-183, data in jrII-155a)

Following the general procedure for the synthesis of 2-R-5-(thiazol-2-ylamino)phenol, 2-bromothiazole (0.94 mL, 10.4 mmol), 4-amino-2-hydroxybenzonitrile (696 mg, 5.2 mmol) and 37% HCl solution (0.88 mL, 10.4 mmol) in 10% aqueous EtOH solution (20 mL) was stirred at 90° C. for 24 h. The title compound was obtained after purification by flash chromatography on silica gel (hexane:EtOAc 1/1) in 26% yield (293 mg).

$^1$H NMR (500 MHz, CD$_3$OD) δ 7.60 (d, J=1.8 Hz, 1H), 7.39 (d, J=8.6 Hz, 1H), 7.31 (d, J=3.7 Hz, 1H), 6.93 (dd, J=8.6, 1.9 Hz, 1H), 6.91 (d, J=3.7 Hz, 1H); $^{13}$C NMR (125 MHz, CD$_3$OD) δ 165.4, 163.3, 148.5, 140.3, 135.1, 119.1, 111.2, 110.4, 104.5, 92.7.

*2-Ethyl-5-(thiazol-2-ylamino)phenol (jrII-136a)

Following the general procedure for the synthesis of 2-R-5-(thiazol-2-ylamino)phenol, 2-bromothiazole (0.35 mL, 3.86 mmol), 5-amino-2-ethylphenol (265 mg, 1.93 mmol) and 37% HCl solution (0.32 mL, 3.86 mmol) in 10% aqueous EtOH solution (10 mL) was stirred at 90° C. for 24 h. The title compound was obtained after purification by flash chromatography on silica gel (hexane:EtOAc 6/4) in 69% yield (292 mg).

$^1$H NMR (500 MHz, CD$_3$OD) δ 7.16 (d, J=3.7 Hz, 1H), 7.04 (d, J=2.2 Hz, 1H), 7.00 (d, J=8.1 Hz, 1H), 6.80 (dd, J=8.1, 2.2 Hz, 1H), 6.64 (d, J=3.7 Hz, 1H), 2.59 (q, J=7.5 Hz, 2H), 1.18 (d, J=7.5 Hz, 3H); $^{13}$C NMR (125 MHz, CD$_3$OD) δ 168.5, 157.0, 141.5, 139.6, 131.1, 126.9, 111.3, 108.9, 106.9, 24.3, 15.4.

*2-Propyl-5-(thiazol-2-ylamino)phenol (jrII-165a)

Following the general procedure for the synthesis of 2-R-5-(thiazol-2-ylamino)phenol, 2-bromothiazole (1.26 mL, 14.0 mmol), 5-amino-2-propylphenol (1.1 g, 7.0 mmol) and 37% HCl solution (1.21 mL, 14.0 mmol) in 10%, aqueous EtOH solution (20 mL) was stirred at 90° C. for 24 h. The title compound was obtained after purification by flash chromatography on silica gel (hexane:EtOAc 8/2) in 36% yield (588 mg).

$^1$H NMR (500 MHz, CD$_3$OD) δ 9.29-9.10 (br s, 1H), 7.16 (d, J=3.4 Hz, 1H), 7.04 (d, J=2.2 Hz, 1H), 6.98 (d, J=8.0 Hz, 1H), 6.79 (dd, J=8.2, 2.2 Hz, 1H), 6.65 (d, J=3.4 Hz, 1H), 2.54 (t, J=7.6 Hz, 2H), 1.61 (sext., J=7.6 Hz, 2H), 0.95 (t, J=7.6 Hz, 3H); $^{13}$C NMR (125 MHz, CD$_3$OD) δ 168.4, 157.2, 141.6, 139.6, 132.0, 125.2, 111.2, 108.8, 106.9, 32.9, 24.7, 14.7.

*2-isopropyl-5-(thiazol-2-ylamino)phenol (jrII-137a)

Following the general procedure for the synthesis of 2-R-5-(thiazol-2-ylamino)phenol, 2-bromothiazole (0.40 mL, 4.48 mmol), 5-amino-2-isopropylphenol (339 mg, 2.24 mmol) and 37% HCl solution (0.37 mL, 4.48 mmol) in 10% aqueous EtOH solution (10 mL) was stirred at 90° C. for 24 h. The title compound was obtained after purification by flash chromatography on silica gel (hexane:EtOAc 7/3) in 69% yield (360 mg).

$^1$H NMR (500 MHz, CD$_3$OD) δ 7.16 (d, J=3.7 Hz, 1H), 7.07 (d, J=8.3 Hz, 1H), 7.03 (d, J=2.3 Hz, 1H), 6.82 (dd, J=8.3, 2.3 Hz, 1H), 6.67 (d, J=3.7 Hz, 1H), 3.25 (sept., J=6.9 Hz, 1H), 1.21 (d, J=6.9 Hz, 6H); $^{13}$C NMR (125 MHz, CD$_3$OD) δ 168.4, 156.5, 141.2, 139.6, 131.1, 128.0, 111.3, 108.8, 106.9, 28.1, 23.6.

General Procedure for the Synthesis of Thiourea Derivatives 5

Amino derivative 2 (1 equiv) was taken in a round-bottomed flask fitted with condenser and a mixture of 37% HCl aqueous (1 equiv) and H$_2$O (4.0 M) was added and then it was heated for about 1 h. The solution of aniline hydrochloride derivative obtained was cooled down to room temperature and ammonium thiocyanate (1 equiv) was added. The reaction mixture was refluxed for 3 h. The solid separated out on cooling was filtered, washed with H$_2$O and dried under high vacuum.

*3-Hydroxyphenylthiourea (jr-189)

Following the general procedure for the synthesis of thiourea derivatives 5,3-aminophenol (500 mg, 4.6 mmol) and 37% HCl (0.41 mL, 4.6 mmol) in H$_2$O (1.2 mL) were heated for about 1 h. The solution of aniline hydrochloride derivative obtained was cooled down to room temperature and ammonium thiocyanate (349 mg) was added. The reaction mixture was refluxed for 3 h and the title compound was obtained by filtration in 42% yield (325 mg).

$^1$H NMR (500 MHz, DMSO) δ 9.57 (s, 1H), 9.45 (br s, 1H), 7.90-7.00 (br s, 2H), 7.09 (t, J=8.0 Hz, 1H), 6.87 (s, 1H), 6.76 (d, J=8.0 Hz, 1H), 6.52 (dd, J=8.0, 2.0 Hz, 1H); $^{13}$C NMR (125 MHz, DMSO) δ 181.1, 158.0, 140.3, 129.8, 113.8, 112.0, 110.3.

*1-(3-hydroxy-4-methylphenyl)thiourea (jr-167/jrIII-26)

Following the general procedure for the synthesis of thiourea derivatives 5,5-amino-o-cresol (1 g, 8.1 mmol) and 37% HCl (0.72 mL, 8.1 mmol) in H$_2$O (2.0 mL) were heated for about 1 h. The solution of aniline hydrochloride derivative obtained was cooled down to room temperature and ammonium thiocyanate (618 mg) was added. The reaction mixture was refluxed for 3 h and the title compound was obtained by filtration in 35% yield (478 mg).

$^1$H NMR (400 MHz, DMSO) g 9.49 (s, 1H), 9.39 (br s, 1H), 7.90-7.00 (br s, 2H), 6.98 (t, J=8.0 Hz, 1H), 6.83 (s, 1H), 6.63 (dd, J=8.0, 1.6 Hz, 1H), 2.06 (s, 3H); $^{13}$C NMR (125 MHz, DMSO) δ186.3, 161.2, 140.3, 136.3, 120.1, 118.3, 116.2, 20.9.

*1-(3-hydroxy-4-methoxyphenyl)thiourea (jr-197)

Following the general procedure for the synthesis of thiourea derivatives 5,5-amino-2-methoxyphenol (500 mg, 3.6 mmol) and 37% HCl (0.32 mL, 3.6 mmol) in H$_2$O (0.9 mL) were heated for about 1 h. The solution of aniline hydrochloride derivative obtained was cooled down to room temperature and ammonium thiocyanate (273 mg) was added. The reaction mixture was refluxed for 3 h and the title compound was obtained by filtration in 54% yield (387 mg).

¹H NMR (500 MHz, DMSO) g 9.41 (s, 1H), 9.12 (br s, 1H), 8.86-8.00 (br s, 2H), 6.85 (d, J=8.6 Hz, 1H), 6.78 (s, 1H), 6.66 (d, J=8.6 Hz, 1H); ¹³C NMR (125 MHz, DMSO) δ 181.1, 146.9, 145.6, 132.2, 115.0, 112.7, 112.3, 56.2.

General Procedure for the Synthesis of Derivatives 6 and 7.

A solution containing thiourea derivative 5 (1 equiv) and the corresponding α-halocarbonyl compound (bromoacetone or ethyl 3-bromopyruvate) (1 equiv) in dry DMF (0.25 M) was heated at 60° C. for 6 h. The reaction mixture was diluted with ethyl acetate and washed with brine and saturated NaHCO₃ solution and the combined organic layers were dried (Na₂SO₄) and concentrated. The crude product was purified by flash chromatography on silica gel.

*3-(4-Methylthiazol-2-ylamino)phenol (jr-195a)

Following the general procedure for the synthesis of derivatives 6 and 7, a solution of 3-hydroxyphenylthiourea (100 mg, 0.59 mmol) and bromoacetone (98 mg, 0.71 mmol) in dry DMF (2.4 mL) was heated at 60° C. for 6 h. The title compound was obtained after purification by flash chromatography on silica gel (hexane:EtOAc 6/4) in 61% yield (74 mg).

¹H NMR (500 MHz, CD₃OD) δ 7.10 (t, J=8.1 Hz, 1H), 7.08 (t, J=2.2 Hz, 1H), 6.86 (dd, J=8.1, 2.2 Hz, 1H), 6.45 (dd, J=8.1, 2.2 Hz, 1H), 6.27 (s, 1H), 2.25 (s, 3H); ¹³C NMR (125 MHz, CD₃OD) δ 167.0, 159.7, 149.8, 144.1, 131.3, 110.7, 110.6, 106.4, 103.4, 17.7.

*2-Methyl-5-(4-methylthiazol-2-ylamino)phenol (jr-181a)

Following the general procedure for the synthesis of derivatives 6 and 7, a solution of 1-(3-hydroxy-4-methylphenyl)thiourea (100 mg, 0.59 mmol) and bromoacetone (96 mg, 0.71 mmol) in dry DMF (2.4 mL) was heated at 60° C. for 6 h. The title compound was obtained, after purification by flash chromatography on silica gel (hexane:EtOAc 6/4) in 61% yield (79 mg).

¹H NMR (500 MHz, CD₃OD) δ 7.04 (d, J=2.1 Hz, 1H), 6.98 (d J=8.1 Hz, 1H), 6.74 (dd, J=8.1, 2.1 Hz, 1H), 6.23 (s, 1H), 2.24 (s, 3H), 2.15 (s, 3H); ¹³C NMR (125 MHz, CD₃OD) δ 167.7, 157.3, 149.6, 141.7, 132.4, 120.3, 111.2, 106.7, 103.0, 17.6, 16.1.

*2-Methoxy-5-(4-methylthiazol-2-ylamino)phenol (jr-204a)

Following the general procedure for the synthesis of derivatives 6 and 7, a solution of 1-(3-hydroxy-4-methoxyphenyl)thiourea (100 mg, 0.50 mmol) and bromoacetone (83 mg, 0.60 mmol) in dry DMF (2.0 mL) was heated at 60° C. for 6 h. The title compound was obtained after purification by flash chromatography on silica gel (hexane:EtOAc 6/4) in 26% yield (30 mg).

¹H NMR (500 MHz, CD₃OD) δ 7.02 (d, J=2.4 Hz, 1H), 6.88 (d, J=8.6 Hz, 1H), 6.85 (d, J=8.6, 2.4 Hz, 1H), 6.21 (s, 1H), 3.84 (s, 3H), 2.23 (s, 3H); ¹³C NMR (125 MHz, CD₃OD) δ 168.5, 149.7, 148.6, 145.5, 137.0, 114.1, 111.8, 108.9, 102.7, 57.3, 17.6.

*Ethyl 2-(3-hydroxyphenylamino)thiazole-4-carboxylate (jr-196a)

Following the general procedure for the synthesis of derivatives 6 and 7, a solution of 3-hydroxyphenylthiourea (150 mg, 0.89 mmol) and ethyl 3-bromopyruvate (0.11 mL, 0.89 mmol) in dry DMF (3.6 mL) was heated at 60° C. for 6 h. The title compound was obtained after purification by flash chromatography on silica gel (hexane:EtOAc 6/4) in 81% yield (189 mg).

¹H NMR (500 MHz, CD₃OD) δ 7.57 (s, 1H), 7.18 (s, 1H), 7.12 (t, J=8.1 Hz, 1H), 6.95 (d, J=8.0 Hz, 1H), 6.50 (dd, J=8.0, 1.3 Hz, 1H), 4.31 (q, J=7.1 Hz, 2H), 1.34 (t, J=7.1 Hz, 3H); ¹³C NMR (125 MHz, CD₃OD) δ 166.6, 163.6, 159.7, 144.4, 143.5, 131.5, 119.1, 111.2, 110.9, 106.7, 62.7, 15.1.

*Ethyl 2-(3-hydroxy-4-methylphenylamino)thiazole-4-carboxylate (jr-168a)

Following the general procedure for the synthesis of derivatives 6 and 7, a solution of 1-(3-hydroxy-4-methylphenyl)thiourea (100 mg, 0.59 mmol) and ethyl 3-bromopyruvate (0.074 mL, 0.59 mmol) in dry DMF (2.4 mL) was heated at 60° C. for 6 h. The title compound was obtained after purification by flash chromatography on silica gel (hexane:EtOAc 6/4) in 65% yield (105 mg).

¹H NMR (500 MHz, CD₃OD) δ 7.60 (s, 1H), 7.20 (d J=2.2 Hz, 1H), 7.02 (d, J=8.1 Hz, 1H), 6.81 (dd, J=8.1, 2.2 Hz, 1H), 4.36 (q, J=7.1 Hz, 2H), 2.16 (s, 3H), 1.39 (t, J=7.1 Hz, 3H); ¹³C NMR (125 MHz, CD₃OD) δ 167.3, 163.6, 157.4, 144.4, 141.2, 132.4, 120.7, 118.5, 111.1, 106.8, 62.6, 16.0, 15.0.

*Ethyl 2-(3-hydroxy-4-methoxyphenylamino)thiazole-4-carboxylate (jr-205a)

Following the general procedure for the synthesis of derivatives 6 and 7, a solution of 1-(3-hydroxy-4-methoxyphenyl)thiourea (150 mg, 0.76 mmol) and ethyl 3-bromopyruvate (0.095 mL, 0.76 mmol) in dry DMF (3.0 mL) was heated at 60° C. for 6 h. The title compound was obtained after purification by flash chromatography on silica gel (hexane:EtOAc 6/4) in 63% yield (139 mg).

¹H NMR (500 MHz, CD₃OD) δ 7.53 (s, 1H), 7.06 (d, J=2.6 Hz, 1H), 6.95 (dd, J=8.7, 2.6 Hz, 1H), 6.78 (d, J=8.7 Hz, 1H), 4.32 (q, J=7.1 Hz, 2H), 3.82 (s, 3H), 1.35 (t, J=7.1 Hz, 3H); ¹³C NMR (125 MHz, CD₃OD) δ 168.1, 163.6, 148.6, 145.8, 144.4, 136.7, 118.4, 114.0, 112.0, 109.0, 62.6, 57.3, 15.1.

General Procedure for O-alkylation.

Method A.

A mixture of 2-R-5-(thiazol-2-ylamino)phenol 3 (1 equiv) and K₂CO₃ (1.1 equiv) in acetone (0.1 M) was treated with 4-bromo-2-methyl-2-butene (1 equiv). The reaction mixture was heated at reflux for 4 h. The reaction mixture was diluted with EtOAc and washed with 5% aqueous NaOH solution and brine. The organic phase was dried over Na₂SO₄, concentrated and the crude product was purified by flash chromatography on silica gel. Di-alkylated product was always obtained as secondary product.

Method B.

A mixture of 2-R-5-(thiazol-2-ylamino)phenol 3 (1 equiv) and Cs₂CO₃ (1 equiv) in acetone (0.1 M) was treated with the corresponding bromide derivative (1 equiv) at room temperature. After 2-4-h, the reaction mixture was diluted with EtOAc and washed with 5% aqueous NaOH solution and brine. The organic phase was dried over Na₂SO₄, concentrated and the crude product was purified by flash chromatography on silica gel.

Method C.

2-R-5-(thiazol-2-ylamino)phenol 3 (1 equiv), alcohol derivative (1.05 equiv), Ph₃P (1.05 equiv) were suspended in THF (3.0 M). The reaction flask was lowered into a sonication bath and sonicated for several minutes giving a clear and highly viscous solution. While sonication, DEAD (1.05 equiv) was added slowly. After 1 h, the reaction mixture was concentrated in vacuo and the crude product was purified by flash chromatography on silica gel.

*N-(3-(3-methylbut-2-enyloxy)phenylthiazol)-2-amine. JLJ000003 (Procedure jr-187/datas jr-20a)

Following the procedure general for O-allylation, Method A, a mixture of 3-(thiazol-2-ylamino)phenol (150 mg, 0.64 mmol) and $K_2CO_3$ (97 mg, 0.70 mmol) in acetone (6.4 mL) was treated with 4-bromo-2-methyl-2-butene (0.09 mL, 0.76 mmol). The reaction mixture was heated at reflux for 4 h. The title compound was obtained after purification by flash chromatography on silica gel (hexane:EtOAc 8/2) in 40% yield (78 mg) and di-alkylated product in 7% yield (20 mg).
$^1$H NMR (400 MHz, CDCl$_3$) δ 8.84~8.78 (br s, 1H), 7.31 (d, J=3.6 Hz, 1H), 7.25 (t, J=8.1 Hz, 1H), 6.96 (t, J=2.2 Hz, 1H), 6.91-6.87 (m; 1H), 6.63 (d, J=3.6 Hz, 1H), 6.64-6.62 (m, 1H), 5.51 (tm, J=6.7 Hz, 1H), 4.53 (d, J=6.7 Hz, 2H), 1.81 (s, 3H), 1.75 (s, 3H); $^{13}$C NMR (100 MHz, CDCl$_3$) δ 165.8, 159.9, 141.8, 138.4, 130.2, 119.5, 110.3, 109.1, 107.4, 104.5, 64.8, 25.9, 18.2; MS (FAB) m/z (rel intensity) 262 (17), 261 ([M$^{+1}$], 84), 260 (24), 221 (22), 194 (14), 193 (100), 192 (35), 69 (25); HRMS (FAB) calcd. for $C_{14}H_{16}N_2OS$ [M$^+$] 260.3554, found 261.1054.

*N-(4-methyl-3-(3-methylbut-2-enyloxy)phenylthiazol)-2-amine. JLJ000026 (jr-177b)

Following the procedure general for O-alkylation, Method A, a mixture of 2-methyl-5-(thiazol-2-ylamino)phenol (80 mg, 0.39 mmol) and $K_2CO_3$. (59 mg, 0.43 mmol) in acetone (3.9 mL) was treated with 4-bromo-2-methyl-2-butene (0.07 mL, 0.58 mmol). The reaction mixture was heated at reflux for 4 h. The title compound was obtained after purification by flash chromatography on silica gel (hexane:EtOAc 7/3) in 62% yield (66 mg) and di-alkylated product in 26% yield (34 mg).
$^1$H NMR (500 MHz, CDCl$_3$) δ 9.50~8.40 (br s, 1H), 7.29 (d, J=3.6 Hz, 1H), 7.11 (d, J=8.0 Hz, 1H), 6.89 (d, J=2.0 Hz, 1H), 6.83 (dd, J=8.0, 2.0 Hz, 1H), 6.58 (d, J=3.6 Hz, 1H), 5.52 (tm, J=6.4 Hz, 1H), 4.54 (d, J=6.4 Hz, 2H), 2.21 (s, 3H), 1.81 (s, 3H), 1.78 (s, 3H); $^{13}$C NMR (125 MHz, CDCl$_3$) δ 167.2, 157.7, 139.7, 138.3, 137.4, 131.0, 122.0, 120.1, 110.4, 106.6, 103.0, 65.2, 25.8, 18.3, 15.8; MS (FAB) m/z (rel intensity) 276 (20), 275 ([M$^+$], 100), 274 (45), 208 (16), 207 (99), 206 (44), 102 (23), 69 (48); HRMS (FAB) calcd. for $C_{15}H_{18}N_2OS$ [M$^+$] 274.3822, found 275.1217.

*N-(4-methoxy-3-(3-methylbut-2-enyloxy)phenylthiazol)-2-amine. JLJ000038 (jr-206a)

Following the procedure general for O-alkylation, Method A, a mixture of 2-methoxy-5-(thiazol-2-ylamino)phenol (150 mg, 0.68 mmol) and $K_2CO_3$ (103 mg, 0.74 mmol) in acetone (6.7 mL) was treated with 4-bromo-2-methyl-2-butene (0.09 mL, 0.68 mmol). The reaction mixture was heated at reflux for 4 h. The title compound was obtained after purification by flash chromatography on silica gel (hexane:EtOAc 7/3) in 39% yield (77 mg).
$^1$H NMR (500 MHz, CDCl$_3$) g 9.66~9.28 (br s, 1H), 7.28 (d, J=3.6 Hz, 1H), 6.96 (d, J=2.3 Hz, 1H), 6.90 (dd, J=8.5, 2.3 Hz, 1H), 6.85 (d, J=8.6 Hz, 1H), 6.52 (d, J=3.6 Hz, 1H), 5.52 (tm, J=6.6 Hz, 1H), 4.58 (d, J=6.6 Hz, 2H), 3.86 (s, 3H), 1.71 (s, 3H), 1.68 (s, 3H); $^{13}$C NMR (125 MHz, CDCl$_3$) δ 168.2, 148.9, 146.0, 138.3, 137.8, 134.6, 119.8, 112.2, 111.7, 106.3, 65.8, 56.2, 25.8, 18.3; MS (FAB) m/z (rel intensity) 292 (13), 291 ([M$^+$], 65), 290 (34), 224 (14), 223 (100), 222 (35), 207 (12), 69 (21); HRMS (FAB) calcd. for $C_{15}H_{18}N_2O_2S$ [M$^+$] 290.3812, found 291.1161.

*N-(4-chloro-3-(3-methylbut-2-enyloxy)phenylthiazol)-2-amine. JLJ000047 (jrII-135a)

Following the procedure general for O-alkylation, Method B, a mixture of 2-chloro-5-(thiazol-2-ylamino)phenol (100 mg, 0.44 mmol) and $Cs_2CO_3$ (144 mg, 0.44 mmol) in acetone (4.4 mL) was treated with 4-bromo-2-methyl-2-butene (0.05 mL, 0.44 mmol) at room temperature for 2 h. The title compound was obtained after purification by flash chromatography on silica gel (hexane:EtOAc 7/3) in 69% yield (89 mg).
$^1$H NMR (500 MHz, CD$_3$OD) g 7.50 (d, J=2.4 Hz, 1H), 7.25 (s, 1H), 7.23 (d, J=3.7 Hz, 1H), 7.00 (dd, J=8.6, 2.4 Hz, 1H), 6.80 (d, J=3.7 Hz, 1H), 5.51 (tm, J=6.6 Hz, 1H), 4.64 (d, J=6.6 Hz, 2H), 1.81 (s, 3H), 1.79 (s, 3H); $^{13}$C NMR (125 MHz, CD$_3$OD) δ 166.9, 156.4, 142.9, 139.9, 139.6, 131.4, 121.2, 116.7, 111.7, 109.8, 105.3, 67.3, 26.3, 18.7; MS (FAB) m/z (rel intensity) 296 (15), 295 ([M$^+$], 43), 255 (17), 228 (23), 227 (100), 226 (34), 69 (51), 57 (19), 55 (20); HRMS (FAB) calcd. for $C_{14}H_{15}ClN_2OS$ [M$^+$] 1294.8005, found 295.0677.

*N-(4-ethyl-3-(3-methylbut-2-enyloxy)phenylthiazol)-2-amine. JLJ000048 (jrII-142a)

Following the procedure general for O-alkylation, Method B, a mixture of 2-ethyl-5-(thiazol-2-ylamino)phenol (78 mg, 0.36 mmol) and $Cs_2CO_3$ (116 mg, 0.36 mmol) in acetone (3.6 mL) was treated with 4-bromo-2-methyl-2-butene (0.04 mL, 0.36 mmol) at room temperature for 3 h. The title compound was obtained after purification by flash chromatography on silica gel (hexane:EtOAc 8/2) in 48% yield (49 mg).
$^1$H NMR (400 MHz, CDCl$_3$) δ 8.67~8.58 (br s, 1H), 7.28 (d, J=3.6 Hz, 1H), 7.11 (d, J=8.0 Hz, 1H), 6.89 (d, J=1.9 Hz, 1H), 6.84 (dd, J=8.0, 1.9 Hz, 1H), 6.59 (d, J=3.6 Hz, 1H), 5.50 (br t, J=6.3 Hz, 1H), 4.54 (d, J=6.4 Hz, 2H), 2.62 (q, J=7.5 Hz, 1H), 1.80 (s, 3H), 1.74 (s, 31-1), 1.19 (t, J=7.5 Hz, 6H); $^{13}$C NMR (100 MHz, CDCl$_3$) δ 166.6, 157.3, 139.4, 138.5, 137.4, 129.4, 128.1, 120.0, 110.3, 107.0, 102.9, 65.1, 25.8, 22.8, 18.3, 14.2; MS (FAB) m/z (rel intensity) 290 (22), 289 ([M$^+$], 97), 288 (48), 249 (17), 222 (18), 221 (100), 220 (41), 205 (14), 69 (17); HRMS (FAB) calcd. for $C_{16}H_{20}N_2OS$ [M$^+$] 288.4090, found 289.1370.

*N-(4-propyl-3-(3-methylbut-2-enyloxy)phenylthiazol)-2-amine. JLJ000054 (jrII-170a)

Following the procedure general for O-alkylation, Method B, a solution of 2-propyl-5-(thiazol-2-ylamino)phenol (110 mg, 0.47 mmol) and $Cs_2CO_3$ (153 mg, 0.47 mmol) in acetone (4.7 mL) was treated with 4-bromo-2-methyl-2-butene (0.055 mL, 0.47 mmol) at room temperature for 4 h. The title compound was obtained after purification by flash chromatography on silica gel (hexane:EtOAc 8/2) in 56% yield (79 mg).
$^1$H NMR (500 MHz, CDCl$_3$) δ 9.29~9.17 (br s, 1H), 7.29 (d, J=3.4 Hz, 1H), 7.10 (d, J=8.0 Hz, 1H), 6.89 (d, J=1.9 Hz, 1H), 6.84 (dd, J=8.0, 1.9 Hz, 1H), 6.58 (d, J=3.4 Hz, 1H), 5.50 (br t, J=6.3 Hz, 1H), 4.54 (d, J=6.6 Hz, 2H), 2.57 (t, J=7.6 Hz, 2H), 1.80 (s, 3H), 1.74 (s, 3H), 1.61 (sext., J=7.6 Hz, 2H), 0.95 (t, J=7.6 Hz, 3H); $^{13}$C NMR (125 MHz, CDCl$_3$) δ 167.0, 157.4, 139.6, 138.3, 137.2, 130.3, 126.5, 120.1, 110.2, 106.7, 102.9, 65.1, 31.8, 25.8, 23.0, 18.3, 14.1; MS (FAB) m/z (rel intensity) 304 (24), 303 ([M+], 100), 302 (47), 263 (17), 236 (16), 235 (91), 234 (36), 205 (20), 69 (18); HRMS (FAB) calcd. for $C_{17}H_{22}N_2OS$ [M+] 302.4358, found 303.1535.

*N-(4-isopropyl-3-(3-methylbut-2-enyloxy)phenylthiazol)-2-amine. JLJ000049 (jrII-143a)

Following the procedure general for O-alkylation, Method B, a mixture of 2-isopropyl-5-(thiazol-2-ylamino)phenol (85 mg, 0.36 mmol) and $Cs_2CO_3$ (118 mg, 0.36 mmol) in acetone (3.6 mL) was treated with 4-bromo-2-methyl-2-butene (0.042 mL, 0.36 mmol) at room temperature for 2 h. The title compound was obtained after purification by flash chromatography on silica gel (hexane:EtOAc 8/2) in 49% yield (54 mg).
$^1$H NMR (400 MHz, $CDCl_3$) δ 9.32~9.21 (br s, 1H), 7.30 (d, J=3.6 Hz, 1H), 7.18 (d, J=7.9 Hz, 1H), 6.89 (s, 1H), 6.89 (dd, J=7.9, 3.6 Hz, 1H), 6.59 (d, J=3.6 Hz, 1H), 5.51 (tm, J=6.4 Hz, 1H), 4.54 (d, J=6.4 Hz, 2H), 3.30 (sept., J=6.9 Hz, 1H), 1.80 (s, 3H), 1.74 (s, 3H), 1.21 (d, J=6.9 Hz, 61-1); $^{13}$C NMR (100 MHz, $CDCl_3$) δ 166.8, 156.8, 139.3, 138.3, 137.4, 132.4, 126.7, 120.1, 110.3, 106.7, 102.9, 65.2, 26.5, 25.8, 22.8, 18.3; MS (FAB) m/z (rel intensity) 304 (25), 303 ([M+], 100), 302 (51), 236 (17), 235 (93), 234 (39), 219 (26), 69 (19); HRMS (FAB) calcd. for $C_{17}H_{22}N_2OS$ [M+] 302.4358, found 303.1529.

*N-(4-cyano-3-(3-methylbut-2-enyloxy)phenylthiazol)-2-amine. JLJ000053 (jrII-156b)

Following the procedure general for O-alkylation, Method B, a mixture of 2-hydroxy-4-(thiazol-2-ylamino)benzonitrile (60 mg, 0.28 mmol) and $Cs_2CO_3$ (90 mg, 0.28 mmol) in acetone (3.0 mL) was treated with 4-bromo-2-methyl-2-butene (0.032 mL, 0.28 mmol) at room temperature for 4 h. The title compound was obtained after purification by flash chromatography on silica gel (hexane:EtOAc 8/2) in 49% yield (38 mg).
$^1$H NMR (400 MHz, $CDCl_3$) δ 9.15~9.07 (br s, 1H), 7.47 (d, J=8.2 Hz, 1H), 7.38 (d, J=3.5 Hz, 1H), 7.24 (d, J=1.5 Hz, 1H), 6.87 (dd, J=8.2, 1.5 Hz, 1H), 6.80 (d, J=3.5 Hz, 1H), 5.47 (br t, J=6.3 Hz, 1H), 4.66 (d, J=6.5 Hz, 2H), 1.78 (s, 3H), 1.75 (s, 3H); $^{13}$C NMR (100 MHz, $CDCl_3$) δ 163.4, 162.1, 145.8, 139.0, 138.6, 134.7, 118.6, 117.1, 109.6, 108.9, 100.6, 94.6, 66.0, 25.8, 18.4; MS (FAB) m/z (rel intensity) 287 (19), 286 ([M+], 100), 275 (53), 274 (26), 218 (45), 217 (21), 207 (61), 206 (24), 69 (32), 57 (10), 55 (10); HRMS (FAB) calcd. for $C_{15}H_{15}N_3OS$ [M+] 285.3645, found 286.1018.

*4-Methyl-N-(3-(3-methylbut-2-enyloxy)phenyl)thiazol-2-amine. JLJ000035 (jr-202b)

Following the procedure general for O-alkylation, Method A, a mixture of 3-(4-methylthiazol-2-ylamino)phenol (74 mg, 0.36 mmol) and $K_2CO_3$ (55 mg, 0.39 mmol) in acetone (3.6 mL) was treated with 4-bromo-2-methyl-2-butene (0.05 mL, 0.43 mmol). The reaction mixture was heated at reflux for 4 h. The title compound was obtained after purification by flash chromatography on silica gel (hexane:EtOAc 7/3) in 59% yield (58 mg).
$^1$H NMR (500 MHz, $CDCl_3$) δ 8.86~8.00 (br s, 1H), 7.22 (t, J=8.1 Hz, 1H), 6.93 (t, J=2.2 Hz, 1H), 6.86 (dd, J=8.1, 2.2 Hz, 1H), 6.62 (dd, J=8.1, 2.2 Hz, 1H), 6.17 (s, 1H), 5.50 (tm, J=6.7 Hz, 1H), 4.51 (d, J=6.7 Hz, 2H), 2.29 (s, 3H), 1.79 (s, 3H), 1.74 (s, 3H); $^{13}$C NMR (100 MHz, $CDCl_3$) δ 165.2, 159.9, 148.3, 141.7, 138.3, 130.1, 119.5, 110.8, 109.2, 104.9, 101.8, 64.8, 25.9, 18.2, 17.7; MS (FAB) m/z (rel intensity) 276 (19), 275 ([M+], 96), 274 (46), 235 (23), 208 (15), 207 (100), 206 (54), 69 (15); HRMS (FAB) calcd. for $C_{15}H_{18}N_2OS$ [M+] 274.3822, found 275.1223.

*4-Methyl-N-(4-methyl-3-(3-methylbut-2-enyloxy)phenyl)thiazol-2-amine JLJ000027 (jr-186b)

Following the procedure general for O-alkylation, Method A, a mixture of 2-methyl-5-(4-methylthiazol-2-ylamino)phenol (79 mg, 0.36 mmol) and $K_2CO_3$ (54 mg, 0.39 mmol) in acetone (3.6 mL) was treated with 4-bromo-2-methyl-2-butene (0.05 mL, 0.43 mmol). The reaction mixture was heated at reflux for 4 h. The title compound was obtained after purification by flash chromatography on silica gel (hexane:EtOAc 7/3) in 56% yield (57 mg).
$^1$H NMR (500 MHz, $CDCl_3$) δ 8.90~8.10 (br s, 1H), 7.08 (d, J=7.9 Hz, 1H), 6.86 (d, J=2.1 Hz, 1H), 6.78 (dd, J=7.9, 2.1 Hz, 1H), 6.12 (s, 1H), 5.50 (tm, J=6.5 Hz, 1H), 4.52 (d, J=6.5 Hz, 2H), 2.27 (s, 3H), 2.20 (s, 3H), 1.80 (s, 3H), 1.73 (s, 3H); $^{13}$C NMR (125 MHz, $CDCl_3$) δ 166.6, 157.6, 148.3, 139.5, 137.4, 131.0, 122.3, 120.1, 111.2, 103.7, 101.1, 65.1, 25.8, 18.3, 17.4, 15.8; MS (FAB) m/z (rel intensity) 290 (23), 289 ([M+], 100), 288 (67), 249 (16), 222 (16), 221 (86), 220 (57), 69 (12); HRMS (FAB) calcd. for $C_{16}H_{20}N_2OS$ [M+] 288.4090, found 289.1371.

*4-Methyl-N-(4-methoxy-3-(3-methylbut-2-enyloxy)phenyl)thiazol-2-amine. JLJ000039 (jr-210a)

Following the general procedure for O-alkylation, Method A, a mixture of 2-methoxy-5-(4-methylthiazol-2-ylamino)phenol (30 mg, 0.10 mmol) and $K_2CO_3$ (15 mg, 0.11 mmol) in acetone (1.0 mL) was treated with 4-bromo-2-methyl-2-butene (0.014 mL, 0.12 mmol). The reaction mixture was heated at reflux for 4 h. The title compound was obtained after purification by flash chromatography on silica gel (hexane:EtOAc 7/3) in 54% yield (16 mg).
$^1$H NMR (500 MHz, $CDCl_3$) δ 6.92 (s, 1H), 6.84 (s, 2H), 6.09 (s, 1H), 5.51 (tm, J=6.6 Hz, 1H), 4.57 (d, J=6.6 Hz, 2H), 3.86 (s, 3H), 2.24 (s, 3H), 1.77 (s, 3H), 1.72 (s, 3H); $^{13}$C NMR (125 MHz, $CDCl_3$) δ 167.2, 148.8, 148.5, 146.3, 137.9, 134.0, 119.7, 112.6, 112.1, 107.0, 101.1, 65.8, 56.2, 25.9, 23.0, 18.3, 17.4; MS (FAB) m/z (rel intensity) 306 (20), 305 ([M+], 92), 304 (63), 279 (28), 265 (16), 237 (100), 167 (33), 113 (40), 69 (19), 59 (65), 57 (18); HRMS (FAB) calcd. for $C_{16}H_{20}N_2O_2S$ [M+] 304.4080, found 305.1327.

*Ethyl 2-(3-(3-methylbut-2-enyloxy)phenylamino)thiazole-4-carboxylate. JLJ000036 (jr-203b)

Following the general procedure for O-alkylation, Method A, a mixture of ethyl 2-(3-hydroxyphenylamino)thiazole-4-carboxylate (182 mg, 0.69 mmol) and $K_2CO_3$ (105 mg, 0.76 mmol) in acetone (6.9 mL) was treated with 4-bromo-2-methyl-2-butene (0.096 mL, 0.83 mmol). The reaction mixture was heated at reflux for 4 h. The title compound was obtained after purification by flash chromatography on silica gel (hexane:EtOAc 7/3) in 55% yield (127 mg).
$^1$H NMR (500 MHz, $CDCl_3$) δ 8.49 (br s, 1H), 7.52 (s, 1H), 7.24 (t, J=8.1 Hz, 1H), 6.91 (t, J=2.1 Hz, 1H), 6.87 (dd, J=8.1, 1.5 Hz, 1H), 6.66 (dd, J=8.1, 1.5 Hz, 1H), 5.49 (tm, J=6.7 Hz, 1H), 4.51 (d, J=6.7 Hz, 2H), 4.31 (q, J=7.1 Hz, 2H), 1.79 (s, 3H), 1.74 (s, 3H), 1.32 (t, J=7.1 Hz, 3H); $^{13}$C NMR (100 MHz, $CDCl_3$) δ 165.7, 161.5, 159.9, 142.9, 141.2, 138.5, 130.3, 119.4, 116.6, 111.3, 110.2, 105.7, 64.8, 61.2, 25.8, 18.2, 14.3; MS (FAB) m/z (rel intensity) 333 (52), 332 ([M$^{30}$], 6), 273 (11), 265 (43), 264 (31), 207 (11), 87 (14), 85 (22),

*Ethyl 2-(4-methyl-3-(3-methylbut-2-enyloxy)phenylamino)thiazole-4-carboxylate. JLJ000028 (jr-182b)

Following the general procedure for O-alkylation, Method A, a mixture of ethyl 2-(3-hydroxy-4-methylphenylamino)thiazole-4-carboxylate (80 mg, 0.29 mmol) and $K_2CO_3$ (44 mg, 0.32 mmol) in acetone (2.9 mL) was treated with 4-bromo-2-methyl-2-butene (0.037 mL, 0.32 mmol). The reaction mixture was heated at reflux for 4 h. The title compound was obtained after purification by flash chromatography on silica gel (hexane:EtOAc 7/3) in 57% yield (56 mg).
$^1$H NMR (500 MHz, CDCl$_3$) δ 8.32 (br s, 1H), 7.45 (s, 1H), 7.08 (d, J=7.9 Hz, 1H), 6.83 (d, J=2.0 Hz, 1H), 6.77 (dd, J=7.9, 2.0 Hz, 1H), 5.47 (tm, J=6.4 Hz, 1H), 4.51 (d, J=6.4 Hz, 2H), 4.29 (c, J=7.1 Hz, 2H), 2.19 (s, 3H), 1.78 (s, 3H), 1.72 (s, 3H), 1.31 (t, J=7.1 Hz, 3H); $^{13}$C NMR (125 MHz, CDCl$_3$) δ 166.9, 161.6, 157.8, 143.1, 138.8, 137.6, 131.1, 123.4, 120.0, 116.2, 111.7, 104.4, 65.2, 61.2, 25.8, 18.3, 15.9, 14.3; MS (FAB) m/z (rel intensity) 348 (23), 347 ([M$^+$], 100), 346 (20), 280 (18), 279 (93), 278 (69), 69 (14); HRMS (FAB) calcd. for $C_{18}H_{22}N_2O_3S$ [M$^+$] 346.4448, found 347.1434.

*Ethyl 2-(4-methoxy-3-(3-methylbut-2-enyloxy)phenylamino)thiazole-4-carboxylate. JLJ000040 (jr-211a)

Following the general procedure for O-alkylation, Method A, a mixture of ethyl 2-(3-hydroxy-4-methoxyphenylamino)thiazole-4-carboxylate (139 mg, 0.47 mmol) and $K_2CO_3$ (72 mg, 0.52 mmol) in acetone (4.7 mL) was treated with 4-bromo-2-methyl-2-butene (0.066 mL, 0.56 mmol). The reaction mixture was heated at reflux for 4 h. The title compound was obtained after purification by flash chromatography on silica gel (hexane:EtOAc 7/3) in 42% yield (71 mg).
$^1$H NMR (500 MHz, CDCl$_3$) δ 8.29 (br s, 1H), 7.41 (s, 1H), 6.90 (d, J=2.2 Hz, 1H), 6.86 (dd, J=8.5, 2.2 Hz, 1H), 6.83 (d, J=8.5 Hz, 1H), 5.49 (tm, J=6.6 Hz, 1H), 4.56 (d, J=6.6 Hz, 2H), 4.26 (q, J=7.2 Hz, 2H), 3.85 (s, 3H), 1.75 (s, 3H), 1.70 (s, 3H), 1.29 (t, J=7.2 Hz, 3H); $^{13}$C NMR (125 MHz, CDCl$_3$) δ 168.2, 161.6, 149.0, 147.1, 143.2, 138.0, 133.5, 119.6, 116.0, 113.7, 112.0, 108.0, 65.9, 61.1, 56.2, 25.9, 18.3, 14.3; MS (FAB) m/z (rel intensity) 364 (21), 363 ([M$^+$], 94), 362 (20), 296 (19), 295 (100), 294 (67), 69 (15); HRMS (FAB) calcd. for $C_{18}H_{22}N_2O_4S$ [M$^+$] 362.4438, found 363.1376.

*(2-3-(3-Methylbut-2-enyloxy)phenylamino)thiazol-4-yl)methanol. JLJ000037 (jr-207a)

A solution of the compound ethyl 2-(3-(3-methylbut-2-enyloxy)phenylamino)thiazole-4-carboxylate (129 mg, 0.39 mmol) in anhydrous THF (1.5 mL) was added to a suspension of LiAlH$_4$ (30 mg, 0.77 mmol) in dry THF (1 mL) cooled at 0° C. under nitrogen atmosphere. After 3 h, the reaction mixture was quenched with H$_2$O, filtrated, dried over MgSO$_4$ and concentrated. The crude product was purified by flash chromatography on silica gel (hexane:EtOAc 1/1) to afford the product (50 mg, 45% yield).
$^1$H NMR (500 MHz, CD$_3$OD) δ 7.24 (t, J=2.1 Hz, 1H), 7.18 (t, J=8.2 Hz, 1H), 7.01 (d, J=7.6 Hz, 1H), 6.60 (s, 1H), 6.55 (d, J=6.6 Hz, 1H), 5.48 (tm, J=6.6 Hz, 1H), 4.55 (s, 3H), 4.53 (d, J=6.6 Hz, 2H), 1.79 (s, 3H), 1.76 (s, 3H); $^{13}$C NMR (125 MHz, CD$_3$OD) δ 167.1, 161.5, 154.3, 144.0, 138.9, 131.2, 121.7, 111.6, 109.7, 105.9, 104.5, 66.2, 62.0, 26.3, 18.7; MS (FAB) m/z (rel intensity) 292 (20), 291 ([M$^+$], 98), 290 (42), 273 (100), 205 (30), 149 (15), 69 (27); HRMS (FAB) calcd. for $C_{15}H_{18}N_2O_2S$ [M$^+$]290.3812, found 291.1172.

*(2-(4-Methyl-3-(3-methylbut-2-enyloxy)phenylamino)thiazol-4-yl)methanol. JLJ000037 (jr-190a)

A solution of ethyl 2-(4-methyl-3-(3-methylbut-2-enyloxy)phenylamino)thiazole-4-carboxylate (52 mg, 0.15 mmol) in anhydrous THF (1 mL) was added to a suspension of LiAla$_4$ (9 mg, 0.22 mmol) in dry THF (1 mL) at 0° C. under nitrogen atmosphere. After 1 h 30 min, additional LiAlH$_4$ (9 mg, 0.22 mmol) was added. After 1 h, the reaction mixture was quenched with H$_2$O, filtrated, dried over MgSO$_4$ and concentrated. The crude product was purified by flash chromatography on silica gel (Hexane:EtOAc 1/1) to obtain the title compound (27 mg, 59% yield).
$^1$H NMR (500 MHz, CDCl$_3$) δ 8.45-7.80 (br s, 1H), 7.07 (d, J=7.9 Hz, 1H), 6.75 (s, 1H), 6.73 (dd, J=7.9, 2.1 Hz, 1H), 6.42 (s, 1H), 5.47 (tm, J=6.5 Hz, 1H), 4.57 (s, 2H), 4.47 (d, J=6.5 Hz, 2H), 2.18 (s, 3H), 1.78 (s, 31-1), 1.71 (s, 3.11); $^{13}$C NMR (125 MHz, CDCl$_3$) δ 167.3, 157.8, 152.0, 138.9, 137.6, 131.1, 122.8, 119.9, 111.0, 103.5, 103.0, 65.1, 60.5, 25.8, 18.3, 15.8; HRMS calcd. for CHNOS, found

*(2-(4-Methoxy-3-(3-methylbut-2-enyloxy)phenylamino)thiazol-4-yl)methanol. JLJ000041 (jr-215a)

A solution of ethyl 2-(4-methoxy-3-(3-methylbut-2-enyloxy)phenylamino)thiazole-4-carboxylate (67 mg, 0.18 mmol) in anhydrous THF (1 mL) was added to a suspension of LiAlH$_4$ (14 mg, 0.37 mmol) in dry THF (1 mL) at 0° C. under nitrogen atmosphere. After 3 h, the reaction mixture was quenched with H$_2$O, filtrated, dried over MgSO$_4$ and concentrated. The crude product was purified by flash chromatography on silica gel (hexane:EtOAc 1/1) to give the title compound (30 mg, 50% yield).
$^1$H NMR (500 MHz, CD$_3$OD) δ 7.21 (d, J=2.4 Hz, 1H), 7.01 (dd, J=8.6, 2.4 Hz, 1H), 6.91 (d, J=8.6 Hz, 1H), 6.54 (s, 1H), 5.51 (tm, J=6.7 Hz, 1H), 4.89 (s, 3H), 4.58 (d, J=6.7 Hz, 2H), 4.52 (s, 2H), 1.79 (s, 3H), 1.75 (s, 31-1); $^{13}$C NMR (125 MHz, CD$_3$OD) δ 168.5, 154.2, 150.4, 147.2, 139.3, 136.9, 121.6, 114.6, 112.7, 107.9, 103.8, 67.4, 61.9, 57.4, 26.3, 18.7; MS (FAB) m/z (rel intensity) 322 (17), 321 ([M$^+$], 78), 320 (43), 303 (60), 252 (60), 235 (26), 218 (18), 149 (35), 121 (100), 91 (28), 69 (34), 57 (17); HRMS (FAB) calcd. for $C_{16}H_{20}N_2O_3S$ [M$^+$] 320.4070, found 321.1272.

*N-(3-(Furan-2-ylmethoxy)-4-methylphenyl)thiazol-2-amine JLJ000055 (jrII-192a1)

Following the general procedure for O-alkylation, Method B, a mixture of 2-methyl-5-(thiazol-2-ylamino)phenol (100 mg, 0.48 mmol) and Cs$_2$CO$_3$ (158 mg, 0.48 mmol) in acetone (4.4 mL) was treated with a freshly prepared solution of 2-furylbromomethane in ether (0.85 mL, 0.44 mmol) at room temperature. After 2 h Cs$_2$CO$_3$ (150 mg, 0.46 mmol) was added and stirred for 5.5 h at rt. The title compound was obtained after purification by flash chromatography on silica gel (hexane:EtOAc 3/1) in 36% yield (50 mg).
$^1$H NMR (500 MHz, CDCl$_3$) δ 8.67~8.58 (br s, 1H), 7.45 (s, 1H), 7.28 (d, J=3.6 Hz, 1H), 7.11 (d, J=8.0 Hz, 1H), 7.05 (s, 1H), 6.84 (dd, J=8.0, 1.9 Hz, 1H), 6.60 (d, J=3.6 Hz, 1H), 6.44 (d, J=3.0 Hz, 1H), 6.39 (m, 1H), 5.02 (s, 2H), 2.19 (s, 31-1); $^{13}$C NMR (125 MHz, CDCl$_3$) δ 166.7, 157.2, 150.5, 143.0, 139.6, 138.5, 131.3, 122.4, 111.1, 110.5, 109.7, 107.0, 103.5, 63.0, 15.7; MS (FAB) m/z (rel intensity) 288 (14), 287 ([14], 72), 286 (39), 81 (100), 59 (14); HRMS (FAB) calcd. for $C_{15}H_{14}N_2O_2S$ [M⁺] 286.3496, found 287.0852.

*N-(4-Chloro-3-(furan-2-ylmethoxy)phenyl)thiazol-2-amine JLJ000056 (jrII-193a1)

Following the general procedure for O-alkylation, Method B, a mixture of 2-chloro-5-(thiazol-2-ylamino)phenol (100 mg, 0.44 mmol) and $Cs_2CO_3$ (152, 0.44 mmol) in acetone (4.4 mL) was treated with a freshly prepeared solution of 2-furylbromomethane in ether (0.75 mL, 0.44 mmol) at room temperature. Reaction control by TLC showed full conversion after 2 hrs. The title compound was obtained after purification by flash chromatography on silica gel (hexane:EtOAc 3/1) in 32% yield (43 mg).

$^1$H NMR (500 MHz, $CDCl_3$) δ 9.26~9.06 (br s, 1H), 7.45 (s, 1H), 7.31 (d, J=8.4 Hz, 1H), 7.31 (d, J=3.7 Hz, 1H), 7.24 (d, J=2.4 Hz, 1H), 6.88 (dd, J=8.4, 2.4 Hz, 1H), 6.66 (d, J=3.7 Hz, 1H), 6.48 (d, J=3.0 Hz, 1H), 6.38 (m, 1H), 5.10 (s, 2H); $^{13}$C NMR (125 MHz, $CDCl_3$) δ 165.2, 154.6, 149.6, 143.3, 140.3, 138.7, 130.7, 117.1, 111.5, 110.6, 110.5, 108.0, 105.0, 63.8; MS (FAB) m/z (rel intensity) 307 ([M⁺], 20), 306 (15), 81 (100); HRMS (FAB) calcd. for $C_{14}H_{11}ClN_2O_2S$ [M⁺] 306.7679, found 307.0308.

*N-(4-Cyano-3-(furan-2-ylmethoxy)$_p$ h enyl)thiazol-2-amine JLJ000057 (jrII-194b)

Following the general procedure for O-alkylation, Method B, a mixture of 2-hydroxy-4-(thiazol-2-ylamino)benzonitrile (70 mg, 0.32 mmol) and $Cs_2CO_3$ (105, 0.32 mmol) in acetone (4.4 mL) was treated with a freshly prepeared solution of 2-furylbromomethane in ether (0.60 mL, 0.32 mmol) at room temperature. Reaction control by TLC showed full conversion after 7.5 hrs. The title compound was obtained after purification by flash chromatography on silica gel (hexane:EtOAc 3/1) in 57% yield (54 mg).

$^1$H NMR (500 MHz, $CDCl_3$) δ 8.10-8.00 (br s, 1H), 7.56 (s, 1H), 7.48 (d, J=8.1 Hz, 1H), 7.44 (s, 1H), 7.39 (s, 1H), 6.87 (d, J=8.1 Hz, 1H), 6.81 (s, 1H), 6.55 (s, 1H), 6.38 (s, 1H), 5.17 (s, 2H); $^{13}$C NMR (125 MHz, $CDCl_3$) δ 161.5, 148.9, 145.4, 143.4, 139.1, 134.7, 116.8, 111.0, 110.7, 109.9, 109.4, 101.1, 95.1, 63.3; MS (FAB) m/z (rel intensity) 299 (13), 298 ([M⁺], 68), 273 (11), 218 (30), 84 (11), 81 (100); HRMS (FAB) calcd. for $C_{15}H_{11}N_3O_2S$ [M⁺] 297.3319, found 298.0649.

*N-(3-(Furan-3-ylmethoxy)-4-methylphenyl)thiazol-2-amine JLJ000058 (jrII-189a)

Following the general procedure for O-alkylation, Method B, a mixture of 2-methyl-5-(thiazol-2-ylamino)phenol (100 mg, 0.48 mmol) and $Cs_2CO_3$ (0.48 mmol) in acetone (4.4 mL) was treated with a freshly prepeared solution of 2-furylbromomethane in ether (0.53 mmol) at 0°. After 30 min the reaction was heated to RT. After 4 h, another 2-furylbromomethane (35 mg) were added and stirred for another 1.5 h. Reaction control by TLC showed full conversion after 6 h 40 min. The title compound was obtained after purification by flash chromatography on silica gel (hexane:EtOAc 3/1) in 54% yield (75 mg).

$^1$H NMR (500 MHz, $CDCl_3$) δ 9.62 (br s, 1H), 7.50 (s, 1H), 7.43 (s, 1H), 7.25 (d, J=3.4 Hz, 1H), 7.10 (d, J=7.9 Hz, 1H), 6.98 (s, 1H), 6.83 (d, J=7.9 Hz, 1H), 6.56 (d, J=3.4 Hz, 1H), 6.48 (s, 1H), 4.95 (s, 2H), 2.20 (s, 3H); $^{13}$C NMR (125 MHz, $CDCl_3$) δ 167.1, 157.4, 143.4, 140.5, 139.8, 138.3, 131.2, 122.0, 121.6, 110.8, 110.0, 106.7, 103.0, 62.3, 15.8; MS (FAB) m/z (rel intensity) 288 (18), 287 ([M⁺], 100), 286 (36), 81 (31); HRMS (FAB) calcd. for $C_{15}H_{14}N_2O_2S$ [M⁺] 286.3496, found 287.0852.

*N-(4-Chloro-3-(furan-3-ylmethoxy)phenyl)thiazol-2-amine JLJ000059 (jrII-190a)

Following the general procedure for O-alkylation, Method B, a mixture 2-chloro-5-(thiazol-2-ylamino)phenol (100 mg, 0.44 mmol) and $Cs_2CO_3$ (147 mg, 0.44 mmol) in acetone (4.4 mL) was treated with a freshly prepeared solution of 2-furylbromomethane in ether (125 mg, 0.48 mmol) at 0°. After 30 min the reaction was heated to RT. Reaction control by TLC showed full conversion after 5 h. The title compound was obtained after purification by flash chromatography on silica gel (hexane:EtOAc 3/1) in 62% yield (83 mg).

$^1$H NMR (500 MHz, $CDCl_3$) δ 8.91~8.86 (br s, 1H), 7.54 (s, 1H), 7.43 (s, 1H), 7.31 (d, J=8.5 Hz, 1H), 7.28 (d, J=3.6 Hz, 1H), 7.24 (d, J=2.4 Hz, 1H), 6.83 (dd, J=8.5, 2.4 Hz, 1H), 6.66 (d, J=3.6 Hz, 1H), 6.53 (s, 1H), 5.04 (s, 2H); $^{13}$C NMR (125 MHz, $CDCl_3$) δ 165.4, 154.7, 143.6, 140.9, 140.4, 138.6, 130.7, 120.8, 116.9, 111.3, 110.0, 107.9, 104.5, 63.3; MS (FAB) m/z (rel intensity) 308 (29), 307 ([M⁺], 90), 306 (39), 273 (14), 81 (100), 53 (7); HRMS (FAB) calcd. for $C_{14}H_{11}ClN_2O_2S$ [M⁺] 306.7679, found 307.0313.

*N-(4-Cyano-3-(furan-3-ylmethoxy)phenyl)thiazol-2-amine JLJ000060 (jrII-209a2bet)

Following the general procedure for O-alkylation, Method B, a mixture of 2-hydroxy-4-(thiazol-2-ylamino)benzonitrile (70 mg, 0.32 mmol) and $Cs_2CO_3$ (0.32 mmol) in acetone (4.4 mL) was treated with a freshly prepeared solution of 2-furylbromomethane in ether (71 mg, 0.32 mmol) at RT. Reaction control by TLC showed full conversion after 2 h. The title compound was obtained after purification by flash chromatography on silica gel (hexane:EtOAc 65/35) in 11% yield (10 mg).

$^1$H NMR (500 MHz, $CDCl_3$) δ 7.95~7.85 (br s, 1H), 7.59 (s, 1H), 7.55 (d, J=1.9 Hz, 1H), 7.47 (d, J=8.4 Hz, 1H), 7.43 (s, 1H), 7.38 (d, J=3.6 Hz, 1H), 6.81 (d, J=3.6 Hz, 1H), 6.80 (dd, J=8.4, 1.9 Hz, 1H), 6.55 (s, 1H), 5.12 (s, 2H); $^{13}$C NMR (125 MHz, $CDCl_3$) δ 162.7, 161.7, 145.5, 143.7, 141.1, 139.2, 134.6, 120.2, 116.8, 110.0, 109.9, 109.3, 100.9, 95.0, 63.0; MS (FAB) m/z (rel intensity) 299 (19), 298 ([M⁺], 100), 297 (12), 260 (16), 233 (15), 232 (98), 231 (17), 218 (31), 113 (13), 84 (13), 57 (12); HRMS (FAB) calcd. for $C_{15}H_{11}N_3O_2S$ [M⁺] 297.3319, found 298.0646.

*N-(4-Methyl-3-(thiophen-2-ylmethoxy)phenyl)thiazol-2-amine JLJ000072 (jrII-221a)

Following the general procedure for O-alkylation, Method B, a mixture of 2-methyl-5-(thiazol-2-ylamino)phenol (100 mg, 0.48 mmol) and $Cs_2CO_3$ (0.48 mmol) in acetone (4.4 mL) was treated with 2-thiophenebromomethane (0.48 mmol) at RT. Reaction control by TLC showed full conversion after 5.25 h. The title compound was obtained after purification by flash chromatography on silica gel (hexane:EtOAc 3/1) in 60% yield (87 mg).

$^1$H NMR (500 MHz, $CDCl_3$) δ 9.31~9.13 (br s, 1H), 7.32 (d, J=4.0 Hz, 1H), 7.25 (d, J=3.1 Hz, 1H), 7.12 (m, 2H), 7.00 (br s, 2H), 6.84 (d, J=7.7 Hz, 1H), 6.57 (d, J=3.2 Hz, 1H), 5.23 (s, 2H), 2.22 (s, 3H); $^{13}$C NMR (125 MHz, $CDCl_3$) δ 166.8, 157.1, 139.7, 139.6, 138.3, 131.2, 126.7, 126.2, 126.0, 122.2, 111.0, 106.8, 103.2, 66.4, 15.8.

*N-(4-Chloro-3-(thiophen-2-ylmethoxy)phenyl)thiazol-2-amine JLJ000073 (jrII-222a)

Following the general procedure for O-alkylation, Method B, a mixture of 2-chloro-5-(thiazol-2-ylamino)phenol (100 mg, 0.44 mmol) and $Cs_2CO_3$ (0.48 mmol) in acetone (4.4 mL) was treated with 2-thiophenebromomethane (0.44 mmol) at RT. Reaction control by TLC showed full conversion after 2.5 h. The title compound was obtained after purification by flash chromatography on silica gel (hexane:EtOAc 3/1) in 74% yield (105 mg).

$^1$H NMR (500 MHz, $CDCl_3$) δ 8.00 (br s, 1H), 7.34 (d, J=5.1 Hz, 1H), 7.31 (d, J=8.5 Hz, 1H), 7.29 (d, J=3.6 Hz, 1H), 7.27 (d, J=2.5 Hz, 1H), 7.15 (d, J=2.8 Hz, 1H), 7.01 (dd, J=5.1, 3.5 Hz, 1H), 6.85 (dd, J=8.5, 2.5 Hz, 1H), 6.67 (d, J=3.6 Hz, 1H), 5.33 (s, 2H); $^{13}$C NMR (125 MHz, $CDCl_3$) δ 165.6, 154.4, 140.4, 138.5, 138.4, 130.7, 127.0, 126.8, 126.4, 117.0, 111.5, 107.7, 104.9, 66.4.

*N-(4-Cyano-3-(thiophen-2-ylmethoxy)phenyl)thiazol-2-amine JLJ000074 (jrII-223a)

Following the general procedure for O-alkylation, Method B, a mixture of 2-hydroxy-4-(thiazol-2-ylamino)benzonitrile (70 mg, 0.32 mmol) and $Cs_2CO_3$ (105 mg, 0.32 mmol) in acetone (4.4 mL) was treated with 2-thiophenebromomethane (0.44 mmol) at RT. Reaction control by TLC showed full conversion after 3.0 h. The title compound was obtained after purification by flash chromatography on silica gel (hexane:EtOAc 3/1) in 23% yield (23 mg).

$^1$H NMR (500 MHz, $CDCl_3$) g 8.70~8.00 (br s, 1H), 7.50 (d, J=1.9 Hz, 1H), 7.47 (d, J=8.5 Hz, 1H), 7.37 (d, J=3.8 Hz, 1H), 7.33 (d, J=4.9 Hz, 1H), 7.19 (d, J=3.6 Hz, 1H), 7.00 (dd, J=4.9, 3.6 Hz, 1H), 6.85 (dd, J=8.5, 1.9 Hz, 1H), 6.80 (d, J=3.8 Hz, 1H), 5.38 (s, 2H); $^{13}$C NMR (125 MHz, $CDCl_3$) δ 162.9, 161.4, 145.6, 139.0, 137.7, 127.4, 126.9, 126.7, 116.8, 109.9, 109.5, 101.1, 95.0, 66.0.

*N-(4-Methyl-3-(thiophen-3-ylmethoxy)phenyl)thiazol-2-amine JLJ000061 (jrII-216a)

Following the general procedure for O-alkylation, Method B, a mixture of 2-methyl-5-(thiazol-2-ylamino)phenol (100 mg, 0.48 mmol) and $Cs_2CO_3$ (158 mg, 0.48 mmol) in acetone (4.4 mL) was treated with 2-thiophenebromomethane (0.48 mmol) at RT. Reaction control by TLC showed full conversion after 4.0 h. The title compound was obtained after purification by flash chromatography on silica gel (hexane:EtOAc 7/3) in 57% yield (82 mg).

$^1$H NMR (500 MHz, $CDCl_3$) δ 9.17~9.08 (br s, 1H), 7.35 (dd, J=5.0, 2.9 Hz, 1H), 7.31 (br s, 1H), 7.25 (d, J=3.5 Hz, 1H), 7.16 (d, J=5.0 Hz, 1H), 7.13 (d, J=8.2 Hz, 1H), 6.98 (d, J=1.8 Hz, 1H), 6.84 (dd, J=8.2, 1.8 Hz, 1H), 6.58 (d, J=3.5 Hz, 1H), 5.11 (s, 2H), 2.24 (s, 3H); $^{13}$C NMR (125 MHz, $CDCl_3$) δ 166.8, 157.4, 139.7, 138.4, 138.1, 131.2, 126.8, 126.2, 122.5, 122.0, 110.7, 106.9, 103.0, 65.9, 15.8; MS (FAB) m/z (rel intensity) 304 (22), 303 ([M$^+$], 100), 302 (40), 98 (20); HRMS (FAB) calcd. for $C_{15}H_{14}N_2OS_2$ [M$^+$] 302.4146, found 303.0623.

*N-(4-Chloro-3-(thiophen-3-ylmethoxy)phenyl)thiazol-2-amine JLJ000062 (jrII-217a)

Following the general procedure for O-alkylation, Method B, a mixture of 2-chloro-5-(thiazol-2-ylamino)phenol (100 mg, 0.44 mmol) and $Cs_2CO_3$ (147 mg, 0.44 mmol) in acetone (4.4 mL) was treated with 2-thiophenebromomethane (85 mg, 0.44 mmol) at RT. Reaction control by TLC showed full conversion after 4.0 h. The title compound was obtained after purification by flash chromatography on silica gel (hexane:EtOAc 7/3) in 62% yield (88 mg).

$^1$H NMR (500 MHz, $CDCl_3$) δ 8.95 (br s, 1H), 7.37~7.34 (m, 2H), 7.32 (d, J=8.5 Hz, 1H), 7.26 (d, J=3.1 Hz, 1H), 7.19 (d, J=4.4 Hz, 1H), 7.16 (d, J=1.9 Hz, 1H), 6.85 (dd, J=8.5, 1.9 Hz, 1H), 6.45 (d, J=3.1 Hz, 1H), 5.18 (s, 2H); $^{13}$C NMR (125 MHz, $CDCl_3$) δ 165.5, 154.7, 140.4, 138.5, 137.2, 130.7, 126.7, 126.4, 123.0, 116.8, 111.2, 107.8, 104.4, 67.0; FIRM MS (FAB) m/z (rel intensity) 323 (66), 322 ([M$^+$], 32), 97 (100), 57 (4); HRMS (FAB) calcd. for $C_{14}H_{11}ClN_2OS_2$ [M$^+$] 322.8329, found 322.0071.

*N-(4-Cyano-3-(thiophen-3-ylmethoxy)phenyl)thiazol-2-amine JLJ000063 (jrII-218b)

Following the general procedure for O-alkylation, Method B, a mixture of 2-hydroxy-4-(thiazol-2-ylamino)benzonitrile (70 mg, 0.32 mmol) and $Cs_2CO_3$ (105 mg, 0.32 mmol) in acetone (4.4 mL) was treated with 2-thiophenebromomethane (80 mg, 0.32 mmol) at RT. Reaction control by TLC showed full conversion after 4.5 h. The title compound was obtained after purification by flash chromatography on silica gel (hexane:EtOAc 1/1) in 13% yield (13 mg).

$^1$H NMR (500 MHz, $CD_3OD$) δ 7.90 (s, 1H), 7.54 (s, 1H), 7.49 (d, J=8.5 Hz, 1H), 7.46~7.44 (m, 1H), 7.36 (d, J=3.6 Hz, 1H), 7.25 (d, J=4.7 Hz, 1H), 7.05 (dd, J=8.5, 1.5 Hz, 1H), 6.93 (d, J=3.6 Hz, 1H), 5.28 (s, 2H); $^{13}$C NMR (125 MHz, $CD_3OD$) δ 165.3, 163.5, 148.7, 140.4, 138.8, 135.6, 128.5, 127.7, 125.2, 118.6, 111.4, 110.9, 102.4, 94.4, 67.8; MS (FAB) m/z (rel intensity) 315 (22), 314 ([M$^+$], 100), 313 (14), 232 (44), 218 (18), 99 (11), 97 (70), 81 (319, 57 (12); HRMS (FAB) calcd. for $C_{15}H_{11}N_3OS_2$ [M$^+$] 313.3969, found 314.0421.

*N-(4-Methyl-3-(thiazol-2-ylmethoxy)phenyl)thiazol-2-amine JLJ000064 (jrII-210a)

Following the general procedure for O-alkylation, Method B, a mixture of 2-methyl-5-(thiazol-2-ylamino)phenol (158 mg, 0.48 mmol) and $Cs_2CO_3$ (158 mg, 0.48 mmol) in acetone (4.4 mL) was treated with 2-bromomethylthiazole (86 mg, 0.48 mmol) at RT. Reaction control by TLC showed full conversion after 2.5 h. The title compound was obtained after purification by flash chromatography on silica gel (hexane:EtOAc 4/6) in 51% yield (75 mg).

$^1$H NMR (500 MHz, $CDCl_3$) Γ 7.82 (d, J=3.2 Hz, 1H), 7.42 (br s, 1H), 7.38 (d, J=3.2 Hz, 1H), 7.27 (m, 1H), 7.14 (d, J=8.0 Hz, 1H), 7.04 (d, J=2.1 Hz, 1H), 6.86 (dd, J=8.0, 2.1 Hz, 1H), 6.62 (d, J=3.6 Hz, 1H), 5.41 (s, 2H), 2.28 (s, 3H); $^{13}$C NMR (125 MHz, $CDCl_3$) δ 167.4, 166.6, 156.6, 142.6, 139.9, 138.4, 131.4, 121.7, 119.7, 111.2, 107.0, 102.7, 67.6, 15.8; MS (FAB) m/z (rel intensity) 305 (20), 364 ([M$^+$], 100), 303 (37), 207 (14), 206 (15), 205 (28), 98 (12); HRMS (FAB) calcd. for $C_{14}H_{13}N_3OS_2$ [M$^+$] 303.4017, found 304.0571.

*N-(4-Chloro-3-(thiazol-2-ylmethoxy)phenyl)thiazol-2-amine JLJ000065 (jrII-211a)

Following the general procedure for O-alkylation, Method B, a mixture of 2-chloro-5-(thiazol-2-ylamino)phenol (100 mg, 0.44 mmol) and $Cs_2CO_3$ (147 mg, 0.44 mmol) in acetone (4.4 mL) was treated with 2-bromomethylthiazole (88 mg, 0.44 mmol) at RT. Reaction control by TLC showed full conversion after 3 h. The title compound was obtained after purification by flash chromatography on silica gel (hexane:EtOAc 1/1) in 33% yield (47 mg).

$^1$H NMR (500 MHz, CDCl$_3$) δ 9.30 (br s, 1H), 7.81 (d, J=2.1 Hz, 1H), 7.40 (d, J=2.1 Hz, 1H), 7.33 (d, J=8.5 Hz, 1H), 7.30 (d, J=3.1 Hz, 1H), 6.94 (d, J=8.1 Hz, 1H), 6.65 (d, J=3.1 Hz, 1H), 5.45 (s, 2H); $^{13}$C NMR (125 MHz, CDCl$_3$) δ 166.3, 165.3, 154.0, 142.6, 140.6, 138.5, 130.9, 120.2, 116.5, 111.7, 107.9, 104.3, 68.4; MS (FAB) m/z (rel intensity) 324 (100), 323 ([M$^+$], 22), 288 (59), 227 (19), 226 (13), 181 (34), 98 (43); HRMS (FAB) calcd. for C$_{13}$H$_{10}$ClN$_3$OS$_2$ [M$^+$] 323.8200, found 324.0027.

*N-(4-Cyano-3-(thiazol-2-ylmethoxy)phenyl)thiazol-2-amine JLJ000066 (jrII-212b)

Following the general procedure for O-alkylation, Method B, a mixture of 2-hydroxy-4-(thiazol-2-ylamino)benzonitrile (70 mg, 0.32 mmol) and Cs$_2$CO$_3$ (105 mg, 0.32 mmol) in acetone (4.4 mL) was treated with 2-bromomethylthiazole (57 mg, 0.32 mmol) at RT. Reaction control by TLC showed full conversion after 4 h. The title compound was obtained after purification by flash chromatography on silica gel (hexane:EtOAc 4/6) in 8 yield (8 mg).

$^1$H NMR (500 MHz, CDCl$_3$) δ 8.33~8.21 (br s, 1H), 7.82 (d, J=3.2 Hz, 1H), 7.51 (d, J=8.5 Hz, 1H), 7.45 (d, J=1.6 Hz, 1H), 7.42 (d, J=3.2 Hz, 1H), 7.38 (d, J=3.6 Hz, 1H), 6.99 (dd, J=8.5, 1.7 Hz, 1H), 6.81 (d, J=3.6 Hz, 1H), 5.45 (s, 2H); $^{13}$C NMR (125 MHz, CDCl$_3$) δ 165.4, 162.6, 160.8, 145.8, 142.6, 139.2, 134.8, 120.6, 116.5, 110.1, 109.8, 100.9, 94.8, 68.1; MS (FAB) m/z (rel intensity) 316 (20), 315 ([M$^+$], 100), 314 (20), 218 (31), 199 (94), 98 (72), 63 (11); HRMS (FAB) calcd. for C$_{14}$H$_{10}$N$_4$OS$_2$ [M$^+$] 314.3840, found 315.0377.

*N-(3-(benzyloxy)-4-methylphenyl)thiazol-2-amine JLJ000045 (jr-213a)

Following the general procedure for O-alkylation, Method A, a mixture of 2-methyl-5-(thiazol-2-ylamino)phenol (70 mg, 0.34 mmol) and K$_2$CO$_3$ (52 mg, 0.32 mmol) in acetone (4.4 mL) was treated with benzyl bromide (58 mg, 0.34 mmol) at RT. Reaction control by TLC showed full conversion after 2 h 30 min. Subsequent benzyl bromide (20 microliter) and K$_2$CO$_3$ (20 mg) were added and stirred over night The title compound was obtained after purification by flash chromatography on silica gel (hexane:EtOAc 3/1) in 58% yield (58 mg).

$^1$H NMR (500 MHz, CDCl$_3$) δ 9.15-9.08 (br s, 1H), 7.46 (d, J=7.2 Hz, 2H), 7.40 (t, J=7.2 Hz, 2H), 7.34 (t, J=7.2 Hz, 1H), 7.22 (d, J=3.7 Hz, 1H), 7.14 (d, J=7.9 Hz, 1H), 6.95 (d, J=2.1 Hz, 1H), 6.85 (dd, J=7.9, 2.1 Hz, 1H), 6.56 (d, J=3.6 Hz, 1H), 5.11 (s, 2H), 2.27 (s, 3H); $^{13}$C NMR (125 MHz, CDCl$_3$) δ 166.9, 157.5, 139.7, 138.4, 137.1, 131.2, 128.6, 127.8, 127.0, 122.0, 110.7, 106.8, 103.0, 69.9, 15.9; MS (FAB) m/z (rel intensity) 298 (24), 297 ([M$^+$], 100), 296 (37), 91 (31); HRMS (FAB) calcd. for C$_{17}$H$_{16}$N$_2$OS [M$^+$]296.3884, found 297.1068.

*N-(3-(benzyloxy)-4-chlorophenyl)thiazol-2-amine JLJ000071 (jrIII-15a)

Following the general procedure for O-alkylation, Method B, a mixture of 2-chloro-5-(thiazol-2-ylamino)phenol (50 mg, 0.22 mmol) and Cs$_2$CO$_3$ (72 mg, 0.22 mmol) in acetone (4.4 mL) was treated with benzyl bromide (38 mg, 0.22 mmol) at RT. Reaction control by TLC showed full conversion after 2 h. The title compound was obtained after purification by flash chromatography on silica gel (hexane:EtOAc 7/3) in 53% yield (37 mg).

$^1$H NMR (500 MHz, CDCl$_3$) δ 9.00 (br s, 1H), 7.47 (d, J=7.4 Hz, 2H), 7.39 (t, J=7.4 Hz, 2H), 7.33 (s, 1H), 7.32 (d, J=8.5 Hz, 1H), 7.22 (d, J=3.5 Hz, 1H), 7.10 (d, J=2.2 Hz, 1H), 6.85 (dd, J=8.5, 2.3 Hz, 1H), 6.62 (d, J=3.6 Hz, 1H), 5.18 (s, 2H); $^{13}$C NMR (125 MHz, CDCl$_3$) δ 165.6, 154.8, 140.4, 138.5, 136.3, 430.7, 128.7, 128.1, 127.1, 116.8, 111.1, 107.7, 104.4, 70.9.

*N-(3-(2-methylbenzyloxy)-4-chlorophenyl)thiazol-2-amine JLJ000083 (jrIII-48a)

Following the general procedure for O-alkylation, Method B, a mixture of 2-chloro-5-(thiazol-2-ylamino)phenol (50 mg, 0.22 mmol) and Cs$_2$CO$_3$ (72 mg, 0.22 mmol) in acetone (4.4 mL) was treated with 2-methylbenzyl bromide (41 mg, 0.22 mmol) at RT. Reaction control by TLC showed full conversion after 3 h. The title compound was obtained after purification by flash chromatography on silica gel (hexane:EtOAc 4/1) in 58% yield (42 mg).

$^1$H NMR (500 MHz, CDCl$_3$) δ 8.49-8.34 (br s, 1H), 7.47 (m, 1H), 7.32 (d, J=8.5 Hz, 1H), 7.30-7.21 (m, 4H), 7.17 (br s, 1H), 6.86 (dd, J=8.5, 2.5 Hz, 1H), 6.64 (d, J=3.4 Hz, 1H), 5.14 (s, 2H), 2.41 (s, 31-1); $^{13}$C NMR (125 MHz, CDCl$_3$) δ 165.2, 154.9, 140.3, 138.7, 136.5, 134.1, 130.7, 130.4, 128.3, 128.3, 126.1, 116.8, 110.9, 108.0, 104.3, 69.6, 19.0.

*(E/Z)-N-(4-methyl-3-(3-methylpent-2-enyloxy)phenyl)thiazol-2-amine JLJ000050 (jrII-147c)

Following the general procedure for O-alkylation, Method B, a mixture of 2-methyl-5-(thiazol-2-ylamino)phenol (150 mg, 0.73 mmol) and Cs$_2$CO$_3$ (237 mg, 0.73 mmol) in acetone (4.4 mL) was treated with (E/Z)-1-bromo-3-methylpent-2-ene (130 mg, 0.80 mmol) at 0° C. The reaction mixture was heated to RT and stirred for 2 h. The title compound was obtained after purification by flash chromatography on silica gel (hexane:EtOAc 1/1) in 61% yield (128 mg).

$^1$H NMR (500 MHz, CDCl$_3$) δ 9.59 (br s, 1H), 7.30 (d, J=3.4 Hz, 1H), 7.11 (d, J=8.0 Hz, 1H), 6.90 (s, 1H), 6.84 (dd, J=8.0, 1.9 Hz, 1H), 6.58 (d, J=3.4 Hz, 1H), 5.51 (m, 1H), 4.58 (d, J=6.0 Hz, OCH$_2$CH=E isomer, 72%), 4.54 (d, J=6.7 Hz, OCH$_2$CH=Z isomer, 28%), 2.21 (s, 3H), 2.15 (q, J=7.6 Hz, CH$_2$CH$_3$ Z isomer), 2.10 (q, J=7.3 Hz, CH$_2$CH$_3$ E isomer), 1.80 (s, CH$_3$ Z isomer), 1.74 (s, CH$_3$ E isomer), 1.06 (t, J=7.3 Hz, CH$_2$CH$_3$ E isomer), 1.04 (t, J=7.6 Hz, CH$_2$CH$_3$ Z isomer); $^{13}$C NMR (125 MHz, CDCl$_3$) δ 167.2, 157.7, 143.3 (Z isomer), 142.4 (E isomer), 139.7, 138.3, 131.0, 122.0, 119.5 (Z isomer), 118.5 (E isomer), 110.3, 106.6, 103.0, 65.3 (E isomer), 64.7 (Z isomer), 32.2, 25.4 (E isomer), 23.0 (Z isomer), 16.7 (Z isomer), 15.8 (E isomer), 12.9 (Z isomer), 12.3 (E isomer); MS (FAB) m/z (rel intensity) 290 (19), 289 ([M$^+$], 85), 288 (41), 235 (18), 208 (16), 207 (100), 206 (47), 83 (14), 55 (11); HRMS (FAB) calcd. for C$_{16}$H$_{20}$N$_2$OS [M$^+$] 288.4090, found 289.1373.

*(E/Z)-N-(4-chloro-3-(3-methylpent-2-enyloxy)phenyl)thiazol-2-amine JLJ000052 (jrII-153a)

Following the general procedure for O-alkylation, Method B, a mixture of 2-chloro-5-(thiazol-2-ylamino)phenol (117 mg, 0.52 mmol) and Cs$_2$CO$_3$ (168 mg, 0.52 mmol) in acetone (4.4 mL) was treated with (E/Z)-1-bromo-3-methylpent-2-ene (92 mg, 0.56 mmol) at 0° C. The reaction mixture was heated to RT and stirred for 4 h. The title compound was obtained after purification by flash chromatography on silica gel (hexane:EtOAc 1/1) in 75% yield (119 mg).

$^1$H NMR (400 MHz, CDCl$_3$) δ 9.83 (br s, 1H), 7.31 (d, J=3.7 Hz, 1H), 7.31 (d, J=8.3 Hz, 1H), 7.05 (d, J=2.3 Hz, 1H), 6.85 (dd, J=8.3, 2.3 Hz, 1H), 6.65 (d, J=3.7 Hz, 1H), 5.51 (m, 1H), 4.65 (d, J=6.3 Hz, OCH$_2$CH=E isomer, 75%), 4.61 (d, J=6.5 Hz, OCH$_2$CH=Z isomer, 25%), 2.14 (q, J=7.6 Hz, CH$_2$CH$_3$ Z isomer), 2.09 (q, J=7.4 Hz, CH$_2$CH$_3$ E isomer), 1.79 (s, CH$_3$ Z isomer), 1.74 (s, CH$_3$ E isomer), 1.04 (t, J=7.4 Hz, CH$_2$CH$_3$ E isomer), 1.03 (t, J=7.6 Hz, CH$_2$CH$_3$ Z isomer); $^{13}$C NMR (100 MHz, CDCl$_3$) δ 166.1, 155.0, 144.4 (Z isomer), 143.4 (E isomer), 140.5, 138.2, 130.6, 118.6 (Z isomer), 117.6 (E isomer), 116.6, 110.8, 107.4, 104.2, 66.3 (E isomer), 65.6 (Z isomer), 32.2 (E isomer), 25.4 (Z isomer), 23.0 (Z isomer), 16.8 (E isomer), 12.9 (Z isomer), 12.3 (E isomer); MS (FAB) m/z (rel intensity) 311 (17), 310 (16), 309 ([M$^+$], 42), 308 (20), 229 (39), 228 (28), 227 (100), 226 (43), 83 (59), 55 (17); HRMS (FAB) calcd. for C$_{15}$H$_{17}$ClN$_2$OS [M$^+$] 308.8273, found 309.0822.

*(E/Z)-N-(4-ethyl-3-(3-methylpent-2-enyloxy)phenyl)thiazol-2-amine JLJ000051 (jrII-151a)

Following the general procedure for O-alkylation, Method B, a mixture of 2-ethyl-5-(thiazol-2-ylamino)phenol (76 mg, 0.35 mmol) and Cs$_2$CO$_3$ (115 mg, 0.35 mmol) in acetone was treated with (E/Z)-1-bromo-3-methylpent-2-ene (79 mg, 0.39 mmol) at 0° C. The reaction mixture was heated to RT and stirred for 3 h. The title compound was obtained after purification by flash chromatography on silica gel (hexane:EtOAc 4/1) in 55% yield (58 mg).

$^1$H NMR (500 MHz, CDCl$_3$) δ 8.98 (br s, 1H), 7.29 (d, J=2.2 Hz, 1H), 7.12 (d, J=7.9 Hz, 1H), 6.85 (d, J=7.8 Hz, 1H), 6.58 (d, J=2.2 Hz, 1H), 5.49 (m, 1H), 4.57 (d, J=6.0 Hz, OCH$_2$CH=E isomer, 73%), 4.54 (d, J=6.4 Hz, OCH$_2$CH=Z isomer, 27%), 2.63 (q, J=7.3 Hz, 2H), 2.14 (q, J=7.5 Hz, CH$_2$CH$_3$ Z isomer), 2.09 (q, J=7.3 Hz, CH$_2$CH$_3$ E isomer), 1.80 (s, CH$_3$ Z isomer), 1.73 (s, CH$_3$ E isomer), 1.19 (t, J=7.3 Hz, 3H), 1.05 (t, J=7.5 Hz, 3H); $^{13}$C NMR (125 MHz, CDCl$_3$) δ 166.8, 157.4, 143.2 (Z isomer), 142.4 (E isomer), 139.5, 138.5, 129.4, 128.1, 119.6 (Z isomer), 118.6 (E isomer), 110.4, 106.9, 103.1, 65.3 (E isomer), 64.7 (Z isomer), 32.3 (E isomer), 25.4 (Z isomer), 23.0 (Z isomer), 22.8, 16.6 (E isomer), 14.2, 12.9 (Z isomer), 12.4 (E isomer); MS (FAB) m/z (rel intensity) 304 (22), 303 ([M$^+$], 87), 302 (41), 222 (20), 221 (100), 220 (49), 83 (27), 55 (19); HRMS (FAB) calcd. for C$_{17}$H$_{22}$N$_2$OS [M$^+$] 302.4358, found 303.1523.

*N-(4-Chloro-3-(4-methylpent-3-en-2-yloxy)phenyl)thiazol-2-amine JLJ000082 35a1)

Following the procedure general for O-alkylation, Method C, 2-chloro-5-(thiazol-2-ylamino)phenol (50 mg, 0.22 mmol), 4-Methylpent-3-en-2-ol (23 mg, 0.23 mmol), Ph$_3$P (58 mg, 0.22 mmol) were suspended in THF (0.07 mL). The reaction flask was lowered into a sonication bath and sonicated for several minutes giving a clear and highly viscous solution. While sonication, DEAD (0.043 mL, 0.22 mmol) was added slowly. The reaction mixture was stirred for 1 h. The title compound was obtained after purification by flash chromatography on silica gel (hexane:EtOAc 4/1) in 24% yield (16 mg).

$^1$H NMR (500 MHz, CDCl$_3$) δ 8.20-7.90 (br s, 1H), 7.27 (d, J=8.4 Hz, 1H), 7.27 (d, J=4.4 Hz, 1H), 7.06 (d, J=2.5 Hz, 1H), 6.78 (dd, J=8.5, 2.6 Hz, 1H), 6.65 (d, J=4.2 Hz, 1H), 5.28 (dt, J=8.2, 1.3 Hz, 1H), 5.01 (dd, J=8.2, 6.3 Hz, 1H), 1.72 (s, 3H), 1.68 (s, 3H), 1.46 (d, J=6.3 Hz, 3H).

*N-(4-Chloro-3-(cyclopentenyloxy)phenyl)thiazol-2-amine JLJ000067 (jrII-232a)

Following the general procedure for O-allylation, Method B, a mixture 2-chloro-5-(thiazol-2-ylamino)phenol (88 mg, 0.39 mmol) and Cs$_2$CO$_3$ (127 mg, 0.39 mmol) in acetone was treated with 1-(chloromethyl)cyclopentene (60 mg, 0.39 mmol) at 0° C. The reaction mixture was heated to 60° C. and stirred for 3 h. The title compound was obtained after purification by flash chromatography on silica gel (hexane:EtOAc 8/2) in 25% yield (29 mg).

$^1$H NMR (500 MHz, CDCl$_3$) δ 9.20~8.00 (br s, 1H), 7.31 (d, J=3.8 Hz, 1H), 7.30 (d, J=8.5 Hz, 1H), 7.09 (d, J=2.5 Hz, 1H), 6.83 (dd, J=8.5, 2.5 Hz, 1H), 6.66 (d, J=3.8 Hz, 1H), 5.80 (br s, 1H), 4.67 (s, 2H), 2.43~2.38 (m, 4H), 1.95 (q, J=7.5 Hz, 2H); $^{13}$C NMR (125 MHz, CDCl$_3$) δ 165.5, 155.0, 140.2, 139.2, 138.6, 130.6, 128.6, 116.6, 110.8, 107.8, 104.0, 68.3, 32.8, 32.5, 23.2.

*N-(4-Cyano-3-(cyclopentenyloxy)phenyl)thiazol-2-amine JLJ000068 (jrII-258/jrII-260a)

Following the procedure general for O-alkylation, Method C$_{1-2}$-cyano-5-(thiazol-2-ylamino)phenol (70 mg, 0.32 mmol), 1-cyclopentene-1-methanol (33 mg, 0.34 mmol), Ph$_3$P (88 mg, 0.34 mmol) were suspended in THF (0.11 mL). The reaction flask was lowered into a sonication bath and sonicated for several minutes giving a clear and highly viscous solution. While sonication, DEAD (0.066 mL, 0.34 mmol) was added slowly. The reaction mixture was stirred for 1 h. The title compound was obtained after purification by flash chromatography on silica gel (hexane:EtOAc 7/3) in 34% yield (32 mg).

$^1$H NMR (500 MHz, CDCl$_3$) δ 8.13 (br s, 1H), 7.48 (d, J=8.4 Hz, 1H), 7.37 (d, J=3.6 Hz, 1H), 7.32 (d, J=2.0 Hz, 1H), 6.83 (dd, J=8.4, 2.0 Hz, 1H), 6.81 (d, J=3.6 Hz, 1H), 5.83 (s, 1H), 4.73 (s, 2H), 2.45~2.33 (m, 4H), 1.95 (quint., J=7.2 Hz, 2H); $^{13}$C NMR (125 MHz, CDCl$_3$) δ 162.8, 162.1, 145.5, 139.0, 138.6, 134.5, 129.1, 116.9, 109.8, 109.0, 100.5, 94.7, 68.2, 32.8, 32.5, 23.2.

*N-(4-Chloro-3-((2-methylcyclopent-1-enyl)methoxy)phenyl)thiazol-2-amine JLJ000081 (jrIII-49a)

To a solution of (2-methylcyclopent-1-yl)methanol (29 mg, 0.26 mmol) in pentane (0.7 mL) at 0° C. was added 45% HBr in AcOH (0.07 mL, 0.52 mmol). After having been stirred for 30 min, the reaction mixture was washed with brine, saturated aqueous NaHCO$_3$, dried over MgSO$_4$ and filtered with Et$_2$O. This solution was added to a solution of 2-chloro-5-(thiazol-2-ylamino)phenol (59 mg, 0.26 mmol) and Cs$_2$CO$_3$ (85 mg, 0.26 mmol) in acetone (1 mL). After 4 h, the reaction mixture was diluted with AcOEt and washed with 5% aqueous NaOH solution and brine. The organic phase was dried over Na$_2$SO$_4$, concentrated and the crude product was purified by flash chromatography on silica gel (hexane:EtOAc 8/2) to give the product (3 mg, 3% yield).

$^1$H NMR (500 MHz, CDCl$_3$) δ 8.00-7.80 (br s, 1H), 7.29 (d, J=3.6 Hz, 2H), 7.29 (d, J=8.5 Hz, 1H), 7.13 (d, J=2.5 Hz, 1H), 6.81 (dd, J=8.5, 2.5 Hz, 1H), 6.66 (d, J=3.7 Hz, 1H), 4.66 (s, 2H), 2.52-2.49 (m, 2H), 2.38-2.35 (m, 2H), 1.84 (quint., J=7.4 Hz, 3H), 1.74 (s, 3H); $^{13}$C NMR (125 MHz, CDCl$_3$) δ 155.2, 140.1, 138.9, 137.8, 130.5, 130.2, 116.9, 110.8, 108.1, 104.3, 66.3, 39.0, 34.4, 21.5, 14.2.

*N-(4-Chloro-3-(cyclohexylmethoxy)phenyl)thiazol-2-amine JLJ000069 (jrII-241a)

Following the procedure general for O-alkylation, Method C, 2-chloro-5-(thiazol-2-ylamino)phenol (70 mg, 0.31 mmol), 1-cyclohexanol (34 μM, 0.32 mmol), Ph$_3$P (84 mg, 0.32 mmol) were suspended in THF (0.1 mL). The reaction flask was lowered into a sonication bath and sonicated for several minutes giving a clear and highly viscous solution. While sonication, DEAD (0.063 mL, 0.32 mmol) was added slowly. The reaction mixture was stirred for 1 h. The title compound was obtained after purification by flash chromatography on silica gel (hexane:EtOAc 7/3) in 5% yield (5 mg).
$^1$H NMR (500 MHz, CDCl$_3$) δ 8.12 (br s, 1H), 7.30 (d, J=3.5 Hz, 1H), 7.29 (d, J=8.4 Hz, 1H), 7.10 (d, J=2.5 Hz, 1H), 6.82 (dd, J=8.4, 2.5 Hz, 1H), 6.66 (d, J=3.7 Hz, 1H), 4.30 (sept., J=3.8 Hz, 1H), 2.00~1.97 (m, 2H), 1.86~1.79 (m, 2H), 1.70~1.25 (m, 6H); $^{13}$C NMR (125 MHz, CDCl$_3$) δ 165.3, 154.1, 140.1, 138.8, 130.7, 118.0, 111.1, 108.0, 106.1, 77.2, 31.6, 25.6, 23.5.

*N-(4-Chloro-3-(hexylmethoxy)phenyl)thiazol-2-amine JLJ000079 (jrII-234a)

Following the procedure general for O-alkylation, Method C, 2-chloro-5-(thiazol-2-ylamino)phenol (50 mg, 0.22 mmol), 1-hexanol (0.024 ml, 0.23 mmol), Ph$_3$P (60 mg, 0.23 mmol) were suspended in THF (0.07 mL). The reaction flask was lowered into a sonication bath and sonicated for several minutes giving a clear and highly viscous solution. While sonication, DEAD (0.045 mL, 0.23 mmol) was added slowly. The reaction mixture was stirred for 1 h. The title compound was obtained after purification by flash chromatography on silica gel (hexane:EtOAc 7/3) in 38% yield (23 mg).
$^1$H NMR (500 MHz, CDCl$_3$) δ 8.50~8.00 (br s, 1H), 7.30 (d, J=3.4 Hz, 1H), 7.30 (d, J=8.6 Hz, 1H), 7.06 (d, J=2.2 Hz, 1H), 6.83 (dd, J=8.6, 2.2 Hz, 1H), 6.66 (d, J=3.4 Hz, 1H), 4.03 (t, J=6.7 Hz, 2H), 1.85 (quint., J=6.7 Hz, 2H), 1.53~1.48 (m, 2H), 1.40~1.20 (m, 6H), 0.91 (t, J=7.0 Hz, 3H); $^{13}$C NMR (125 MHz, CDCl$_3$) δ 165.7, 155.3, 140.3, 138.4, 130.5, 116.6, 110.6, 107.7, 103.8, 69.2, 31.5, 29.0, 25.7, 22.6, 14.0.

*1-(3-Hydroxy-4-methylphenyl)urea (jr-217a)

5-Amino-o-cresol (1 g, 8.12 mmol) was dissolved in glacial acetic acid (4.1 mL) and H$_2$O (8.41E) ata 35° C. The potassium cyanate solution was added slowly with stirring until a with precipitate of the product appears. The rest is added quickly with vigorous agitation. After 24 h, the reaction mixture was diluted with H$_2$O, cooled to 0° C. and filtered with suction, washed with H$_2$O and dried under high vacuum to afford the product (1.3 g, 99% yield).
$^1$H NMR (500 MHz, DMSO) δ 9.15 (s, 1H), 8.29 (s, 3H), 7.04 (d, J=1.8 Hz, 1H), 6.84 (d, J=8.1 Hz, 1H), 6.59 (dd, J=8.1, 1.8 Hz, 1H), 2.00 (s, 3H); $^{13}$C NMR (125 MHz, DMSO) δ 156.4, 155.6, 139.4, 130.6, 116.9, 108.9, 105.2, 15.8.

*Ethyl 2-(3-hydroxy-4-methylphenylamino)oxazole-4-carboxylate (jr-226b)

A solution containing 1-(3-hydroxy-4-methylphenyl)urea (150 mg, 0.9 mmol) and ethyl 3-bromopyruvate (0.11 mL, 0.9 mmol) in dry DMF (3.611E) was heated at 60° C. for 6 h. The reaction mixture was diluted with EtOAc and washed with brine and saturated NaHCO$_3$ solution and the combined organic layers were dried (Na$_2$SO$_4$) and concentrated. The crude product was purified by flash chromatography on silica gel (hexane:EtOAc 6/4) to give the product in 50% yield (119 mg).
$^1$H NMR (500 MHz, CD$_3$OD) δ 8.00 (s, 1H), 7.18 (d, J=2.1 Hz, 1H), 6.97 (d, J=8.1 Hz, 1H), 6.82 (dd, J=8.1, 2.1 Hz, 1H), 4.31 (q, j=7.1 Hz, 2H), 2.14 (s, 3H), 1.34 (t, J=7.1 Hz, 3H); $^{13}$C NMR (125 MHz, CD$_3$OD) δ 163.8, 159.8, 157.2, 139.6, 139.2, 134.1, 132.3, 120.1, 110.3, 105.9, 62.4, 16.1, 15.0; MS (FAB) m/z (rel intensity); HRMS (FAB) calcd. for CHNOS [M$^+$], found.

Ethyl 2-(4-methyl-3-(3-methylbut-2-enyloxy)phenylamino)oxazole-4-carboxylate (jr-229a)

Following the general procedure for O-alkylation, Method A, a mixture of ethyl 2-(3-hydroxy-4-methylphenylamino) oxazole-4-carboxylate (118 mg, 0.45 mmol) and K$_2$CO$_3$ (68 mg, 0.50 mmol) in acetone (4.5 mL) was treated with 4-bromo-2-methyl-2-butene (0.063 mL, 0.54 mmol) at 60° C. Reaction control by TLC showed full conversion after 4 h. The title compound was obtained after purification by flash chromatography on silica gel (hexane:EtOAc 7/3) in 30% yield (45 mg).
$^1$H NMR (500 MHz, CDCl$_3$) δ 8.02 (br s, 1H), 7.84 (s, 1H), 7.05 (d, J=8.2 Hz, 1H), 7.01 (d, J=2.1 Hz, 1H), 6.89 (dd, J=8.2, 2.1 Hz, 1H), 5.49 (tm, J=6.6 Hz, 1H), 4.53 (d, J=6.6 Hz, 2H), 4.31 (q, J=7.1 Hz, 2H), 2.17 (s, 3H), 1.79 (s, 3H), 1.74 (s, 3H), 1.31 (t, J=7.1 Hz, 3H); $^{13}$C NMR (125 MHz, CDCl$_3$) δ 161.6, 157.9, 157.5, 137.5, 137.4, 136.7, 132.9, 130.7; 121.9, 120.1, 110.2, 102.9, 65.2, 61.0, 25.8, 18.3, 15.8, 14.2.

*(2-(4-Methyl-3-(3-methylbut-2-enyloxy)phenylamino)oxazol-4-yl)methanol JLJ000046 (jr-233a)

A solution of the compound ethyl 2-(4-methyl-3-(3-methylbut-2-enyloxy)phenylamino)oxazole-4-carboxylate (42 mg, 0.13 mmol) in anhydro THF (1 mL) was added to a suspension of LiAlH$_4$ (10 mg, 0.25 mmol) in dry THF (1 mL) cooled at 0° C. under nitrogen atmosphere. After 2 h, the reaction mixture was quenched with H$_2$O, filtrated, dried over MgSO$_4$ and concentrated. The title compound was purified by flash chromatography on silica gel (hexane:EtOAc 1/1) to afford the product (13 mg, 34% yield).
$^1$H NMR (500 MHz, CD$_3$OD) δ 7.33 (s, 1H), 7.16 (d, J=2.1 Hz, 1H), 7.02 (d, J=8.1 Hz, 1H), 6.94 (dd, J=8.0, 2.1 Hz, 1H), 5.51 (tm, J=6.6 Hz, 1H), 4.57 (d, J=6.6 Hz, 2H), 4.46 (s, 2H), 2.14 (s, 3H), 1.81 (s, 3H), 1.78 (s, 3H); $^{13}$C NMR (125 MHz, CD$_3$OD) δ 159.8, 159.1, 141.7, 140.0, 138.7, 131.9, 130.0, 121.9, 121.7, 110.7, 103.4, 66.4, 58.0, 26.3, 18.7, 16.2; MS (FAB) m/z (rel intensity); HRMS (FAB) calcd. for CHNOS [M$^+$], found.

General Procedure for the synthesis of 2-R-5-(heteroaryl-2-ylamino)phenol

2-Bromopyridine or 2-chloropyrimidine (2 equiv.), 5-amino-2-substituted phenol (1 equiv) and 37% HCl solution (2 equiv) in 10% aqueous EtOH solution (0.2M) was stirred at 90° C. for 24 h. The reaction mixture was diluted with AcOEt and washed with 5% aqueous K$_2$CO$_3$ solution and brine. The organic phase was dried over Na$_2$SO$_4$, concentrated and the crude product was purified by flash chromatography on silica gel.

*2-Methyl-5-(pyridin-2-ylamino)phenol (jrII-248a)

Following the general procedure for the synthesis of 2-R-5-(heteroaryl-2-ylamino)phenol, 2-bromopyridine (0.6 mL, 6.33 mmol) and 5-amino-o-cresol (390 mg, 3.16 mmol) in 10% aqueous EtOH (10 mL) was heated at 90° C. for 18 h. The title compound was obtained after purification by flash chromatography on silica gel (hexane:EtOAc 6/4) in 43% yield (271 mg).

$^1$H NMR (500 MHz, CD$_3$OD) δ 8.03 (br d, J=4.0 Hz, 1H), 7.46 (ddd, J=8.5, 6.9, 1.9 Hz, 1H), 7.02 (d, J=2.0 Hz, 1H), 6.97 (d, J=8.0 Hz, 1H), 6.80 (d, J=8.5 Hz, 1H), 6.73 (dd, J=8.0, 2.0 Hz, 1H), 6.66 (dd, J=6.7, 5.4 Hz, 1H), 2.16 (s, 31-1); $^{13}$C NMR (125 MHz, CD$_3$OD) 158.5, 157.2, 148.7, 141.3, 139.5, 132.4, 120.3, 115.7, 113.3, 111.4, 108.7, 16.3.

*2-Chloro-5-(pyridin-2-ylamino)phenol (jrII-253a)

Following the general procedure for the synthesis of 2-R-5-(heteroaryl-2-ylamino)phenol, 2-bromopyridine (0.13 mL, 1.4 mmol) and 5-amino-2-chlorophenol (100 mg, 0.7 mmol) in 10% aqueous EtOH (2 mL) was heated at 90° C. for 18 h. The title compound was obtained after purification by flash chromatography on silica gel (hexane:EtOAc 7/3) in 24% yield (36 mg).

$^1$H NMR (500 MHz, CD$_3$OD) δ 8.11 (dd, J=5.1, 1.1 Hz, 1H), 7.55 (ddd, J=8.7, 7.1, 1.9 Hz, 1H), 7.37 (d, J=2.5 Hz, 1H), 7.15 (d, J=8.7 Hz, 1H), 6.88 (dd, J=8.7, 2.5 Hz, 1H), 6.82 (d, J=8.7 Hz, 1H), 6.75 (dd, J=7.1, 5.1 Hz, 1H); $^{13}$C NMR (125 MHz, CD$_3$OD) δ 157.8, 154.7, 148.6, 143.0, 139.3, 131.1, 116.2, 114.2, 113.0, 112.3, 108.6.

*2-Cyano-5-(pyridin-2-ylamino)phenol (jrIII-4a)

Following the general procedure for the synthesis of 2-R-5-(heteroaryl-2-ylamino)phenol, 2-bromopyridine (0.21 mL, 2.2 mmol) and 4-amino-2-hydroxybenzonitrile (146 mg, 1.1 mmol) in 10% aqueous EtOH (5 mL) was heated at 90° C. for 18 h. The title compound was obtained after purification by flash chromatography on silica gel (hexane:EtOAc 1/1) in 1% yield (1.5 mg).

$^1$H NMR (500 MHz, CD$_3$OD) δ 8.22 (br d, J=4.9 Hz, 1H), 7.72 (d, J=1.9 Hz, 1H), 7.63 (ddd, J=9.0, 7.1, 1.9 Hz, 1H), 7.35 (d, J=8.6 Hz, 1H), 6.94 (dd, J=8.6, 2.0 Hz, 1H), 6.90-6.86 (m, 2H).

*2-Methyl-5-(pyrimidin-2-ylamino)phenol (jrII-249a)

Following the general procedure for the synthesis of 2-R-5-(heteroaryl-2-ylamino)phenol, 2-chloropyrimidine (1 g, 8.7 mmol) and 4-amino-o-cresol (538 mg, 4.4 mmol) in 10% aqueous EtOH (10 mL) was heated at 90° C. for 18 h. The title compound was obtained after purification by flash chromatography on silica gel (hexane:EtOAc 1/1) in 8% yield (67 mg).

$^1$H NMR (500 MHz, CD$_3$OD) δ 8.37 (d, J=4.8 Hz, 2H), 7.29 (d, J=2.1 Hz, 1H), 6.98 (d, J=8.1 Hz, 1H), 6.89 (dd, J=8.1, 2.1 Hz, 1H), 6.74 (t, J=4.8 Hz, 1H), 2.16 (s, 3H); $^{13}$C NMR (125 MHz, CD$_3$OD) δ 162.2, 159.5, 156.9, 140.2, 131.9, 120.3, 113.3, 112.9, 108.5, 16.1.

*2-Chloro-5-(pyrimidin-2-ylamino)phenol (Procedure jrIII-53-jrIII-56; datas jrI-259)

2-Chloropyrimidine (1.5 g, 13.3 mmol), 5-amino-2-chlorophenol (318 mg, 2.2 mmol) and 37% HCl solution (1.1 mL, 13.3 mmol) in 10% aqueous EtOH solution (10 mL) was stirred at 90° C. for 24 h. Afterwards, 2-chloropyrimidine (1.5 g, 13.3) was added and after 24 h, the reaction mixture was diluted with AcOEt and washed with 5% aqueous K$_2$CO$_3$ solution and brine. The organic phase was dried over Na$_2$SO$_4$, concentrated and the crude product (179 mg, 36% yield) was used for the next step without additional purification.

$^1$H NMR (500 MHz, CD$_3$OD) δ 8.43 (d, J=4.9 Hz, 2H), 7.58 (d, J=2.4 Hz, 1H), 7.17 (d, J=8.7 Hz, 1H), 7.03 (dd, J=8.3, 2.5 Hz, 1H), 6.79 (t, J=4.8 Hz, 1H); $^{13}$C NMR (125 MHz, CD$_3$OD) δ 161.9, 159.5, 154.6, 141.7, 130.9, 115.0, 114.0, 113.3, 109.2.

*2-Cyano-5-(pyrimidin-2-ylamino)phenol (jrIII-5)

Following the general procedure for the synthesis of 2-R-5-(heteroaryl-2-ylamino)phenol, 2-chloropyrimidine (209 mg, 1.8 mmol) and 4-amino-2-hydroxybenzonitrile (123 mg, 0.9 mmol) in 10% aqueous EtOH (5 mL) was heated at 90° C. for 18 h. The title compound was obtained in 5% yield a (10 mg) and used for the next step without additional purification.

$^1$H NMR (500 MHz, CD$_3$OD) δ 8.51 (d, J=4.8 Hz, 2H), 7.86 (d, J=2.0 Hz, 1H), 7.39 (d, J=8.6 Hz, 1H), 7.10 (dd, J=8.6, 2.0 Hz, 1H), 6.91 (t, J=4.8 Hz, 1H); $^{13}$C NMR (125 MHz, CD$_3$OD) δ 162.9, 161.6, 159.6, 159.5, 134.7, 116.6, 115.1, 112.0, 106.3, 101.1.

*5-(4-Aminopyrimidin-2-ylamino)-2-methylphenol (jrIII-65)

Following the general procedure for the synthesis of 2-R-5-(heteroaryl-2-ylamino)phenol, 4-amino-2-chloropyrimidine (98 mg, 0.8 mmol) and 4-amino-o-cresol (93 mg, 0.8 mmol) in 10% aqueous EtOH (3 mL) was heated at 90° C. for 18 h. The title compound was obtained in 86% yield a (140 mg) and used for the next step without additional purification.

$^1$H NMR (500 MHz, CD$_3$OD) δ 7.78 (d, J=5.9 Hz, 1H), 7.17 (d, J=2.1 Hz, 1H), 6.96 (d, J=8.1 Hz, 1H), 6.85 (dd, J=8.1, 2.1 Hz, 1H), 5.95 (d, J=5.9 Hz, 2H), 2.15 (s, 3H); $^{13}$C NMR (125 MHz, CD$_3$OD) δ 166.3, 161.9, 156.8, 140.5, 132.0, 120.1, 113.3, 109.1, 108.9, 98.2, 16.1.

*5-(4-Aminopyrimidin-2-ylamino)-2-chlorophenol (jrIII-61)

Following the general procedure for the synthesis of 2-R-5-(heteroaryl-2-ylamino)phenol, 4-amino-2-chloropyrimidine (70 mg, 0.5 mmol) and 5-amino-2-chlorophenol (78 mg, 0.5 mmol) in 10% aqueous EtOH (2 mL) was heated at 90° C. for 18 h. The title compound was obtained in 47% yield a (60 mg) and used for the next step without additional purification.

$^1$H NMR (500 MHz, CD$_3$OD) δ 7.81 (d, J=5.9 Hz, 1H), 7.44 (d, J=2.5 Hz, 1H), 7.14 (d, J=8.7 Hz, 1H), 7.00 (dd, J=8.7, 2.5 Hz; 1H), 5.99 (d, J=5.9 Hz, 2H); $^{13}$C NMR (125 MHz, CD$_3$OD) δ 166.3, 161.6, 156.8, 154.5, 142.1, 130.8, 114.7, 113.5, 109.4, 98.6.

*5-(2-Aminopyrimidin-4-ylamino)-2-methylphenol (jrIII-67)

Following the general procedure for the synthesis of 2-R-5-(heteroaryl-2-ylamino)phenol, 2-amino-4-chloropyrimidine (70 mg, 0.5 mmol) and 5-amino-o-cresol (67 mg, 0.5 mmol) in 10% aqueous EtOH (2 mL) was heated at 90° C. for 18 h. The title compound was obtained in 94% yield a (110 mg) and used for the next step without additional purification.

$^1$H NMR (500 MHz, CD$_3$OD) δ 7.73 (d, J=6.0 Hz, 1H), 7.13 (s, 1H), 7.00 (d, J=8.1 Hz, 1H), 6.83 (dd, J=8.1, 1.9 Hz, 1H), 6.05 (d, J=6.0 Hz, 2H), 2.16 (s, 3H); $^{13}$C NMR (125

MHz, CD$_3$OD) δ 164.5, 163.8, 157.0, 156.3, 139.7, 132.1, 121.4, 114.2, 109.1, 104.5, 98.2, 16.2.

*5-(2-Aminopyrimidin-4-ylamino)-2-chlorophenol (jrIII-61)

Following the general procedure for the synthesis of 2-R-5-(heteroaryl-2-ylamino)phenol, 4-amino-2-chloropyrimidine (70 mg, 0.5 mmol) and 5-amino-2-chlorophenol (78 mg, 0.5 mmol) in 10% aqueous EtOH (2 mL) was heated at 90° C. for 18 h. The title compound was obtained in 47% yield a (60 mg) and used for the next step without additional purification.

$^1$H NMR (500 MHz, CD$_3$OD) g 7.78 (d, J=6.1 Hz, 1H), 7.45 (s, 1H), 7.19 (d, J=8.7 Hz, 1H), 7.04 (dd, J=8.7, 2.5 Hz, 1H), 6.07 (d, J=6.1 Hz, 1H); $^{13}$C NMR (125 MHz, CD$_3$OD) δ 164.5, 163.4, 156.5, 154.7, 141.4, 131.0, 114.2, 111.6, 110.3, 98.8.

*2-Chloro-5-(4-methylpyrimidin-2-ylamino)phenol (jrIII-80)

Following the general procedure for the synthesis of 2-R-5-(heteroaryl-2-ylamino)phenol, 2-chloro-4-methylpyrimidine (69 mg, 0.54 mmol) and 5-amino-2-chlorophenol (77 mg, 0.54 mmol) in 10% aqueous EtOH (3 mL) was heated at 90° C. for 18 h. The title compound was obtained in 74% yield a (94 mg) and used for the next step without additional purification.

$^1$H NMR (500 MHz, CD$_3$OD) δ 8.26 (d, J=5.1 Hz, 1H), 7.60 (d, J=2.5 Hz, 1H), 7.16 (d, J=8.7 Hz, 1H), 7.03 (dd, J=8.6, 2.5 Hz, 1H), 6.69 (d, J=5.1 Hz, 1H), 3.33 (s, 3H); $^{13}$C NMR (125 MHz, CD$_3$OD) δ 170.1, 161.7, 158.9, 154.6, 149.4, 141.9, 130.8, 113.4, 113.2, 109.0.

*5-(4-Methoxypyrimidin-2-ylamino)-2-methylphenol (Procedure jrIII-76; Datas jrIII-79b)

Following the general procedure for the synthesis of 2-R-5-(heteroaryl-2-ylamino)phenol, 2-chloro-4-methoxypyrimidine (44 mg, 0.30 mmol) and 4-amino-o-cresol (37 mg, 0.30 mmol) in 10% aqueous EtOH (2 mL) was heated at 90° C. for 18 h. The title compound was obtained in 21% yield a (14 mg) and used for the next step without additional purification.

$^1$H NMR (500 MHz, CD$_3$OD) δ 8.06 (d, J=5.8 Hz, 1H), 7.25 (d, J=2.0 Hz, 1H), 6.98 (d, J=8.2 Hz, 1H), 6.92 (dd, J=8.2, 2.0 Hz, 1H), 6.18 (d, J=5.8 Hz, 1H), 3.97 (s, 3H), 2.16 (s, 3H); $^{13}$C NMR (125 MHz, CD$_3$OD) δ 172.1, 162.1, 159.1, 156.8, 140.3, 131.9, 120.2, 112.9, 108.5, 99.8, 54.5, 16.1.

*2-Chloro-5-(4-methoxypyrimidin-2-ylamino)phenol (jrIII-75)

Following the general procedure for the synthesis of 2-R-5-(heteroaryl-2-ylamino)phenol, 2-chloro-4-methoxypyrimidine (87 mg, 0.60 mmol) and 5-amino-2-chlorophenol (86 mg, 0.60 mmol) in 10% aqueous EtOH (3 mL) was heated at 90° C. for 18 h. The title compound was obtained in 57% yield a (87 mg) and used for the next step without additional purification.

$^1$H NMR (500 MHz, CD$_3$OD) δ 8.10 (d, J=5.7 Hz, 1H), 7.51 (d, J=2.5 Hz, 1H), 7.17 (d, J=8.7 Hz, 1H), 7.05 (dd, J=8.7, 2.5 Hz, 1H), 6.22 (d, J=5.7 Hz, 1H), 3.97 (s, 3H); $^{13}$C NMR (125 MHz, CD$_3$OD) δ 172.1, 161.7, 159.2, 154.5, 141.8, 130.9, 115.0, 113.4, 109.3, 100.5, 54.6.

General procedure for O-alkylation of 2-R-5-(heteroaryl-2-ylamino)phenol

A mixture of 2-R-5-(heteroaryl-2-ylamino)phenol (1 equiv) and Cs$_2$CO$_3$ (1 equiv) in acetone (0.1M) was treated with 4-bromo-2-methyl-2-butene (1 equiv) at room temperature. After 2-4 h, the reaction mixture was diluted with AcOEt and washed with 5% aqueous NaOH solution and brine. The organic phase was dried over Na$_2$SO$_4$, concentrated and the crude product was purified by flash chromatography on silica gel.

N-(4-Methyl-3-(3-methylbut-2-enyloxy)phenyl)pyridin-2-amine JLJ000075 (jrIII-1a)

Following the general procedure for O-alkylation of 2-R-5-(heteroaryl-2-ylamino)phenol, 2-methyl-5-(pyridin-2-ylamino)phenol (67 mg, 0.33 mmol) and Cs$_2$CO$_3$ (113 mg, 0.35 mmol) in acetone (3.3 mL) was treated with 4-bromo-2-methyl-2-butene (0.038 mL, 0.33 mmol) at room temperature. The title compound was obtained after purification by flash chromatography on silica gel (hexane:EtOAc 8/2) in 48% yield (43 mg).

$^1$H NMR (500 MHz, CDCl$_3$) δ 8.18 (br d, J=3.9 Hz, 1H), 7.45 (ddd, J=8.8, 6.9, 1.8 Hz, 1H), 7.44 (d, J=1.8 Hz, 1H), 7.07 (d, J=7.9 Hz, 1H), 6.84 (d, J=8.4 Hz, 1H), 6.84 (d, J=1.9 Hz, 1H), 6.77 (dd, J=7.9, 1.9 Hz, 1H), 7.00-6.68 (m, 2H), 5.48 (tm, J=6.5 Hz, 1H), 4.51 (d, J=7.1 Hz, 2H), 2.19 (s, 3H), 1.79 (s, 3H), 1.72 (s, 3H); $^{13}$C NMR (125 MHz, CDCl$_3$) δ 157.6, 156.7, 148.5, 139.1, 137.6, 137.2, 130.9, 122.1, 120.2, 114.6, 113.0, 107.8, 105.6, 65.1, 25.8, 18.3, 15.8.

*N-(4-Chloro-3-(3-methylbut-2-enyloxy)phenyl)pyridin-2-amine JLJ000076 (jrIII-3a)

Following the general procedure for O-alkylation of 2-R-5-(heteroaryl-2-ylamino)phenol, 2-chloro-5-(pyridin-2-ylamino)phenol (34 mg, 0.15 mmol) and Cs$_2$CO$_3$ (51 mg, 0.16 mmol) in acetone (1.5 mL) was treated with 4-bromo-2-methyl-2-butene (0.017 mL, 0.15 mmol) at room temperature. The title compound was obtained after purification by flash chromatography on silica gel (hexane:EtOAc 8/2) in 74% yield (32 mg).

$^1$H NMR (500 MHz, CDCl$_3$) δ 8.21 (br d, J=3.9 Hz, 1H), 7.50 (ddd, J=8.9, 6.9, 1.9 Hz, 1H), 7.26 (d, J=8.5 Hz, 1H), 7.09 (d, J=2.4 Hz, 1H), 6.83 (d, J=8.5 Hz, 1H), 6.82 (d, J=8.5 Hz, 1H), 6.75 (dd, J=6.4, 5.1 Hz, 1H), 6.67 (br s, 1H), 5.51 (tm, J=6.6 Hz, 1H), 4.60 (d, J=6.5 Hz, 2H), 1.79 (s, 3H), 1.73 (s, 3H); $^{13}$C NMR (125 MHz, CDCl$_3$) δ 155.7, 154.8, 148.4, 140.2, 138.2, 137.7, 130.3, 119.5, 116.5, 115.4, 112.8, 108.7, 106.4, 66.1, 25.8, 18.3.

*N-(4-Cyano-3-(3-methylbut-2-enyloxy)phenyl)pyridin-2-amine JLJ000077 (jrIII-12a)

Following the general procedure for O-alkylation of 2-R-5-(heteroaryl-2-ylamino)phenol, 2-cyano-5-(pyridin-2-ylamino)phenol (2 mg, 0.01 mmol) and Cs$_2$CO$_3$ (3 mg, 0.01 mmol) in acetone (1.5 mL) was treated with 4-bromo-2-methyl-2-butene (1.1 µL, 0.01 mmol) at room temperature. The title compound was obtained after purification by flash chromatography on silica gel (hexane:EtOAc 7/3) in 38% yield (1 mg).

$^1$H NMR (500 MHz, CDCl$_3$) δ 8.29 (br d, J=3.4 Hz, 1H), 7.59 (t, J=7.1 Hz, 1H), 7.43 (d, J=8.4 Hz, 1H), 6.89-6.85 (m,

2H), 6.70 (br s, 1H), 5.50 (tm, J=6.6 Hz, 1H), 4.66 (d, J=6.4 Hz, 2H), 1.80 (s, 3H), 1.76 (s, 3H).

*N-(4-Methyl-3-(3-methylbut-2-enyloxy)phenyl)pyrimidin-2-amine JLJ000078

Following the general procedure for O-alkylation of 2-R-5-(heteroaryl-2-ylamino)phenol, 2-methyl-5-(pyrimidin-2-ylamino)phenol (65 mg, 0.32 mmol) and $Cs_2CO_3$ (111 mg, 0.34 mmol) in acetone (3.2 mL) was treated with 4-bromo-2-methyl-2-butene (37 μL, 0.34 mmol) at room temperature. The title compound was obtained after purification by flash chromatography on silica gel (hexane:EtOAc 7/3) in 57% yield (50 mg).
$^1$H NMR (500 MHz, $CDCl_3$) δ 8.39 (d, J=4.8 Hz, 2H), 7.30 (br s, 1H), 7.26 (s, 1H), 7.07 (d, J=8.0 Hz, 1H), 6.99 (dd, J=8.0, 2.0 Hz, 1H), 6.67 (t, J=4.8 Hz, 1H), 5.51 (tm, J=6.5 Hz, 1H), 4.55 (d, J=6.5 Hz, 2H), 2.19 (s, 3H), 1.79 (s, 3H), 1.75 (s, 3H); $^{13}$C NMR (125 MHz, $CDCl_3$) δ 160.5 158.0, 157.3, 138.0, 137.2, 130.5, 121.7, 120.4, 112.2 111.7, 104.4, 65.1, 25.8, 18.3; 15.8.

*N-(4-Chloro-3-(3-methylbut-2-enyloxy)phenyl)pyrimidin-2-amine JLJ000079 (jrIII-10a)

Following the general procedure for O-alkylation of 2-R-5-(heteroaryl-2-ylamino)phenol, 2-chloro-5-(pyrimidin-2-ylamino)phenol (30 mg, 0.14 mmol) and $Cs_2CO_3$ (47 mg, 0.14 mmol) in acetone (2.0 mL) was treated with 4-bromo-2-methyl-2-butene (16 μL, 0.14 mmol) at room temperature. The title compound was obtained after purification by flash chromatography on silica gel (hexane:EtOAc 7/3) in 53% yield (21 mg).
$^1$H NMR (500 MHz, $CDCl_3$) δ 8.43 (d, J=4.8 Hz, 2H), 7.51 (d, J=2.3 Hz, 1H), 7.27 (d, J=8.6 Hz, 1H), 7.10 (br s, 1H), 7.03 (dd, J=8.6, 2.3 Hz, 1H), 6.75 (t, J=4.8 Hz, 1H), 5.54 (tm, J=6.6 Hz, 1H), 4.64 (d, J=6.6 Hz, 2H), 1.80 (s, 3H), 1.77 (s, 3H); $^{13}$C NMR (125 MHz, $CDCl_3$) δ 160.0, 158.0, 154.6, 139.1, 138.2, 130.0, 119.5, 116.4, 112.9, 112.0, 105.6, 66.1, 25.9, 18.4.

*N-(4-Cyano-3-(3-methylbut-2-enyloxy)phenyl)pyrimidin-2-amine JLJ000080 (jrIII-13a)

Following the general procedure for O-alkylation of 2-R-5-(heteroaryl-2-ylamino)phenol, 2-cyano-5-(pyrimidin-2-ylamino)phenol (10 mg, 0.047 mmol) and $Cs_2CO_3$ (16 mg, 0.049 mmol) in acetone (2.0 mL) was treated with 4-bromo-2-methyl-2-butene (5.5 μL, 0.14 mmol) at room temperature. The title compound was obtained after purification by flash chromatography on silica gel (hexane:EtOAc 6/4) in 30% yield (4 mg).
$^1$H NMR (500 MHz, $CDCl_3$) δ 8.49 (d, J=4.8 Hz, 2H), 7.71 (d, J=1.9 Hz, 1H), 7.46 (d, J=8.5 Hz, 1H), 7.40 (br s, 1H), 7.05 (dd, J=8.5, 1.9 Hz, 1H), 6.85 (t, J=4.8 Hz, 1H), 5.51 (tm, J=6.6 Hz, 1H), 4.69 (d, J=6.6 Hz, 2H), 1.80 (s, 31-1), 1.79 (s, 3H); $^{13}$C NMR (125 MHz, $CDCl_3$) δ 161.8, 159.4, 158.0, 145.0, 138.6, 134.1, 119.0, 117.3, 113.9, 110.5, 102.3, 94.8, 65.9, 25.8, 18.4.

*N-(4-chloro-3-(4-methylpent-3-en-2-yloxy)phenyl)pyrimidin-2-amine JLJ000085 (jrIII59b1)

To a flask was added 2-chloro-5-(pyrimidin-2-ylamino)phenol (50 mg, 0.23 mmol), 4-methylpent-3-en-2-ol (23 mg, 0.23 mmol), $Ph_3P$ (59 mg, 0.23 mmol) and THF (0.08 mL). The reaction vessel was lowered into a sonication bath and sonicated for several minutes giving a clear and highly viscous solution. While sonication, DEAD (0.044 mL, 0.23 mmol) was added. After 1 h, the reaction mixture was concentrated in vacuo and the crude product was purified by flash chromatography on silica gel (hexane:EtOAc 7/3) to give the product in 17% yield (12 mg).
$^1$H NMR (400 MHz, $CDCl_3$) δ 8.41 (d, J=4.8 Hz, 2H), 7.45 (d, J=2.4 Hz, 1H), 7.25 (d, J=8.6 Hz, 1H), 7.12 (br s, 1H), 7.01 (dd, J=8.6, 2.4 Hz, 1H), 6.74 (t, J=4.8 Hz, 1H), 5.30-5.27 (m, 1H), 5.09-5.03 (m, 1H), 1.72 (s, 6H), 1.46 (d, J=6.3 Hz, 31-1); $^{13}$C NMR (125 MHz, $CDCl_3$) δ 159.9, 157.9, 154.0, 138.8, 134.6, 129.9, 126.6, 117.2, 112.8, 112.1, 107.6, 73.2, 25.7, 21.5, 18.3.

*N-(4-chloro-34(2-methylcyclopent-1-enyl)methoxy)phenyl)pyrimidin-2-amine JLJ000086 (jrIII60b1)

To a flask was added 2-chloro-5-(pyrimidin-2-ylamino)phenol (27 mg, 0.12 mmol), (2-methylcyclopent-1-yl)methanol (13 mg, 0.12 mmol), $Ph_3P$ (32 mg, 0.12 mmol) and THF (0.5 mL). The reaction vessel was lowered into a sonication bath and sonicated for several minutes giving a clear and highly viscous solution. While sonication, DEAD (0.024 mL, 0.12 mmol) was added. After 1 h, the reaction mixture was concentrated in vacuo and the crude product was purified by flash chromatography on silica gel (hexane:EtOAc 7/3) to give the product in 11% yield (4 mg).
$^1$H NMR (400 MHz, $CDCl_3$) δ 8.43 (d, J=4.8 Hz, 2H), 7.53 (d, J=2.4 Hz, 1H), 7.29 (d, J=8.6 Hz, 1H), 7.08 (br s, 1H), 7.01 (dd, J=8.6, 2.4 Hz, 1H), 6.75 (t, J=4.8 Hz, 1H), 4.69 (s, 2H), 2.57-2.48 (m, 2H), 2.41-2.32 (m, 2H), 1.83 (quint., J=7.4, 2H), 1.77 (s, 3H); $^{13}$C NMR (125 MHz, $CDCl_3$) δ 158.2, 158.0, 154.7, 139.0, 137.6, 129.9, 127.9, 119.6, 112.9, 111.9, 105.4, 66.1, 38.9, 34.4, 21.5, 14.2.

*$N^2$-(4-Methyl-3-(3-methylbut-2-enyloxy)phenyl)pyrimidin-2,4-diamine JLJ000089 (jrIII-69a)

Following the general procedure for O-alkylation of 2-R-5-(heteroaryl-2-ylamino)phenol, 5-(4-aminopyrimidin-2-ylamino)-2-methylphenol (52 mg, 0.24 mmol) and $Cs_2CO_3$ (78 mg, 0.24 mmol) in acetone (3.0 mL) was treated with 4-bromo-2-methyl-2-butene (28 μL, 0.24 mmol) at room temperature. The title compound was obtained after purification by flash chromatography on silica gel (hexane:EtOAc 6/4) in 28% yield (19 mg).
$^1$H NMR (500 MHz, $CD_3OD$) δ 7.79 (d, J=5.9 Hz, 1H), 7.20 (d, J=1.3 Hz, 1H), 7.03-6.99 (m, 2H), 5.97 (d, J=5.9 Hz, 1H), 5.51 (tm, J=6.4 Hz, 1H), 4.56 (d, J=6.4 Hz, 2H), 2.14 (s, 3H), 1.81 (s, 3H), 1.77 (s, 3H); $^{13}$C NMR (125 MHz, $CD_3OD$) δ 166.4, 161.9, 158.7, 156.7, 140.7, 138.5, 131.6, 122.1, 113.7, 106.3, 98.3, 66.4, 26.3, 18.7, 16.3.

*$N^2$-(4-Chloro-3-(3-methylbut-2-enyloxy)phenyl)pyrimidin-2,4-diamine JLJ000087 (jrIII-64a)

Following the general procedure for O-alkylation of 2-R-5-(heteroaryl-2-ylamino)phenol, 5-(4-aminopyrimidin-2-ylamino)-2-chlorophenol (56 mg, 0.24 mmol) and $Cs_2CO_3$ (77 mg, 0.24 mmol) in acetone (3.0 mL) was treated with 4-bromo-2-methyl-2-butene (27 μL, 0.24 mmol) at room temperature. The title compound was obtained after purification by flash chromatography on silica gel (hexane:EtOAc 6/4) in 43% yield (31 mg).
$^1$H NMR (500 MHz, $CD_3OD$) δ 7.82 (d, J=5.9 Hz, 1H), 7.46 (d, J=2.1 Hz, 1H), 7.20 (d, J=8.6 Hz, 2H), 7.17 (dd, J=8.6, 2.1 Hz, 1H), 6.01 (d, J=5.9 Hz, 1H), 5.51 (tm, J=6.6 Hz, 1H), 4.62 (d, J=6.6 Hz, 2H), 1.80 (s, 3H) 0.78 (s, 3H); $^{13}$C NMR (125 MHz, CD$_3$OD) 166.3, 161.6, 156.7, 156.0, 142.1, 139.5, 131.0, 121.3, 116.8, 113.9, 107.5, 98.8, 67.3, 26.3, 18.7.

*N$^4$-(4-Methyl-3-(3-methylbut-2-enyloxy)phenyl) pyrimidin-2,4-diamine JLJ000093 (jrIII-73a)

Following the general procedure for O-alkylation of 2-R-5-(heteroaryl-2-ylamino)phenol, 5-(2-aminopyrimidin-4-ylamino)-2-methylphenol (89 mg, 0.41 mmol) and Cs$_2$CO$_3$ (134 mg, 0.41 mmol) in acetone (4.1 mL) was treated with 4-bromo-2-methyl-2-butene (50 µL, 0.41 mmol) at room temperature. The title compound was obtained after purification by flash chromatography on silica gel (CH$_2$Cl$_2$:MeOH 6/4) in 22% yield (26 mg).

$^1$H NMR (500 MHz, CD$_3$OD) δ 7.75 (d, J=6.0 Hz, 1H), 7.13 (s, 1H), 7.05 (d, J=8.0 Hz, 1H), 7.02 (d, J=8.0 Hz, 1H), 6.06 (d, J=6.0 Hz, 1H), 5.51 (tm, J=6.4 Hz, 1H), 4.57 (d, J=6.4 Hz, 2H), 2.16 (s, 3H), 1.81 (s, 3H), 1.77 (s, 3H); $^{13}$C NMR (125 MHz, CD$_3$OD) δ 164.5, 163.8, 158.8, 156.4, 139.9, 138.7, 131.8, 123.5, 122.0, 114.7, 107.2, 98.2, 66.5, 26.3, 18.7, 16.4.

*N$^4$-(4-Chloro-3-(3-methylbut-2-enyloxy)phenyl) pyrimidin-2,4-diamine JLJ000094 (jrIII-77a)

Following the general procedure for O-alkylation of 2-R-5-(heteroaryl-2-ylamino)phenol, 5-(2-aminopyrimidin-4-ylamino)-2-chlorophenol (13 mg, 0.06 mmol) and Cs$_2$CO$_3$ (18 mg, 0.06 mmol) in acetone (1 mL) was treated with 4-bromo-2-methyl-2-butene (6.5 µL, 0.41 mmol) at room temperature. The title compound was obtained after purification by flash chromatography on silica gel (hexane:EtOAc 1/9) in 41% yield (7 mg).

$^1$H NMR (500 MHz, CD$_3$OD) δ 7.79 (d; J=6.0 Hz, 1H), 7.45 (d, J=2.2 Hz, 1H), 7.25 (d, J=8.6 Hz, 1H), 7.22 (dd, J=8.6, 2.2 Hz, 1H), 6.08 (d, J=6.0 Hz, 1H), 5.52 (tm, J=6.6 Hz, 1H), 4.65 (d, J=6.6 Hz, 2H), 1.82 (s, 3H), 1.79 (s, 3H); $^{13}$C NMR (125 MHz, CD$_3$OD) 164.4, 163.4, 156.5, 156.0, 141.4, 139.7, 131.2, 121.2, 118.0, 114.7, 108.4, 98.8, 67.4, 26.3, 18.7.

*N-(4-Chloro-3-(3-methylbut-2-enyloxy)phenyl)-4-methylpyrimidin-2-amine JLJ000090 (jrIII-82a)

Following the general procedure for O-alkylation of 2-R-5-(heteroaryl-2-ylamino)phenol, 2-chloro-5-(4-aminopyrimidin-4-ylamino)phenol (53 mg, 0.22 mmol) and Cs$_2$CO$_3$ (73 mg, 0.22 mmol) in acetone (3 mL) was treated with 4-bromo-2-methyl-2-butene (26 µL, 0.22 mmol) at room temperature. The title compound was obtained after purification by flash chromatography on silica gel (hexane:EtOAc 8/2) in 45% yield (30 mg).

$^1$H NMR (500 MHz, CDCl$_3$) δ 8.28 (d, J=5.0 Hz, 1H), 7.62 (d, J=2.4 Hz, 1H), 7.31 (br s, 1H), 7.25 (d, J=8.6 Hz, 1H), 7.00 (dd, J=8.6, 2.4 Hz, 1H), 6.62 (t, J=5.0 Hz, 1H), 5.55 (tm, J=6.6 Hz, 1H), 4.63 (d, J=6.6 Hz, 2H), 2.42 (s, 3H), 1.79 (s, 3H), 1.76 (s, 3H); $^{13}$C NMR (125 MHz, CDCl$_3$) δ 168.1, 159.7, 157.5, 154.5, 139.4, 138.1, 129.9, 119.5, 115.9, 112.5, 111.7, 105.3, 66.0, 25.8, 24.2, 18.3.

*4-Methoxy-N-(4-methyl-3-(3-methylbut-2-enyloxy)phenyl)pyrimidin-2-amine JLJ000091 (jrIII-81a)

Following the general procedure for O-alkylation of 2-R-5-(heteroaryl-2-ylamino)phenol, 5-(4-aminomethoxypyrimidin-2-ylamino)-2-methylphenol (15 mg, 0.07 mmol) and Cs$_2$CO$_3$ (21 mg, 0.07 mmol) in acetone (1 mL) was treated with 4-bromo-2-methyl-2-butene (7.5 µL, 0.22 mmol) at room temperature. The title compound was obtained after purification by flash chromatography on silica gel (hexane:EtOAC 8/2) in 62% yield (12 mg).

$^1$H NMR (500 MHz, CDCl$_3$) δ 8.12 (d, J=5.7 Hz, 1H), 7.35 (d, J=2.0 Hz, 1H), 7.17 (br s, 1H), 7.06 (d, J=8.1 Hz, 1H), 6.96 (dd, J=8.0, 2.0 Hz, 1H), 6.15 (t, J=5.7 Hz, 1H), 5.52 (tm, J=6.4 Hz, 1H), 4.53 (d, J=6.4 Hz, 2H), 3.96 (s, 3H), 2.19 (s, 3H), 2.00 (s, 3H), 1.73 (s, 3H); $^{13}$C NMR (125 MHz, CDCl$_3$) δ 170.1, 160.1, 158.0, 157.2, 138.3, 137.1, 130.4, 121.2, 120.2, 111.2, 103.8, 99.0, 65.1, 53.4, 25.8, 18.2, 15.8.

*N-(4-Chloro-3-(3-methylbut-2-enyloxy)phenyl)-4-methoxypyrimidin-2-amine JLJ000092 (jrIII-78a)

Following the general procedure for O-alkylation of 2-R-5-(heteroaryl-2-ylamino)phenol, 2-chloro-5-(4-methoxypyrimidin-2-ylamino)phenol (54 mg, 0.22 mmol) and Cs$_2$CO$_3$ (70 mg, 0.22 mmol) in acetone (3 mL) was treated with 4-bromo-2-methyl-2-butene (25 µL, 0.22 mmol) at room temperature. The title compound was obtained after purification by flash chromatography on silica gel (hexane:EtOAc 8/2) in 51% yield (35 mg).

$^1$H NMR (500 MHz, CDCl$_3$) δ 8.14 (d, J=5.7 Hz, 1H), 7.53 (d, J=2.3 Hz, 1H), 7.33 (br s, 1H), 7.26 (d, J=8.5 Hz, 1H), 7.01 (dd, J=8.6, 2.3 Hz, 1H), 6.22 (d, J=5.7 Hz, 1H), 5.54 (tm, J=6.5 Hz, 1H), 4.61 (d, J=6.5 Hz, 2H), 3.96 (s, 3H), 1.78 (s, 3H), 1.74 (s, 3H); $^{13}$C NMR (125 MHz, CDCl$_3$) δ 170.2, 159.7, 157.9, 154.5, 139.3, 138.2, 129.9, 119.4, 116.1, 111.9, 105.3, 99.7, 66.1, 53.5, 25.8, 18.3.

Synthesis of Bicyclic NNRT's According the Present Invention

General Information

NMR spectra were recorded on a Bruker Avance DRX-500 (500 MHz) and DPX-400 (400 MHz) instrument. Column chromatography was carried out employing Merck silica gel (Kieselgel 60, 63-200 µm). Precoated silica gel plates F-254 were used for thin-layer analytical chromatography. HRMS (ESI) analysis was performed at the Mass Spectrometry Laboratory, School of Chemical Sciences, University of Illinois.

Synthetic Details for Heteroaryl Chlorides 13[22]

[22] (a) For the synthesis of chloro-azaindoles, see: Zhang, Z.; Yang, Z.; Meanwell, N. A.; Kadow, J. F.; Wang, T. *J. Org. Chem.* 2002, 34, 2345-2347. (b) For the synthesis of chloro-furopyridines, see: Shiotani, S.; Morita, H. *J. Heterocycl. Chem.* 1982, 19, 1207-1209. (c) For the synthesis of chloro-pyrrolopyrazines, see Romero, R. S.; Franco, F.; Castaneda, A. C.; Muchowski, J. M. U.S. Pat. No. 5,041,442 A 19910820.

1-Chloropyrrolo[1,2-f]pyrimidine (20)

1-Chloropyrrolo[1,2-f]pyrimidine was constructed via Cu(I)-assisted cycloisomerization[23] of propynyl pyrimidine 19, which was derived from regioselective Sonogashira coupling reaction[24] of 2,4-dichloropyrimidine.

[23] (a) Kel'in, A. V.; Sromek, A. W.; Gevorgyan, V. *J. Am. Chem. Soc.* 2001, 123, 2074-2075. (b) Kim, J. T.; Gevorgyan, V. *Org. Lett.* 2002, 4, 4697-4699. (c) Kim, J. T.; Butt, J.; Gevorgyan, V. *J. Org. Chem.* 2004, 69, 5638-5645.

[24] For selective mono cross-coupling reactions of pyrimidine dihalides, see: (a) Tullis, J. S.; VanRens, J. C.; Natchus, M. G.; Clark, M. P.; De, B.; Hsieh, L. C.; Janusz, M. *J. Bioorg. Med. Chem. Lett.* 2003, 13, 1665. (b) Simkovsky, N. M.; Ermann, M.; Roberts, S. M.; Parry, D. M.; Baxter, A. D. *J. Chem. Soc., Perkin Trans. 1* 2002, 1847. (c) Gong, Y.; Pauls, H. W. *Synlett.* 2000, 829. (d) Mangalagiu, I.; Benneche, T.; Undheim, K. *Acta Chem. Scand.* 1996, 50, 914.

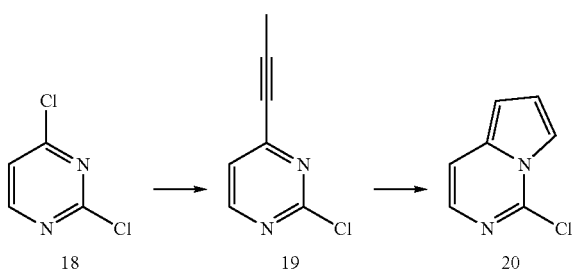

Using a high pressure tube, propyne (5 mL) was condensed in a mixture of 2,4-dichloro-pyrimidine (1.71 g, 11.47 mmol), CuI (228 mg, 1.20 mmol), Pd(PPh₃)₂Cl₂ (0.57 mmol), and Et₃N (50 mL) at −78° C. The mixture was slowly warmed up and stirred at room temperature for 12 h. After this period, the mixture was quenched with aqueous NH₄Cl. The aqueous phase was thoroughly extracted with hexanes. The combined organic extracts were washed with brine, dried over anhydrous Na₂SO₄; and concentrated under reduced pressure. The residue was purified by silica gel chromatography with 5%-15% EtOAc/hexanes to give 19 (1.64 g, 94%).

¹H NMR (400 MHz, CDCl₃, δ): 8.48 (d, J=5.0 Hz, 1H), 7.17 (d, J=5.0 Hz, 1H), 2.06 (s, 3H). ¹³C NMR (100 MHz, CDCl₃, δ): 161.4, 159.3, 153.7, 121.5, 95.1, 77.3, 4.64. LRMS (ES) calcd for C₇H₆ClN₂ [M+1]⁺ 153, found 153.1.

The compound 19 (1.03 g, 6.75 mmol) and CuBr (0.969 g, 6.75 mmol) in DMA-Et₃N (7:1 mixture, 0.02M) was heated at 130° C. for 12 h. The reaction was protected from light by covering the flash with aluminum foil. After this period, the mixture was quenched with aqueous NH₄Cl. The aqueous phase was thoroughly extracted with hexanes. The combined organic extracts were washed with brine, dried over anhydrous Na₂SO₄, and concentrated under reduced pressure. The residue was purified by silica gel chromatography with 10% EtOAc/hexanes to give 20 (125 mg, 12%).

¹H NMR (400 MHz, CDCl₃, δ): 7.44 (dd, J=3.7, 1.8 Hz, 1H), 7.21 (d, J=6.3 Hz, 1H), 7.14 (d, J=6.3 Hz, 1H), 6.84 (t, J=3.1 Hz, 1H), 6.49 (d, J=3.7 Hz, 1H). LRMS (ES) calcd for C₇H₆ClN₂ [M+1]⁺ 153, found 153.1. MS m/z (relative intensity) 152 (M⁺, 100), 117 (32), 90 (14).

1-Choropyrrolo[1,2-a]pyrazine²²ᶜ (23)

1-Choropyrrolo[1,2-a]pyrazine was prepared by chlorination of pyrrolo-pyrazinone 22 with phosphorus oxychloride.

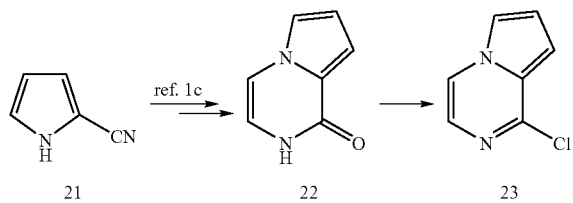 [SMILES: N#Cc1ccc[nH]1 ; O=c1[nH]ccn2cccc12 ; Clc1nccn2cccc12]

Pyrrolo-pyrazinone 22 (2.14 g, 16.0 mmol) in phosphorous oxychloride (20 mL) was stirred at room temperature for 16 h. After this period, the mixture was quenched with ice and neutralized with NaHCO₃. The aqueous phase was thoroughly extracted with CH₂Cl₂. The combined organic extracts were washed with brine, dried over anhydrous Na₂SO₄, and concentrated under reduced pressure. The residue was purified by silica gel chromatography with 10% EtOAc/hexanes to give 23 (1.1 g, 45%).

¹H NMR (500 MHz, CDCl₃, δ): 7.62 (d, J=4.5 Hz, 1H), 7.34 (dd, J=2.5, 1.5 Hz, 1H), 7.12 (d, J=4.5 Hz, 1H), 6.74-6.71 (m, 2H). ¹³C NMR (125 MHz, CDCl₃, δ): 154.4, 126.0, 125.6, 118.3, 117.4, 115.6, 105.2. LRMS (ES) calcd for C₇H₆ClN₂ [M+1]⁺ 153, found 153.2.

4-Chlorofuro[2,3,d]pyrimidine (26)

4-Chlorofuro[2,3,d]pyrimidine was obtained via modified Sandmeyer reaction²⁵ with 4-amino-furopyrimidine 25.²⁶

(25) (a) For the modified Sandmeyer reaction, see: (a) Bracher, F.; Daab, J. Eur. J. Org. Chem. 2002, 2288. (b) Doyle, M. P.; Siegfried, B.; Dellaria, J. F. J. Org. Chem. 1977, 42, 2426.
(26) Nakano, M.; Maeda, Y. WO 2005061516 A1 20050707 CAN 143:115566.

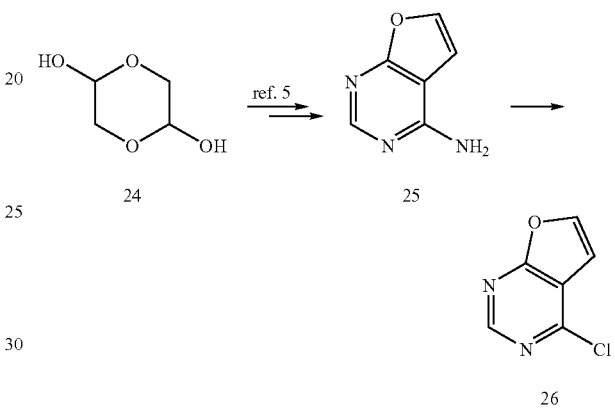

The mixture of 4-amino-furopyrimidine 25 (303 mg, 2.24 mmol), tert-butyl nitrite (5.3 mL, 44.6 mmol), TMSCl (1.4 mL, 11.07 mmol) in acetonitrile (5.0 mL) was stirred at 50° C. for 1.5 h. After this period, the mixture was quenched with 1N NaOH and the aqueous phase was thoroughly extracted with EtOAc. The combined organic extracts were washed with brine, dried over anhydrous Na₂SO₄, and concentrated under reduced pressure. The residue was purified by silica gel chromatography with 10% EtOAc/hexanes to give 26 (139 mg, 40%).

¹H NMR (500 MHz, CDCl₃, δ): 8.68 (s, 1H), 7.72 (d, J=2.5 Hz, 1H), 6.84 (d, J=2.5 Hz, 1H). ¹³C NMR (125 MHz, CDCl₃, δ): 167.1, 154.0, 153.5, 146.0, 177.9, 104.7. MS m/z (relative intensity) 154 (M⁺, 100), 119 (37), 98 (21).

1. ¹H and ¹³C NMR Spectra Data

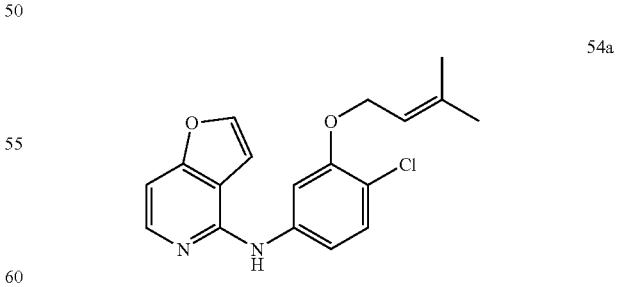

54a

¹H NMR (400 MHz, CDCl₃, δ): 8.10 (d, J=6.4 Hz, 1H), 7.54 (d, J=2.0 Hz, 1H), 7.34 (d, J=2.4 Hz, 1H), 7.29 (bs, 1H), 7.28 (d, J=8.8 Hz, 1H), 7.05 (dd, J=6.4, 0.8 Hz, 1H), 6.95 (dd, J=8.8, 2.8 Hz, 1H), 6.58 (dd, J=2.4, 1.2 Hz, 1H), 5.51 (m, 1H), 4.58 (d, J=6.4 Hz, 2H), 1.77 (s, 3H), 1.71 (s, 3H). ¹³C NMR (100 MHz, CDCl₃, δ): 161.4, 155.0, 150.7, 143.7, 143.8, 140.6, 138.7, 130.4, 119.7, 116.9, 113.6, 111.6, 107.0, 104.4, 101.5, 66.4, 26.2, 18.6. LRMS (ES) calcd for C₁₈H₁₈ClN₂O₂ [M+1]⁺ 329, found 329.1. HRMS (ES) calcd for C₁₈H₁₈ClN₂O₂ [M+1]⁺ 329.1057, found 329.1061.

138.5, 133.6, 130.3, 119.9, 115.9, 112.0, 109.2, 107.5, 105.5, 66.4, 26.3, 18.7. HRMS (ES) calcd for C₁₈H₁₈ClN₂O₂ [M+1]⁺ 329.1057, found 329.1063. LRMS (ES) calcd for C₁₈H₁₈ClN₂O₂ [M+1]⁺ 329, found 329.1. HRMS (ES) calcd for C₁₈H₁₈ClN₂O₂ [M+1]⁺ 329.1057, found 329.1063.

54b

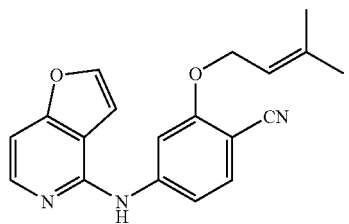

56b

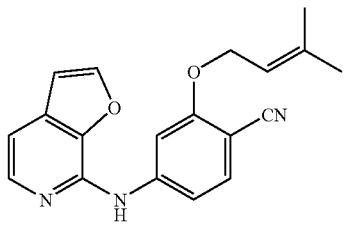

¹H NMR (400 MHz, CDCl₃, δ): 8.14 (d, J=6.0 Hz, 1H), 7.70 (d, J=2.0 Hz, 1H), 7.62 (d, J=2.4 Hz, 1H), 7.42 (d, J=8.4 Hz, 1H), 7.13 (s, 1H), 7.11 (s, 1H), 7.03 (dd, J=8.4, 1.6 Hz, 1H), 6.82 (d, J=1.6 Hz, 1H), 5.48 (t, J=6.8 Hz, 1H), 4.64 (d, J=6.4 Hz, 2H), 1.75 (s, 31-1), 1.73 (s, 3H). ¹³C NMR (100 MHz, CDCl₃, δ): 161.9, 160.8, 148.7, 146.3, 144.2, 142.7, 138.6, 134.0, 118.9, 117.7, 112.4, 110.5, 103.3, 102.4, 102.2, 93.9, 65.9, 25.8, 18.4. LRMS (ES) calcd for C₁₉H₁₈N₃O₂ [M+1]⁺ 320, found 320.1. HRMS (ES) calcd for C₁₉H₁₈N₃O₂ [M+1]⁺ 329.1399, found 329.1402.

¹H NMR (500 MHz, CDCl₃, δ): 8.05 (d, J=5.2 Hz, 1H), 7.93 (s, 1H), 7.69 (d, J=2.0 Hz, 1H), 7.42 (d, J=8.8 Hz, 1H), 7.15-7.10 (m, 3H), 6.61 (d, J=1.6 Hz, 1H), 5.50 (m, 1H), 4.68 (d, J=6.4 Hz, 2H), 1.77 (s, 6H). ¹³C NMR (125 MHz, CDCl₃, δ): 162.3, 147.0, 146.2, 141.0, 140.5, 140.4, 138.9, 134.4, 134.1, 119.4, 118.0, 110.6, 110.4, 107.6, 102.4, 94.4, 66.3, 26.28, 18.8. LRMS (ES) calcd for C₁₉H₁₈N₃O₂ [M+1]⁺ 320, found 320.1. HRMS (ES) calcd for C₁₉H₁₈N₃O₂ [M+1]⁺ 329.1399, found 329.1399.

55

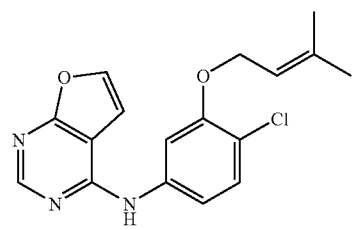

9

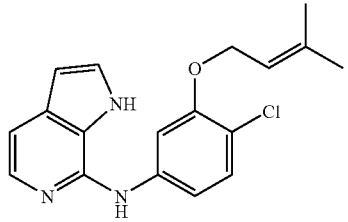

¹H NMR (500 MHz, CDCl₃, δ): 8.39 (s, 1H), 8.93 (bs, 1H), 7.37 (d, J=2.5 Hz, 1H), 7.27 (d, J=8.5 Hz, 1H), 7.17 (d, J=2.5 Hz, 1H), 6.88 (dd, J=8.5, 2.5 Hz, 1H), 6.26 (d, J=2.5 Hz, 1H), 5.40 (m, 1H), 4.50 (d, J=7.0 Hz, 2H), 1.68 (s, 3H), 1.62 (s, 3H). ¹³C NMR (125 MHz, CDCl₃, δ): 167.8, 156.4, 155.2, 154.0, 141.8, 139.1, 138.2, 130.8, 120.1, 119.3, 116.3, 109.7, 104.4, 102.1, 66.6, 26.2, 18.7. LRMS (ES) calcd for C₁₇H₁₇ClN₃O₂ [M+1]⁺ 330, found 330.1. HRMS (ES) calcd for C₁₇H₁₇ClN₃O₂ [M+1]⁺330.1009. found 330.1019.

¹H NMR (500 MHz, CDCl₃, δ): 10.89 (bs, 1H), 10.16 (bs, 1H), 7.33 (d, J=6.0 Hz, 1H), 7.24 (d, J=3.0 Hz, 1H), 6.99 (d, J=6.0 Hz, 1H), 6.94 (d, J=8.0 Hz, 1H), 6.84 (d, J=3.0 Hz, 1H), 6.65 (dd, J=8.5, 2.5 Hz, 1H), 6.44 (d, J=3.0 Hz, 1H), 5.29 (m, 1H), 4.30 (d, J=6.5 Hz, 2H), 1.65 (s, 3H), 1.56 (s, 3H). ¹³C NMR (125 MHz, CDCl₃, δ): 115.5, 141.7, 139.1, 137.7, 134.8, 130.8, 130.5, 128.9, 120.1, 119.4, 119.2, 114.6, 109.2, 108.3, 104.1, 66.4, 26.2, 18.6. LRMS (ES) calcd for C₁₈H₁₉ClN₃O [M+1]⁺ 328, found 328.1. HRMS (ES) calcd for C₁₈H₁₉ClN₃O [M+1]⁺ 328.1217, found 328.1215.

56a

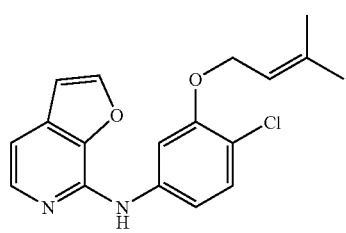

59

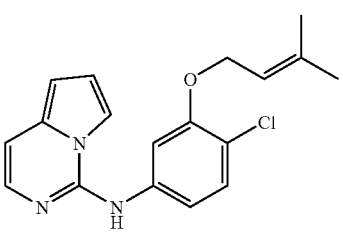

¹H NMR (500 MHz, CDCl₃, δ): 8.03 (d, J=5.5 Hz, 1H), 7.73 (d, J=2.4 Hz, 1H), 7.66 (d, J=2.1 Hz, 1H), 7.28 (d, J=8.5 Hz, 1H), 7.13 (dd, J=8.5, 2.4 Hz, 1H), 7.07 (d, J=5.4 Hz, 1H), 6.94 (s, 1H), 6.77 (d, J=2.0 Hz, 1H), 5.57 (m, 1H), 4.66 (d, J=6.6 Hz, 2H), 1.80 (s, 3H), 1.77 (s, 3H). ¹³C NMR (125 MHz, CDCl₃, δ): 155.0, 146.7, 142.0, 140.5, 140.4, 140.1,

¹H NMR (500 MHz, CDCl₃, δ): 7.50-7.68 (bs, 3H), 7.17 (dd, J=8.5, 1.5 Hz, 1H), 6.89-6.48 (bs, 4H), 6.31 (s, 1H), 5.54 (m, 1H), 4.46 (d, J=6.0 Hz, 2H), 1.67 (s, 3H), 1.62 (s, 3H). LRMS (ES) calcd for C₁₈H₁₉ClN₃O [M+1]⁺ 328, found 328.1. HRMS (ES) calcd for C₁₈H₁₉ClN₃O [M+1]⁺ 328.1217, found 328.1203.

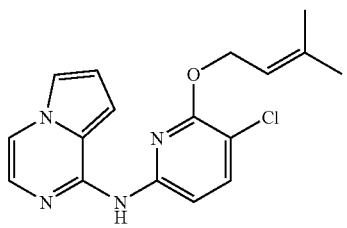

60a

¹H NMR (500 MHz, CDCl₃, δ): 7.67 (d, J=2.5 Hz, 1H), 7.45 (d, J=4.5 Hz, 1H), 7.33 (dd, J=2.5, 1.0 Hz, 1H), 7.29 (d, J=8.5 Hz, 1H), 7.21 (s, 1H), 7.10 (dd, J=8.5, 2.5 Hz, 1H), 6.75 (dd, J=3.5, 2.5 Hz, 1H), 6.66 (d, J=4.0 Hz, 1H), 5.56 (m, 1H), 4.67 (d, J=7.0 Hz, 2H), 1.81 (s, 3H), 1.78 (s, 3H). ¹³C NMR (125 MHz, CDCl₃, δ): 154.9, 148.2, 139.8, 138.6, 130.3, 125.7, 120.3, 119.8, 116.9, 116.6, 113.3, 113.2, 113.0, 106.9, 100.1, 66.5, 26.3, 18.7. LRMS (ES) calcd for $C_{18}H_{19}ClN_3O$ [M+1]⁺ 328, found 328.1. HRMS (ES) calcd for $C_{18}H_{19}ClN_3O$ [M+1]⁺ 328.1217, found 328.1225.

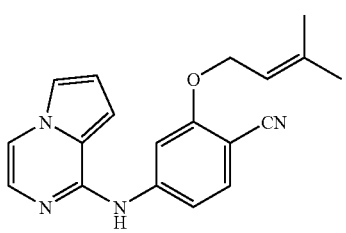

60b

¹H NMR (500 MHz, CDCl₃, δ): 7.83 (s, 1H), 7.43 (d, J=4.5 Hz, 1H), 7.36 (d, J=8.5 Hz, 1H), 7.28 (t, J=1.0 Hz, 1H), 7.13 (d, 4.5 Hz, 1H), 7.04 (dd, J=8.5, 1.5 Hz), 6.70-6.66 (m, 2H), 5.42 (m, 1H), 4.60 (d, J=7.0 Hz, 2H), 1.70 (s, 3H), 1.69 (s, 6H). ¹³C NMR (125 MHz, CDCl₃, δ): 162.2, 147.5, 146.0, 139.0, 134.3, 125.3, 120.4, 119.3, 117.9, 116.9, 113.8, 113.6, 111.6, 103.7, 100.4, 95.0, 66.3, 26.2, 18.8. LRMS (ES) calcd for $C_{19}H_{19}N_4O$ [M+1]⁺ 319, found 319.2. HRMS (ES) calcd for $C_{19}H_{19}N_4O$ [M+1]⁺ 319.1559, found 319.1568.

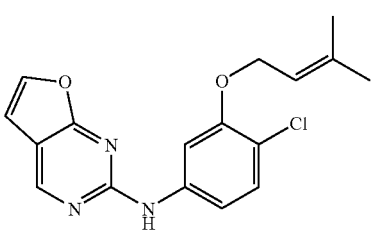

61

¹H NMR (500 MHz, CDCl₃, δ): 8.61 (bs, 1H), 7.49 (d, J=2.0 Hz, 1H), 7.79 (d, J=2.5 Hz, 1H), 7.33 (bs, 1H), 7.21 (d, J=8.5 Hz, 1H), 7.01 (dd, J=8.0, 2.5 Hz, 1H), 6.65 (d, J=2.5 Hz, 1H), 5.48 (m, 1H), 4.59 (d, J=7.0 Hz, 2H), 1.75 (s, 3H), 1.69 (s, 3H). ¹³C NMR (125 MHz, CDCl₃, δ): 168.0, 157.2, 154.6, 151.7, 142.6, 139.0, 138.3, 130.0, 119.5, 116.3, 111.8, 110.5, 105.3, 104.7, 66.1, 25.9, 18.4. LRMS (ES) calcd for $C_{17}H_{17}ClN_3O_2$ [M+1]⁺ 330, found 330.1. HRMS (ES) calcd for $C_{17}H_{17}ClN_3O_2$ [M+1]⁺ 330.1009, found 330.1024.

The above description of the present invention may be used to provide reference without limitation for the invention which is set forth in the following claims.

The invention claimed is:

1. A compound according to structure I:

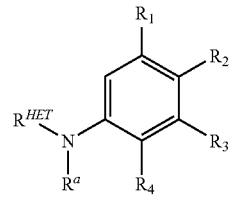

I

Where $R^a$ is H or an optionally OH-substituted $C_1$-$C_3$ alkyl;

$R_1$ is $OR^1$;

$R^1$ is an optionally substituted $C_2$-$C_6$ hydrocarbyl group containing one double bond;

$R_2$, $R_3$ and $R_4$ are each independently H, an optionally substituted $C_1$-$C_4$ alkyl group, halogen, OR, CN, NO₂, a $C_1$-$C_6$ thioether, a $C_1$-$C_6$ thioester group, an optionally substituted $CO_2R$ group, an optionally substituted COR group or an optionally substituted OCOR group;

R is H or an optionally substituted $C_1$-$C_6$ alkyl group;

$R^{HET}$ is

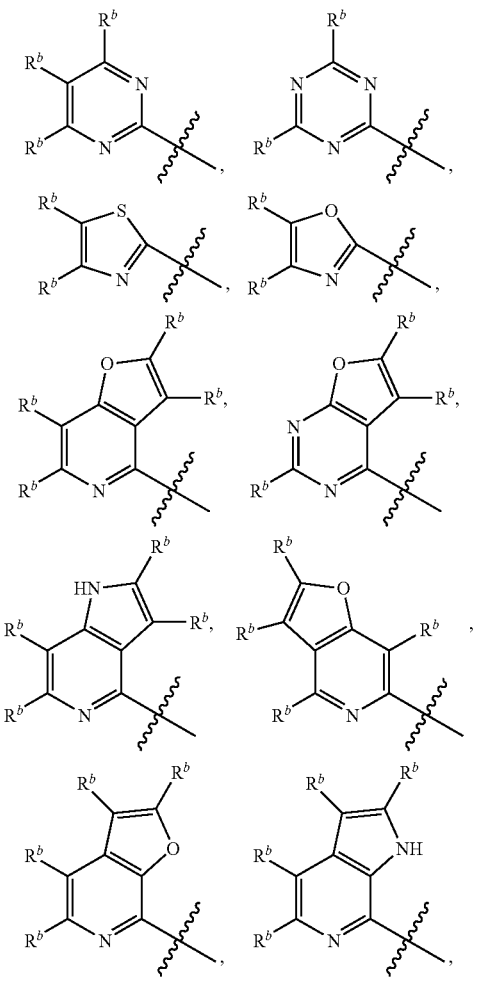

-continued

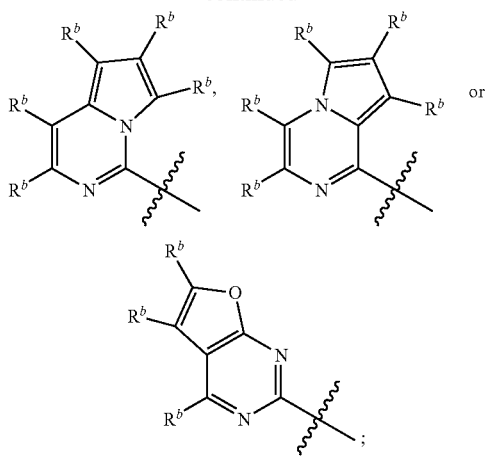

wherein each $R^b$ is independently H, F, Cl, Br, I, CN, Me, Et, $CF_3$, OMe, OEt, OH, $CH_2OH$, $NH_2$, NHMe, SMe or $NO_2$, and pharmaceutically acceptable salts thereof.

2. The compound according to claim 1 wherein $R^{HET}$ is

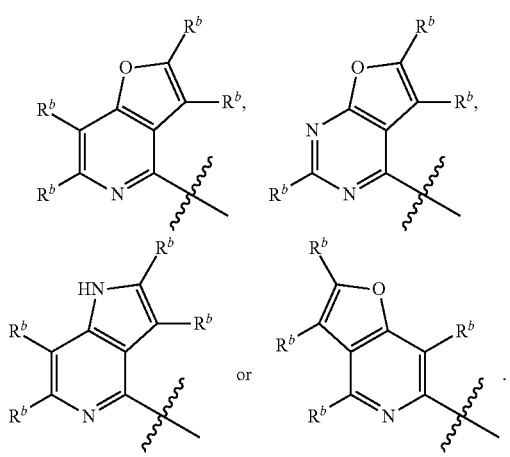

3. The compound according to claim 1 wherein $R^{HET}$ is

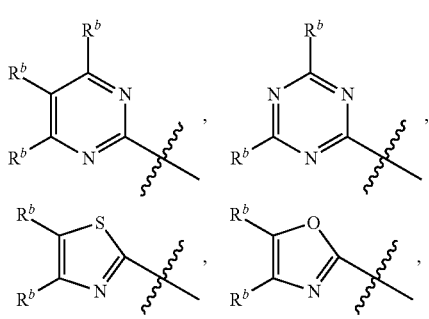

-continued

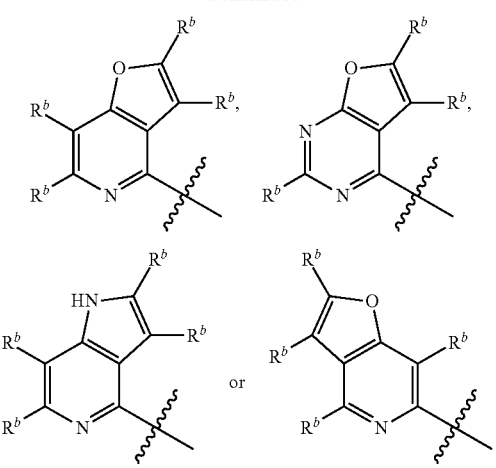

4. The compound according to claim 1 wherein $R^{HET}$ is

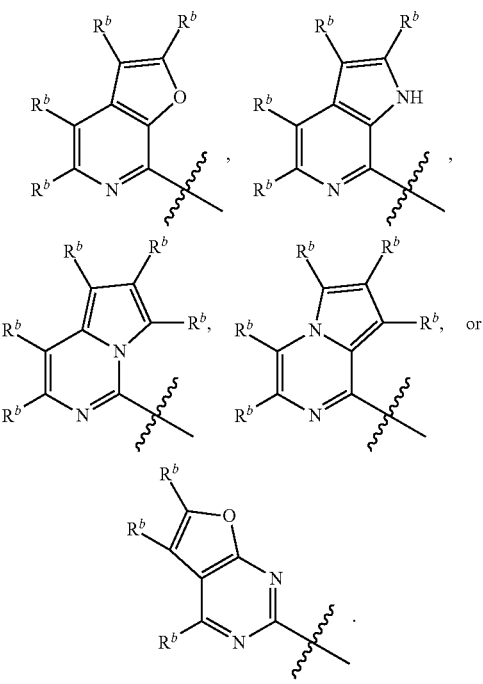

5. The compound according to claim 1 wherein $R^{HET}$ is

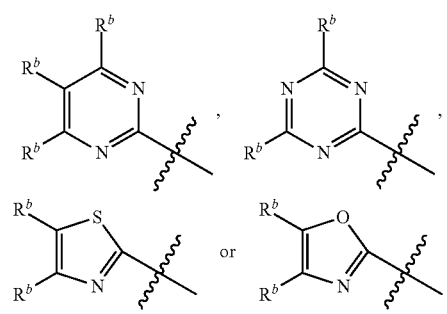

6. The compound according to claim 1 wherein $R^{HET}$ is

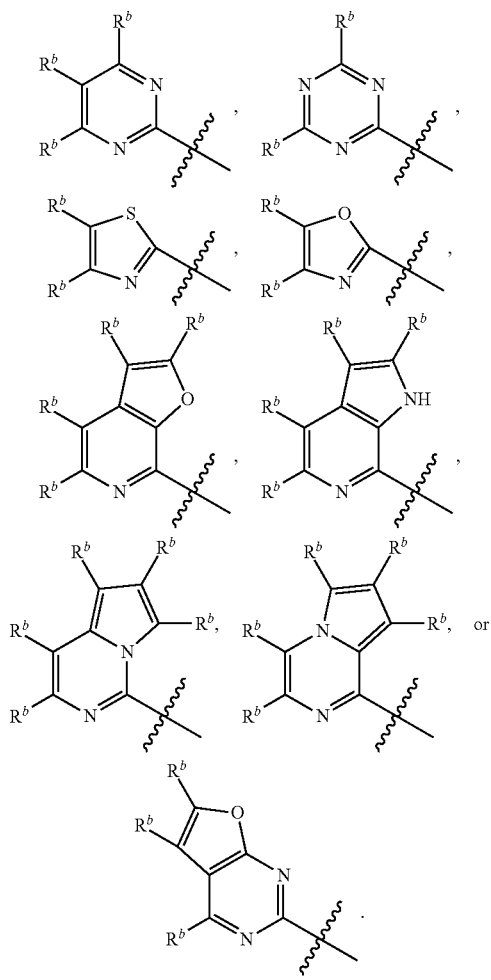

7. A compound according to structure I:

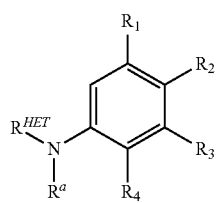

Where $R^a$ is H or an optionally OH-substituted $C_1$-$C_3$ alkyl;
$R_1$ is $OR^1$;
$R^1$ is an optionally substituted $C_2$-$C_6$ hydrocarbyl group containing one double bond;
$R_2$, $R_3$ and $R_4$ are each independently H, an optionally substituted $C_1$-$C_4$ alkyl group, halogen, OR, CN, $NO_2$, a $C_1$-$C_6$ thioether, a $C_1$-$C_6$ thioester group, an optionally substituted $CO_2R$ group, an optionally substituted COR group or an optionally substituted OCOR group;
R is H or an optionally substituted $C_1$-$C_6$ alkyl group;
$R^{HET}$ is an optionally substituted furanyl, pyrrolyl, thienyl, thiazoyl, pyridinyl, triazinyl, pyridazinyl, pyrimidinyl, pyrazinyl, triazolyl, oxazolyl indole, benzofuran, pyrrolopyrimidine, pyrrolopyrazine, furopyrimidine, isoquinoline or quinoline group, which, when substituted, are substituted by one, two or three groups which are each independently selected from the group consisting of halogen, CN, optionally substituted $C_1$-$C_3$ alkyl, $CF_3$, OH, O($C_1$-$C_3$ alkyl), $NH_2$, NH($C_1$-$C_2$ alkyl), N-di($C_1$-$C_2$ alkyl), S($C_1$-$C_3$ alkyl) and $NO_2$;
and pharmaceutically acceptable salts thereof.

8. The compound according to claim 1 wherein $R_a$ is H.

9. The compound according to claim 8 wherein $R_2$ is Cl or CN.

10. A pharmaceutical composition comprising an effective amount of a compound according to claim 1, optionally in combination with a pharmaceutically acceptable carrier, additive or excipient.

11. A pharmaceutical composition comprising an effective amount of a compound according to claim 2, optionally in combination with a pharmaceutically acceptable carrier, additive or excipient.

12. A pharmaceutical composition comprising an effective amount of a compound according to claim 3, optionally in combination with a pharmaceutically acceptable carrier, additive or excipient.

13. A pharmaceutical composition comprising an effective amount of a compound according to claim 4, optionally in combination with a pharmaceutically acceptable carrier, additive or excipient.

14. A pharmaceutical composition comprising an effective amount of a compound according to claim 5, optionally in combination with a pharmaceutically acceptable carrier, additive or excipient.

15. A pharmaceutical composition comprising an effective amount of a compound according to claim 6, optionally in combination with a pharmaceutically acceptable carrier, additive or excipient.

16. A pharmaceutical composition comprising an effective amount of a compound according to claim 7, optionally in combination with a pharmaceutically acceptable carrier, additive or excipient.

17. A pharmaceutical composition comprising an effective amount of a compound according to claim 8, optionally in combination with a pharmaceutically acceptable carrier, additive or excipient.

18. A compound according to the chemical structure II

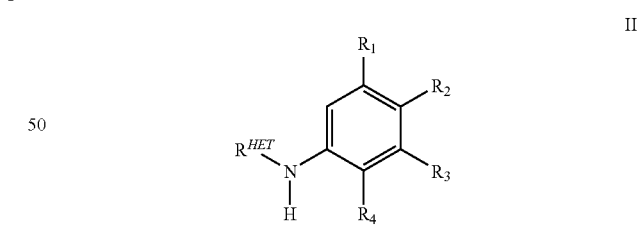

where $R_1$ is 3,3, dimethylallyloxy, 2-furanylmethoxy, 3-furanylmethoxy, 2-thienylmethoxy, 2-thiazolylmethoxy, 3-pyrrolylmethyl, 3-pyrrolylmethoxy, N-methyl-3-pyrrolylmethyl, N-methyl-3-pyrrolylmethoxy, cyclopent-1-enylmethyl, 2-methyl-cyclopen-1-enylmethoxy and cyclohexyloxy, each of which is optionally substituted with one or two groups selected from the group consisting of F, Cl, Br, I, CN, Me, Et, $CF_3$, OMe, OEt, OH, $CH_2OH$, $NH_2$, NHMe, SMe and $NO_2$;
$R_2$ is H, F, Cl, Br, I, CN, Me, Et, $CF_3$, OMe, OEt, SMe, COOH, $CH_2OMe$ or COOMe;
$R_3$ is H, F, Cl, Br, I, CN, Me, Et, $CF_3$, OME or SMe;

$R_4$ is H; and

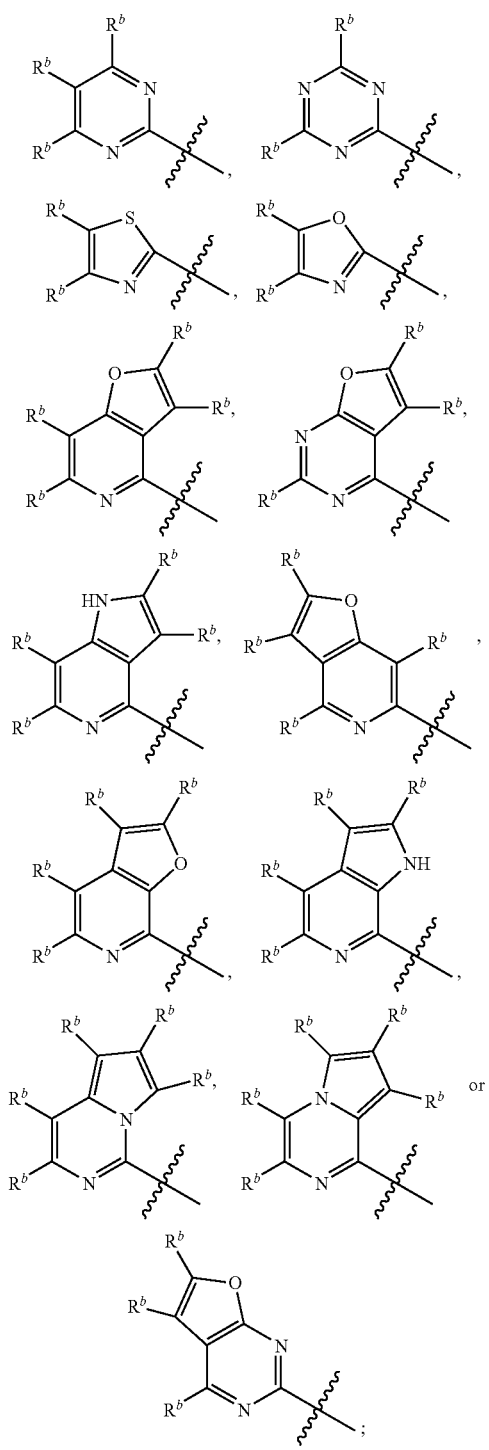

Where each $R^b$ is independently H, F, Cl, Br, I, CN, Me, Et, $CF_3$, OMe, OEt, OH, $CH_2OH$, $NH_2$, NHMe, SMe or $NO_2$; and pharmaceutically acceptable salts, solvates, and polymorphs thereof.

19. The compound according to claim 18 where $R_1$ is dimethylallyloxy; $R_2$ is Cl or CN; and $R^{HET}$ is

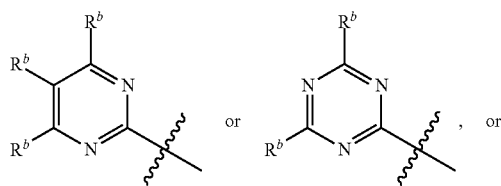

a pharmaceutically acceptable salt thereof.

20. The compound according to claim 19 according to the chemical structure:

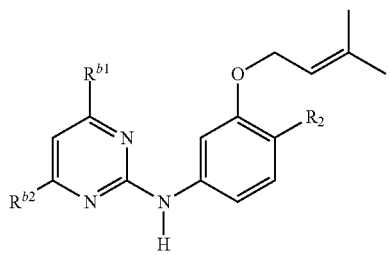

Where $R_2$ is Cl or CN;
$R^{b1}$ is OMe, $NH_2$, NHMe, SMe, OEt, H, Me or Et and
$R^{b2}$ is H, OMe or $NH_2$, or
a pharmaceutically acceptable salt thereof.

21. The compound according to claim 19 according to the chemical structure:

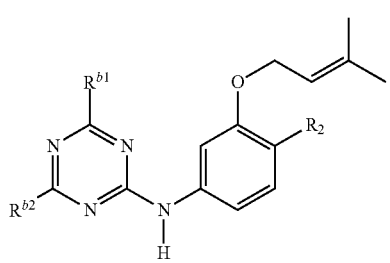

Where $R_2$ is Cl or CN;
$R^{b1}$ is Cl, OMe, $NH_2$, NHMe, SMe or Me and
$R^{b2}$ is H, Cl, OMe, Me or $NH_2$, or
a pharmaceutically acceptable salt thereof.

22. A compound according to the chemical structure:

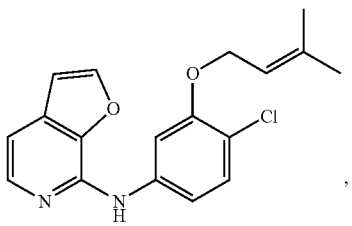

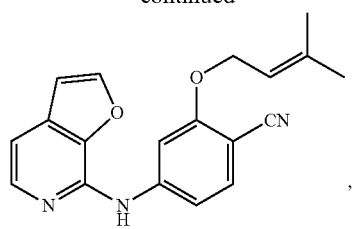,
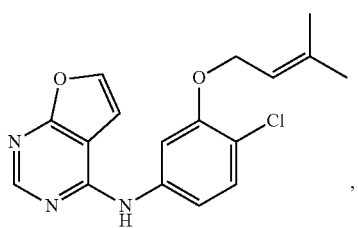,
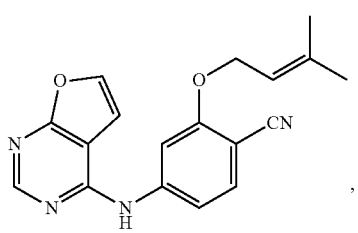,
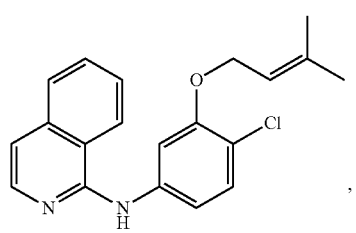,
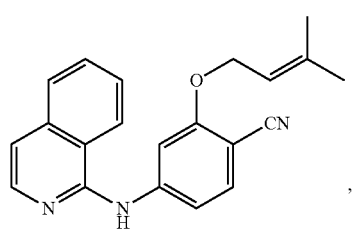,
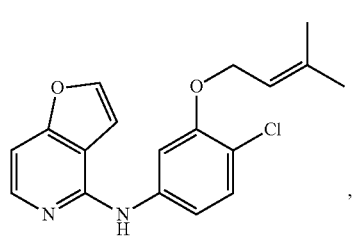,
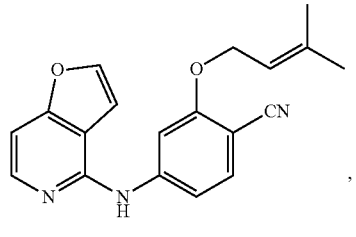,
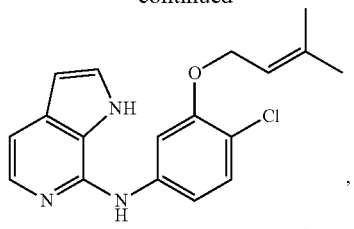,
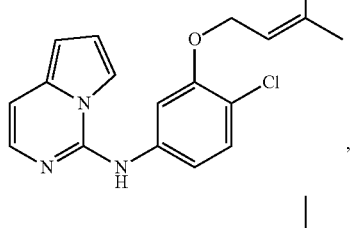,
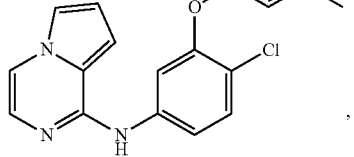,
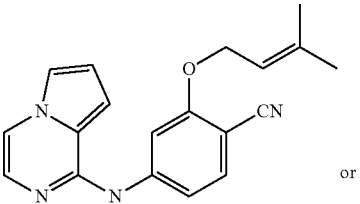 or
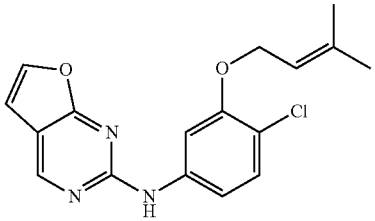,
or a pharmaceutically acceptable salt thereof.
23. A compound according to claim 22 according to the chemical structure:
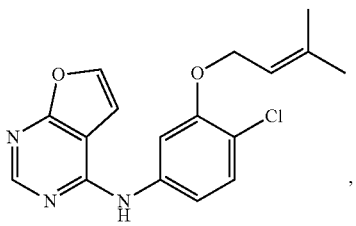,
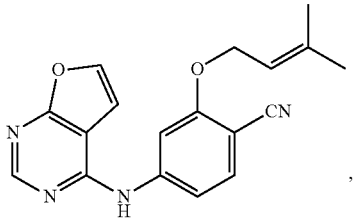, -continued

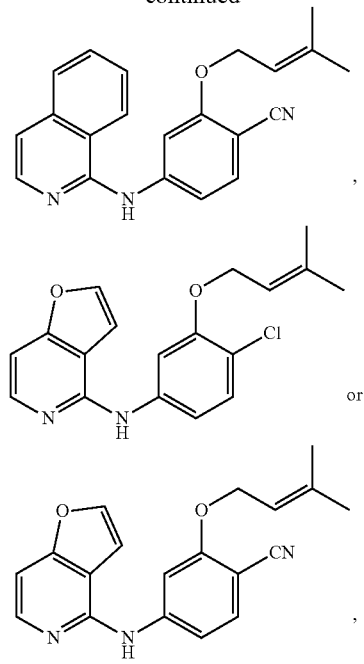

or a pharmaceutically acceptable salt thereof.

24. A pharmaceutical composition comprising an effective amount of a compound according to claim 18, optionally in combination with a pharmaceutically acceptable carrier, additive or excipient.

25. A pharmaceutical composition comprising an effective amount of a compound according to claim 19, optionally in combination with a pharmaceutically acceptable carrier, additive or excipient.

26. A pharmaceutical composition comprising an effective amount of a compound according to claim 20, optionally in combination with a pharmaceutically acceptable carrier, additive or excipient.

27. A pharmaceutical composition comprising an effective amount of a compound according to claim 21, optionally in combination with a pharmaceutically acceptable carrier, additive or excipient.

28. A pharmaceutical composition comprising an effective amount of a compound according to claim 22, optionally in combination with a pharmaceutically acceptable carrier, additive or excipient.

29. A pharmaceutical composition comprising an effective amount of a compound according to claim 23, optionally in combination with a pharmaceutically acceptable carrier, additive or excipient.

* * * * *